United States Patent
Demuth et al.

(10) Patent No.: US 8,142,764 B2
(45) Date of Patent: Mar. 27, 2012

(54) SYNTHETIC BIOFILM-INHIBITING PEPTIDES

(75) Inventors: Donald R. Demuth, Louisville, KY (US); Carlo Amorin Daep, Louisville, KY (US)

(73) Assignee: University of Louisville Research Foundation, Louisville, KY (US)

( * ) Notice: Subject to any disclaimer, the term of this patent is extended or adjusted under 35 U.S.C. 154(b) by 448 days.

(21) Appl. No.: 12/392,966

(22) Filed: Feb. 25, 2009

(65) Prior Publication Data

US 2009/0214603 A1    Aug. 27, 2009

Related U.S. Application Data

(60) Provisional application No. 61/031,934, filed on Feb. 27, 2008, provisional application No. 61/127,797, filed on May 14, 2008.

(51) Int. Cl.
- A61K 38/10 (2006.01)
- A61K 38/16 (2006.01)
- A61Q 11/00 (2006.01)
- C07K 7/08 (2006.01)
- C07K 14/00 (2006.01)

(52) U.S. Cl. ............ 424/49; 424/435; 424/484; 514/2.4; 514/21.3; 514/21.4; 514/21.5; 514/835; 530/324; 530/325; 530/326; 530/327

(58) Field of Classification Search .................. None
See application file for complete search history.

(56) References Cited

U.S. PATENT DOCUMENTS

| 4,559,157 A | 12/1985 | Smith et al. |
| 4,608,392 A | 8/1986 | Jacquet et al. |

(Continued)

OTHER PUBLICATIONS

Daep et al. Interaction of *Porphyromonas gingivalis* with Oral Streptococci . . . Infection and Immunity. Jul. 2008, vol. 76, No. 7, pp. 3273-3280.*

(Continued)

*Primary Examiner* — Jeffrey E Russel
(74) *Attorney, Agent, or Firm* — Viksnins Harris & Padys PLLP

(57) ABSTRACT

The present invention provides streptococcal SspB Adherence Region (BAR) peptides consisting of Formula I: $R_{18}$-$R_1$-$R_2$-Val-$R_3$-$R_4$-Leu-Leu-$R_5$-$R_6$-$R_7$-Ile-$R_8$-$R_9$-Lys-$R_{10}$-$R_{19}$, wherein $R_2$, is 1-3 Lys residues; $R_3$ is any amino acid residue except a Pro residue; $R_4$ is any amino acid residue except a Pro residue; $R_5$ is 1-3 Lys residues; $R_6$ is 1-10 amino acid residues; $R_7$ is any amino acid residue except Asp, Glu, Gly or Pro; $R_8$ is any amino acid residue except Ala, Asp, Gly, His, Ile, Pro, Trp or Tyr; $R_9$ is a Val, Ile, Phe, or Trp residue; $R_{10}$ is 0-1 Cys residue; $R_{18}$ is 0 amino acids or $R_{12}$-$R_{11}$-Pro-, wherein $R_{11}$ is 0-3 amino acids, wherein the amino acid residues are not Gly or Pro; and $R_{12}$ is 0-1 Cys residues; and $R_{19}$ is $R_{13}$-$R_{14}$-$R_{15}$-$R_{16}$-$R_{17}$, wherein $R_{13}$ is 0-1 is Gly residue; $R_{14}$ is 0-1 Ala residue; $R_{15}$ is 0-1 Phe residue; $R_{16}$ is 0-1 Gln residue; $R_{17}$ is 0-1 Cys residue; and wherein $R_1$ is an ornithine residue; or wherein both $R_1$ and $R_{10}$ are both Cys and $R_1$ and $R_{10}$ are covalently linked to form a circular peptide; or wherein $R_1$ is 0-1 Cys or an ornithine residue and $R_{12}$ and $R_{17}$, are both Cys and $R_{12}$ and $R_{17}$ are covalently linked to form a circular peptide. Embodiments of the present invention further provide devices coated with the BAR peptides.

18 Claims, 18 Drawing Sheets

U.S. PATENT DOCUMENTS

| | | | |
|---|---|---|---|
| 4,612,302 | A | 9/1986 | Szabo et al. |
| 4,684,620 | A | 8/1987 | Hruby et al. |
| 4,820,508 | A | 4/1989 | Wortzman |
| 4,853,371 | A | 8/1989 | Coy et al. |
| 4,938,949 | A | 7/1990 | Borch et al. |
| 4,992,478 | A | 2/1991 | Geria |
| 5,591,227 | A | 1/1997 | Dinh et al. |
| 5,599,352 | A | 2/1997 | Dinh et al. |
| 5,697,967 | A | 12/1997 | Dinh et al. |
| 6,702,850 | B1 | 3/2004 | Byun et al. |
| 6,962,706 | B1 | 11/2005 | O'Brien-Simpson et al. |
| 7,041,127 | B2 | 5/2006 | Ledergerber |
| 7,055,237 | B2 | 6/2006 | Thomas |
| 7,105,018 | B1 | 9/2006 | Yip et al. |
| 7,135,038 | B1 | 11/2006 | Limon |
| 7,144,422 | B1 | 12/2006 | Rao |
| 7,156,869 | B1 | 1/2007 | Pacetti |
| 7,163,555 | B2 | 1/2007 | Dinh |
| 7,186,789 | B2 | 3/2007 | Hossainy et al. |
| 7,273,493 | B2 | 9/2007 | Ledergerber |
| 2004/0005276 | A1 | 1/2004 | Reynolds et al. |
| 2004/0224897 | A1 | 11/2004 | Leung et al. |

OTHER PUBLICATIONS

Daep et al. Structural Characterization of Peptide-Mediated Inhibition of *Porphyromonas gingivalis* Biofilm Formation. Infection and Immunity. Oct. 2006, vol. 74, No. 10, pp. 5756-5762.*

International Search Report and Written Opinion of the International Searching Authority, PCT/US2009/035168, 15 pages, Oct. 5, 2009.

Aduse-Opoku, et al., "Generation of Lys-gingipain protease activity in *Porphyromonas gingivalis* W50 is independent of Arg-gingipain protease activities", *Microbiology*, 146, 1933-1940, 2000.

Andrade, M.A., et al., "Evaluation of secondary structure of proteins from UV circular dichroism spectra using an unsupervised learning neural network", *Prot. Eng.*, 6, 383-390, 1993.

Boatman, P.D., et al., "Secondary structure peptide mimetics: Design, synthesis and evaluation of beta-strand mimetic thrombin inhibitors", *J. Med. Chem.* 42, 1367-1375, 1999.

Bradshaw, D. J., et al., "Role of *Fusobacterium nucleatum* and coaggregation in anaerobe survival in planktonic and biofilm oral microbial communities during aeration", *Infect. Immun.*, 66, 4729-4732, 1998.

Brooks, W., et al., "Identification of a *Streptococcus gordonii* SspB domain that mediates adhesion to *Porphyromonas gingivalis*", *Infect. Immun.*, 65, 3753-3758, 1997.

Brunel, F.M., et al., "Synthesis of constrained helical peptides by thioether ligation: application to analogs of gp41", *Chem. Commun.*, 2552-2554, 2005.

Chen, T., et al., "Comparative whole-genome analysis of virulent and avirulent strains of *Porphyromonas gingivalis*", *J. Bacteriol.*, 186, 5473-5479, 2004.

Chung, W. O., et al., "Identification of a *Porphyromonas gingivalis* receptor for the *Streptococcus gordonii* SspB protein", *Infect. Immun.*, 68, 6758-6762 and one supplemental page, 2000.

Chung, W.O., et al., "Signaling system in *Porphyromonas gingivalis* based on a LuxS protein", *J. Bacteriol.*, 183, 3903-3909, 2001.

Cook, G. S., et al., "Biofilm formation by *Porphyromonas gingivalis* and *Streptococcus gordonii*", *J. Periodontal. Res.*, 33, 323-327, 1998.

Curtis, M.A., et al., "Cysteine proteases of *Porphyromonas gingivalis*", *Crit. Rev. Oral Biol. Med.*, 12 192-216, 2001.

Curtis, M. A., et al., "Molecular genetics and nomenclature of proteases of *Porphyromonas gingivalis*", *J. Periodontal. Res.*, 34, 464-472, 1999.

Daep, C.A., et al., "Interaction of *Porphyromonas gingivalis* with oral streptococci requires a motif that resembles the eukaryotic nuclear receptor box protein—protein interaction domain", *Infect. Immun.*, 76, 3273-3280, 2008.

Daep, C. A., et al., "Structural Characterization of Peptide-Mediated Inhibition of *Porphyromonas gingivalis* Biofilm Formation", *Infect. Immun.*, 74, 5756-5762, 2006.

Dal Pozzo, A., et al., "Synthesis and anti-aggregatory activity of linear retro-inverso RGD peptides", *J. Pept. Res.*, 55, 447-454, 2000.

Demuth, D.R., et al., "Cloning and expression of a *Streptococcus sanguis* surface antigen that interacts with a human salivary agglutinin", *Infect. Immun.*, 56, 2484-2490, 1988.

Demuth, D.R., et al., "Comparison of *Streptococcus mutans* and *Streptococcus sanguis* receptors for human salivary agglutinin", *Microb. Pathogenesis*, 9, 199-211, 1990.

Demuth, D.R., et al., "Discrete Protein Determinant Directs the Species-Specific Adherence of *Porphyromonas gingivalis* to Oral Streptococci", *Infect. Immun.*, 69, 5736-5741, 2001.

Demuth, D.R., et al., "Saliva-mediated aggregation of *Enterococcus faecalis* transformed with a *Streptococcus sanguis* gene encoding the SSP-5 surface antigen", *Infect. Immun.*, 57, 1470-1475, 1989.

Demuth, D.R., et al., "Streptococcal-Host Interactions: Structural and functional analysis of a *Streptococcus sanguis* receptor for a human salivary glycoprotein", *J. Biol. Chem.* 265, 7120-7126, 1990.

Demuth D.R., et al., "Structural and functional variation within the alanine-rich repetitive domain of streptococcal antigen I/II", *Infect. Immun.*, 70, 6389-6398, 2002.

Demuth, D.R., et al., "Tandem genes encode cell-surface polypeptides SspA and SspB which mediate adhesion of the oral bacterium *Streptococcus gordonii* to human and bacterial receptors", *Mol. Microbiol.*, 20, 403-413, 1996.

Diaz P.I., et al., "*Fusobacterium nucleatum* supports the growth of *Porphyromonas gingivalis* in oxygenated and carbon-dioxide-depleted environments", *Microbiology*, 148, 467-472, 2002.

Drobni, M., et al., "Host-derived pentapeptide affecting adhesion, proliferation, and local pH in biofilm communities composed of *Streptococcus* and *Actinomyces* species", *Infect. Immun.*, 74, 6293-6299. 2006.

Duan, Y., et al., "Calcium-Binding Properties of SSP-5, the *Streptococcus gordonii* M5 Receptor for Salivary Agglutinin", *Infect. Immun.*, 62, 5220-5226, 1994.

Eguchi, M., et al., "Solid-phase synthesis and solution structure of bicyclic beta-turn peptidomimetics: diversity at the i position", *Tet. Lett.*, 42, 1237-1239, 2001.

El-Sabaeny, A., et al., "Environmental conditions modulate the expression of the *sspA* and *sspB* genes in *Streptococcus gordonii*", *Microbial Pathogen*, 29, 101-113, 2000.

El-Sabaeny, A., et al., "Regulation of *Streptococcus gordonii sspB* by the *sspA* gene product", *Infect. Immun.*, 69, 6520-6522, 2001.

Fan, Q., et al., "Antigenic cross-reactivity among *Porphyromonas gingivalis* serotypes", *Oral. Microbiol. Immunol.*, 15, 158-165, 2000.

Frandsen, E.V., et al., "Ecology of viridans streptococci in the oral cavity and pharynx", *Oral Mivrobiol. Immunol.*, 6, 129-133, 1991.

Galande, A.K., et al., "Thioether side chain cyclization for helical peptide formation: inhibitors of estrogen receptor-coactivator interactions", *J. Peptide Res.* 63, 297-302, 2004.

Grenier, D. and B. C. McBride, "Isolation of a membrane-associated *Bacteroides gingivalis* glycylprolyl protease", *Infect. Immun.*, 55, 3131-3136, 1987.

Grenier, D. and B. C. McBride, "Surface location of a *Bacteroides gingivalis* glycylprolyl protease", *Infect. Immun.*, 57, 3265-3269, 1989.

Grenier, D., "Demonstration of a bimodal coaggregation reaction between *Porphyromonas gingivalis* and *Treponema denticola*", *Oral. Microbiol. Immunol.*, 7, 280-284, 1992.

Grenier, D. et al., "Effect of inactivation of the Arg- and/or Lys-gingipain gene on selected virulence and physiological properties of *Porphyromonas gingivalis*", *Infect. Immun.*, 71, 4742-4748, 2003.

Grenier, D. et al., "Role of gingipains in growth of *Porphyromonas gingivalis* in the presence of human serum albumin", *Infect. Immun.*, 69, 5166-5172, 2001.

Hanessian, S., et al., "Design and synthesis of conformationally constrained amino acids as versatile scaffolds and peptide mimetics", *Tetrahedron*, 53, 12789-12854, 1997.

Hinode, D. et al., "Purification and characterization of three types of proteases from culture supernatants of *Porphyromonas gingivalis*", *Infect. Immun.*, 59, 3060-3068, 1991.

Holt, S. C. and J. L. Ebersole, "*Porphyromonas gingivalis, Treponema denticola, and Tannerella forsythia*: the "red complex", a prototype polybacterial pathogenic consortium in periodontitis", *Periodontol.* 2000, 38, 72-122, 2005.

Holt, S. C. et al., "Implantation of *Bacteroides gingivalis* in nonhuman primates initiates progression of periodontitis", *Science*, 239, 55-60, 1988.

Holt, S. C. et al., "Virulence factors of *Porphyromonas gingivalis*", 1999. *Periodontol.* 2000, 20,168-238, 1999.

Hosogi, Y., et al., "Gene expression in *Porphyromonas gingivalis* after contact with human epithelial cells", *Infect. Immun.*, 73, 2327-2335, 2005.

Ikegami, A. et al., "Multiple functions of the leucine-rich repeat protein LrrA of *Treponema denticola*", *Infect. Immun.*, 72, 4619-4627, 2004.

Jenkinson, H. F. and D. R. Demuth, "Structure, function and immunogenicity of streptococcal antigen I/II polypeptides", *Mol. Microbiol.*, 23, 183-190, 1997.

Katz, J., et al., "Effect of host responses on the pathogenicity of strains of *Porphyromonas gingivalis*", *Oral Microbiol. Immunol.*, 5, 309-318, 1996.

Kim, H.O. and M. Kahn, "A merger of rational drug design and combinatorial chemistry: Development and application of peptide secondary structure mimetics", *Comb. Chem. High-Throughput Screening*, 3, 167-183, 2000.

Kinder, S. A. and S. C. Holt, "Characterization of coaggregation between *Bacteroides gingivalis* T22 and *Fusobacterium nucleatum* T18", *Infect. Immun.*, 57, 3425-3433, 1989.

Kinder, S. A. and S. C. Holt, "Localization of the *Fusobacterium nucleatum* T18 adhesin activity mediating coaggregation with *Porphyromonas gingivalis* T22", *J. Bacteriol.*, 175, 840-850, 1993.

Kolenbrander, P. E. and R. N. Andersen, "Inhibition of coaggregation between *Fusobacterium nucleatum* and *Porphyromonas* (*Bacteroides*) *gingivalis* by lactose and related sugars", *Infect. Immun.*, 57, 3204-3209, 1989.

Kuboniwa, M., et al., "*Streptococcus gordonii* utilizes several distinct gene functions to recruit *Porphyromonas gingivalis* into a mixed community", *Mol. Microbiol.*, 60, 121-139, 2006.

Kuramitsu, H. K. et al., "Biofilm formation by the periodontopathic bacteria *Treponema denticola* and *Porphyromonas gingivalis*", *J. Periodontol.*, 76, 2047-2051, 2005.

Kuramitsu, H. K., "Proteases of *Porphyromonas gingivalis*: what don't they do?", *Oral Microbiol.Immunol.*, 13, 263-270, 1998.

Lamont, R. J. and H. F. Jenkinson, "Life below the gum line: pathogenic mechanisms of *Porphyromonas gingivalis*", *Microbiol. Mol. Biol. Rev.*, 62, 1244-1263, 1998.

Lamont, R. J. et al., "Characterization of the adherence of *Porphyromonas gingivalis* to oral streptococci", *Oral Microbiol. Immunol.*, 7, 193-196, 1992.

Lamont, R. J. et al., "Molecules of *Streptococcus gordonii* that bind to *Porphyromonas gingivalis*", *Microbiology*, 140, 867-872, 1994.

Lamont, R.J., et al., "Role of *Streptococcus gordonii* SspB protein in the development of *Porphyromonas gingivalis* biofilms on streptococcal substrates", *Microbiol.*, 148, 1627-1636, 2002.

Love, R.M., et al., "Coinvasion of Dentinal Tubules by *Porphyromonas gingivalis* and *Streptococcus gordonii* Depends upon Binding Specificity of Streptococcal Antigen I/II Adhesin", *Infect. Immun.*, 68, 1359-1365, Mar. 2000.

Ma, J. K. et al., "Conservation of the gene encoding streptococcal antigen I/II in oral streptococci", *Infect. Immun.*, 59, 2686-2694, 1991.

Macrina, F.L., et al., "A cloning vector able to replicate in *Escherichia coli* and *Streptococcus sanguis*", *Gene* 19, 345-353, 1982.

Maeda, K. et al., "Glyceraldehyde-3-phosphate dehydrogenase of *Streptococcus oralis* functions as a coadhesin for *Porphyromonas gingivalis* major fimbriae", *Infect. Immun.*, 72, 1341-1348, 2004.

Mayrand, D. and S. C. Holt, "Biology of asaccharolytic black-pigmented Bacteroides species", *Microbiol. Rev.*, 52, 134-152, 1988.

Merelo, J.J., et al., "Proteinotopic Feature Maps", *Neurocomputing*, 6, 443-454, 1994.

Mikolajczyk-Pawlinska, J. et al., "Genetic variation of *Porphyromonas gingivalis* genes encoding gingipains, cysteine proteinases with arginine or lysine specificity", *Biol. Chem.*, 379, 205-211, 1998.

Munro, G.H., et al., "A protein fragment of streptococcal cell surface antigen I/II which prevents adhesion of *Streptococcus mutans*", *Infect. Immun.*, 61, 4590-4598, 1993.

Nelson, K. E. et al., "Complete genome sequence of the oral pathogenic *Bacterium Porphyromonas gingivalis* strain W83", *J. Bacteriol.*, 185, 5591-5601 and one supplemental page, 2003.

Nishikawa, K., et al., "A regulation cascade controls expression of *Porphyromonas gingivalis* fimbriae via the FimR response regulator", *Mol. Microbiol.*, 54, 546-560, 2004.

Nori, Y., et al., "Localization of *Porphyromonas gingivalis*-carrying fimbriae in situ in human periodontal pockets", *J. Dent. Res.*, 83, 941-945, 2004.

O-Brien-Simpson, N.M. et al., "*Porphyromonas gingivalis* gingipains: the molecular teeth of a microbial vampire", *Curr. Protein Pept. Sci.*, 4, 409-426, 2003.

Onagawa, M. et al., "Coaggregation between *Porphyromonas gingivalis* and *Treponema denticola*", *Bull. Tokyo Dent. Coll.*, 35, 171-181, 1994.

Park,Y., et al., "Short fimbriae of *Porphyromonas gingivalis* and their role in coadhesion with *Streptococcus gordonii*", *Infect. Immun.*, 73, 3983-3989, 2005.

Petit, M.C. et al., "Solution structure of a retro-inverso peptide analogue mimicking the foot-and-mouth disease virus major antigenic site. Structural basis for its antigenic cross-reactivity with the parent peptide", *J. Biol. Chem.*, 274, 3686-3692, 1999.

Pike, R., et al., "Lysine- and arginine-specific proteinases from *Porphyromonas gingivalis*. Isolation, characterization, and evidence for the existence of complexes with hemagglutinins", *J. Biol. Chem.*, 269, 406-411, 1994.

Potempa, J., et al., "Titration and mapping of the active site of cystiene proteinases from *Porphyromonas gingivalis* (gingipains) using peptidyl chloromethanes", *Biol. Chem.*, 378, 223-230, 1997.

Quirynen, M., et al., "Initial subgingival colonization of 'pristine' pockets", *J. Dent. Res.*, 84, 340-344, 2005.

Rajapakse, P.S., et al., "Immunization with the RgpA-Kgp proteinase-adhesin complexes of *Porphyromonas gingivalis* protects against periodontal bone loss in the rat periodontitis model", *Infect. Immun.*, 70, 2480-2486, 2002.

Rosen, G., et al., "Coaggregation of *Porphyromonas gingivalis* and *Fusobacterium nucleatum* PK 1594 is mediated by capsular polysaccharide and lipopolysaccharide", *FEMS Microbiol Lett.*, 256, 304-310, 2006.

Sainz, B, Jr., et al., "Inhibition of severe acute respiratory syndrome-associated coronavirus (SARS-CoV) infectivity by peptides analogous to the viral spike protein", *Virus Res.*, 120, 146-155, pp. 1-18, 2006.

Sansom, M.S., "Proline residues in transmembrane helices of channel and transport proteins: a molecular modelling study", *Protein Engineering*, 5, 53-60, 1992.

Savkur, R.S., et al., "The coactivator LXXLL nuclear receptor recognition motif", *J. Peptide Res.*, 63, 207-212, 2004.

Scannapieco, F.A., "Saliva-Bacterium Interactions in Oral Microbial Ecology", *Critical Reviews in Oral Biology and Medicine*, 5(3&4), pp. 203-248, 1994.

Scannapieco, F.A., et al., "Emergence of human dental plaque and host distribution of amylase-binding streptococci", *J. Dent. Res.*, 73, 1627-1635, 1994.

Sheets, S.M., et al., "Gingipains from *Porphyromonas gingivalis* W83 induce cell adhesion molecule cleavage and apoptosis in endothelial cells", *Infect. Immun.*, 73, 1543-1552, 2005.

Shi, Y., et al., "Genetic analyses of proteolysis, hemoglobin binding, and hemagglutination of *Porphyromonas gingivalis*. Construction of mutants with a combination of rgpA, rgpB, kgp, and hagA.", *J. Biol. Chem.*, 274, 17955-17960, 1999.

Simionato, M.R., et al., "*Porphyromonas gingivalis* genes involved in community development with *Streptococcus gordonii*", *Infect. Immun.*, 74, 6419-6428, 2006.

Socransky, S.S. et al., "Microbial complexes in subgingival plaque", *J. Clin. Periodontol.*, 25, 134-144, 1998.

Srinivasan, M., et al., "A retro-inverso peptide mimic of CD28 encompassing the MYPPPY motif adopts a polyproline type II helix and inhibits encephalitogenic T cells in vitro", *J. Immunol.*, 167, 578-585, 2001.

Takahashi, N. et al., "Metabolic pathways for cytotoxic end product formation from glutamate- and aspartate-containing peptides by *Porphyromonas gingivalis*", *J. Bacteriol.*, 182, 4704-4710, 2000.

Van De Wijngaart, D.J., et al., "Novel FXXFF and FXXMF motifs in androgen receptor cofactors mediate high affinity and specific interactions with the ligand-binding domain", *J. Biol. Chem.*, 281, 19407-19416, 2006.

Watanabe, K., et al., "Correlation between cell-adherent activity and surface structure in *Porphyromonas gingivalis*", *Oral Microbiol. Immunol.*, 7, 357-363, 1992.

Wirth, R., et al., "Highly efficient protoplast transformation system for *Streptococcus faecalis* and a new *Escherichia coli-S. faecalis* shuttle vector", *J. Bacteriol.*, 165, 831-836, 1986.

Ximenez-Fyvie, L.A., et al., "Microbial composition of supra- and subgingival plaque in subjects with adult periodontitis", *J. Clin. Periodontol.*, 27, 722-732, 2000.

Yao, E. S. et al., "Interbacterial binding among strains of pathogenic and commensal oral bacterial species", *Oral Microbiol. Immunol.*, 11, 35-41, 1996.

Yoshimura, F. et al., "Characterization of a trypsin-like protease from the bacterium *Bacteroides gingivalis* isolated from human dental plaque", *Arch. Oral Biol.*, 29, 559-564, 1984.

Zhang, Y., et al., "Differential protein expression by *Porphyromonas gingivalis* in response to secreted epithelial cell components", *Proteomics*, 5, 198-211, pp. 1-22, 2005.

\* cited by examiner

Figure 1

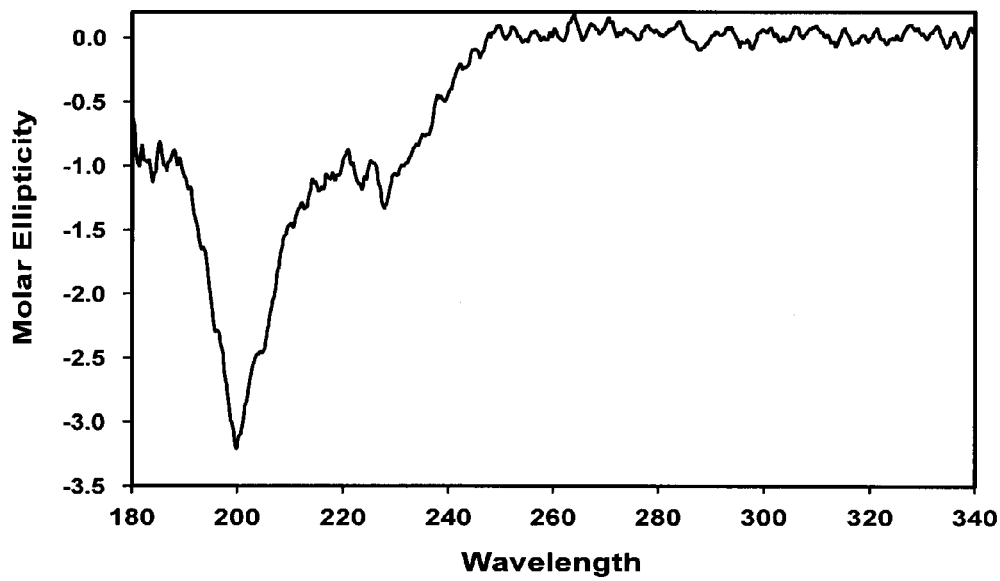

Figure 2

BAR leaapkkvqdllkkaNITVKgafqlfs (SEQ ID NO: 15)

a) leaapkkvqdllkkaRITIKgafqlfs (SEQ ID NO: 17)
b) leaapkkvqdllkkaRITFKgafqlfs (SEQ ID NO: 18)
c) leaapkkvqdllkkaSITIKgafqlfs (SEQ ID NO: 19)
d) leaapkkvqdllkkaSITFKgafqlfs (SEQ ID NO: 20)

Figure 3

|     | abcdefgabcdefga |     |
| --- | --- | --- |
| BAR | leaapkkVQDLLkkaNITVKgafqlfs | (SEQ ID NO: 15) |
| a)  | CleaapkkVQDLLkkaNITVKgafqlfsC | (SEQ ID NO: 21) |
| b)  | CkkVQDLLkkaNITVKC | (SEQ ID NO: 22) |
| c)  | LeaaOkkVCDLLkkaNITVKgafqlfs | (SEQ ID NO: 23) |
| d)  | OkkVCDLLkkaNITVK | (SEQ ID NO: 24) |
| e)  | CNITVKC | (SEQ ID NO: 25) |

Figure 4

| Peptide | Description | Peptide Sequence[1] |
|---|---|---|
| BAR | native SspB sequence | NH2-LEAAPKKVQDLLKKANITVKGAFQLFS-OH (SEQ ID NO:15) |
| BAR-II | BAR with Arg/Asn[1182] and Ile/Val[1185] substitutions | NH2-LEAAPKKVQDLLKKARITIKGAFQLFS-OH (SEQ ID NO:17) |
| BAR-III[2] | conformationally constrained BAR | NH2-LEAAPKKVQDCLKKANITVKGAFQCFS-OH (SEQ ID NO:26) |
| BAR-IV | decapeptide containing only VQDLL of BAR | NH2-PKKVQDLLKK-OH (SEQ ID NO:27) |
| BAR-V | decapeptide containing only NITVK of BAR | NH2-ANITVKGAFQ-OH (SEQ ID NO:28) |
| BAR-VI | decamer from *S. mutans* antigen I/II corresponding to BAR-V | NH2-AGIRPKGAFQ-OH (SEQ ID NO:29) |
| BAR-VII | 20-mer containing VXXLL and NITVK | NH2-PKKVQDLLKKANITVKGAFQ-OH (SEQ ID NO:30) |
| BAR-VIII | 20-mer from *S. mutans* antigen I/II corresponding to BAR-VII | NH2-PQEIRDVLSKAGIRPKGAFQ-OH (SEQ ID NO:31) |
| BAR-IX | BAR with Asp/Val[1174], Asn/Leu[1177] and Asp/Leu[1178] substitutions | NH2-LEAAPKKDQDNDKKANITVKGAFQLFS-OH (SEQ ID NO:32) |
| BAR-X | BAR with Pro/Gln[1175] and Gly/Asp[1176] substitutions | NH2-LEAAPKKVPGLLKKANITVKGAFQLFS-OH (SEQ ID NO:33) |
| BAR-XI | BAR with Asp substitutions at Lys[1172,1173,1179,1180] | NH2-LEAAPDDVQDLLDDANITVKGAFQLFS-OH (SEQ ID NO:34) |

1 - The underlined sequence(s) in each peptide represents the structural motif(s) involved in its interaction with *P. gingivalis*, or the corresponding sequences derived from control antigen I/II proteins that do not interact with *P. gingivalis*.

2 - Note that Cys[1177] replaces a Leucine residue in VXXLL

Figure 5

| Peptide (μM) | BAR | | | | R$^{1182}$T$^{1185}$-BAR | | | |
|---|---|---|---|---|---|---|---|---|
| | Colonies | Frames | Colonies/Frame +/- SEM | % Inhibition | Colonies | Frames | Colonies/Frame +/- SEM | % Inhibition |
| 0 | 128 | 30 | 4.27 ± 0.59 | 0 | 128 | 30 | 4.27 ± 0.59 | 0 |
| 0.169 | 142 | 33 | 4.3 ± 0.89 | 0 | 125 | 31 | 4.03 ± 0.5 | 5.49 |
| 0.338 | 198 | 48 | 4.13 ± 0.43 | 3.32 | 99 | 31 | 3.19 ± 0.46 | 25.15 |
| 0.845 | 127 | 32 | 3.97 ± 0.69 | 6.98 | 23 | 30 | 0.77 ± 0.17$^{a,b}$ | 82.03 |
| 1.69 | 30 | 34 | 0.88 ± 0.25$^a$ | 79.3 | 13 | 30 | 0.43 ± 0.22$^a$ | 89.84 |
| 3.38 | 47 | 51 | 0.92 ± 0.26$^a$ | 78.4 | 11 | 30 | 0.37 ± 0.16$^a$ | 91.46 | a - $p \leq 0.001$ when compared with the control (0 μM test peptide).

b - $p \leq 0.001$ when compared with 3.38 μM BAR peptide inhibited P. gingivalis

Figure 6

| Peptide | Predicted[1] | CD spectroscopy | | |
|---|---|---|---|---|
| | | α-helix | β-sheet | random |
| BAR | HHHHHHHHHHHHCCCCCCCEEEEE<br>LEAAPKKVQDLLKKANITVKGAFQLFS (SEQ ID NO: 15) | 10 | 40 | 50 |
| BAR-II | HHHHHHHHHHHHCCCCCCCEEEEE<br>LEAAPKKVQDLLKKARITIKGAFQLFS (SEQ ID NO: 17) | 28 | 31 | 41 |
| BAR-III | N/D | 28 | 33 | 39 |

1 – Structural predictions were carried out using the Protein Structure Prediction Server (Psipred, on the world-wide-web at bioinf.cs.ucl.ac.uk). H, α-helix, E, β-sheet, C, random.

Figure 9

| Protein | Organism | Sequence |
|---|---|---|
| SspB | S. gordonii | LEAAP KKVQDLLKK A NITVK GAFQLFS (SEQ ID NO: 35) |
| SspA | | LEAAP KKVQDLLKK A NITVK GAFQLFS (SEQ ID NO: 36) |
| AgI/II | S. oralis | LERAP KKVQDLLKK A NITVK GAFQLFS (SEQ ID NO: 37) |
| SspC | S. sanguinis | LETAP AAVRELLQK A NITVK GSFQFFA (SEQ ID NO: 38) |
| AgI/II | S. downei | LEAAP AAVQDMLKK A NITPK GAFQVFT (SEQ ID NO: 39) |
| SpaA | S. sobrinus | LEAAP AAVQDMLKK A NITPK GAFQVFT (SEQ ID NO: 40) |
| PaaA | S. criceti | LEAAP EMVREMLQK A NITPK GAFQLFT (SEQ ID NO: 41) |
| Pas | S. intermedius | LEAAP QEVRDVLSK A GIRPK GAFQIFR (SEQ ID NO: 42) |
| SpaP | S. mutans | LEAAP QEIRDVLSK A GIRPK GAFQIFR (SEQ ID NO: 43) |
| Sr | | LKQPL KKLEMFFLR A GIRLK GAFQIFR (SEQ ID NO: 44) |
| AgI/II hypothetical | S. agalactiae | LNEAP KDLQDLLAR A KITPT GAFQVFE (SEQ ID NO: 45) |
| | | LDKAP KELQDKLAR A NISPK GAFQVFE (SEQ ID NO: 46) |
| AgI/II | S. suis | LNEAP KDLQDKLAR A KITPT GAFQVFL (SEQ ID NO: 47) |
| CluA | L. lactis | VKDAP AEVQKVLAD A KIAPK GQFVFYS (SEQ ID NO: 48) |
| Putative | S. pyogenes | QDTLD DKLKALIKA S GISPV GEFYMWV (SEQ ID NO: 49) |

Figure 12

| Peptide | Description | Peptide Sequence |
|---|---|---|
| BAR | | LEAAPKKVQDLLKKANITVKGAFQLFS (SEQ ID NO: 15) |
| BAR-II | BAR containing the amino acid substitutions Arg/Asn$^{1182}$ and Ile/Val$^{1185}$ | LEAA*PKKVQDLLKKA**R*IT*IK*GAFQLFS (SEQ ID NO:17) |
| BAR-XII | Conformationally constrained BAR; BAR with | CEAAKKVQDLLKKANITVKGAFQCFS (SEQ ID NO:50) |
| BAR-XIII | BAR with Gln/Pro$^{1171}$ substitution | LEAAQKKVQDLLKKANITVKGAFQLFS (SEQ ID NO:51) |

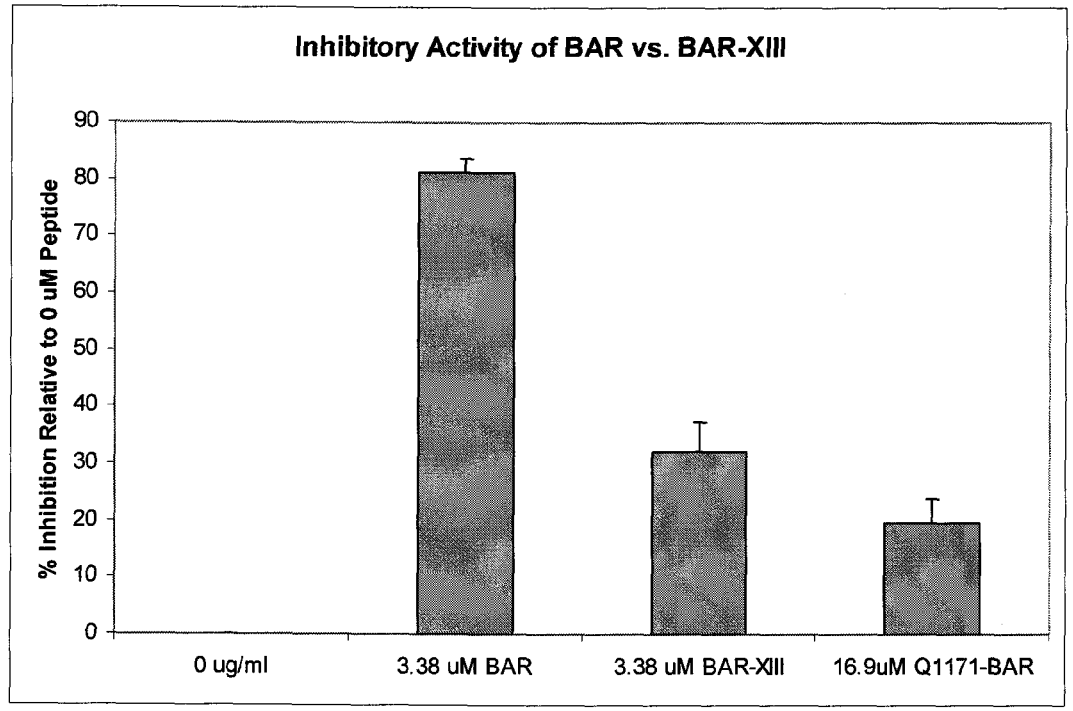

Figure 13

Figure 14. Comparison of the specific inhibitory activity of BAR vs. BAR-XII

| | BAR | | | | BAR-XII | | | |
|---|---|---|---|---|---|---|---|---|
| Peptide (μM) | Colonies | Frames | Colonies/Frame +/- SEM | % Inhibition | Colonies | Frames | Colonies/Frame +/- SEM | % Inhibition |
| 0 | 314 | 49 | 6.16 ± 0.67 | 0 | 314 | 49 | 6.16 ± 0.67 | 0 |
| 0.338 | 96 | 16 | 6 ± 0.7 | 2.54 | 33 | 10 | 3.3 ± 0.45$^{c,\ d}$ | 46.4 |
| 0.845 | 151 | 28 | 5.03 ± 0.66$^a$ | 18.24 | 78 | 30 | 3.19 ± 0.46$^b$ | 25.15 |
| 1.69 | 4 | 10 | 0.4 ± 0.12 | 93.5 | 29 | 39 | 0.74 ± 0.27 | 87.9 | a - P ≤ 0.001 when compared with the control (1.69 μM test peptide).
b - P ≤ 0.05 when compared with 0.845 μM BAR peptide inhibited *P. gingivalis*.
c – P ≤ 0.001 when compared with 1.69 μM BAR peptide inhibited *P. gingivalis*.
d – P ≤ 0.05 when compared 0.845 μM BAR-XII inhibited *P. gingivalis*.

Figure 15.
A)
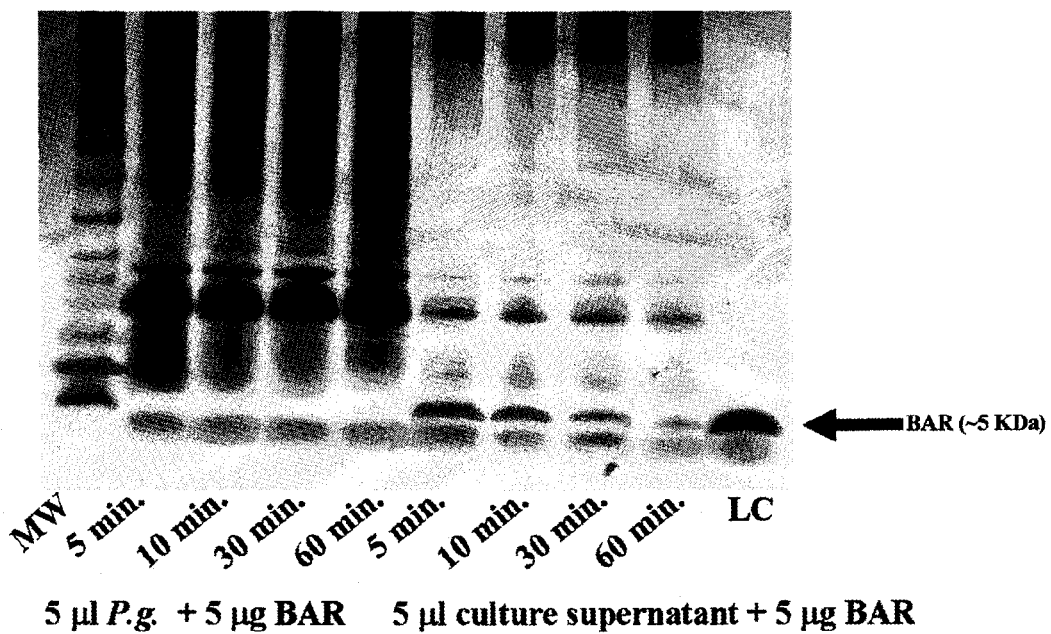
B)
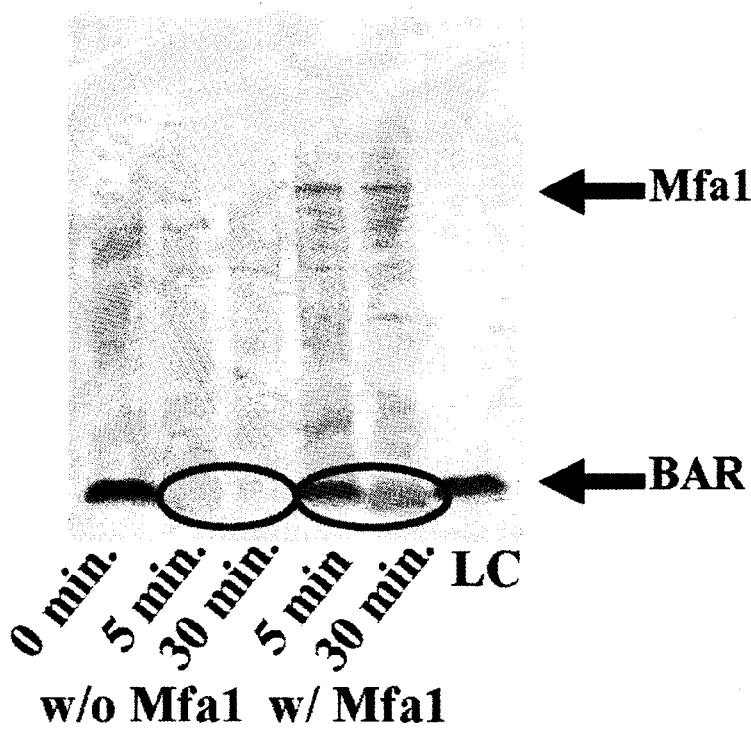

Figure 19.
A) 
B) 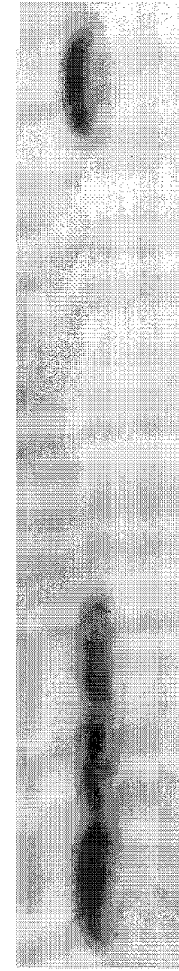
C) 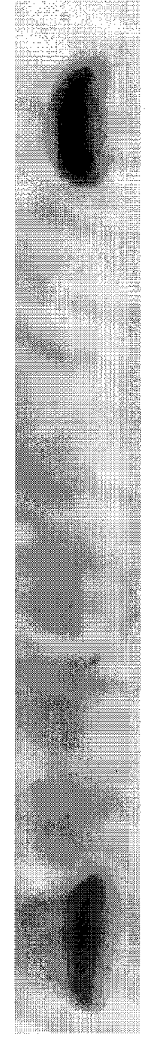

```
                        SEQUENCE LISTING

<160> NUMBER OF SEQ ID NOS: 58

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Gln Asp Leu Leu
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asn Ile Thr Val Lys
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid

<400> SEQUENCE: 3

Val Xaa Xaa Leu Leu
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid

<400> SEQUENCE: 4

Val Xaa Xaa Met Leu
1               5

<210> SEQ ID NO 5
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid

<400> SEQUENCE: 5

Val Xaa Xaa Val Leu
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid

<400> SEQUENCE: 6

Leu Xaa Xaa Leu Leu
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Pro Gly Leu Leu
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid

<400> SEQUENCE: 8

Asp Xaa Xaa Asn Asp
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any hydrophobic amino acid
<220> FEATURE:
<221> NAME/KEY: MOD_RES
```

```
<222> LOCATION: (2)..(3)
<223> OTHER INFORMATION: Any amino acid
<220> FEATURE:
<221> NAME/KEY: MOD_RES
<222> LOCATION: (4)..(5)
<223> OTHER INFORMATION: Any hydrophobic amino acid

<400> SEQUENCE: 9

Xaa Xaa Xaa Xaa Xaa
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ile Thr Ile Lys
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid

<400> SEQUENCE: 11

Phe Xaa Xaa Phe Phe
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: Any amino acid

<400> SEQUENCE: 12

Lys Lys Val Xaa Xaa Leu Leu Lys Lys
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Lys Val Gln Asp Leu Leu Lys Lys
1               5

<210> SEQ ID NO 14
<211> LENGTH: 4
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid

<400> SEQUENCE: 14

Glu Xaa Xaa Pro
1

<210> SEQ ID NO 15
<211> LENGTH: 27
<212> TYPE: PRT
<213> ORGANISM: Streptococcus gordonii

<400> SEQUENCE: 15

Leu Glu Ala Ala Pro Lys Lys Val Gln Asp Leu Leu Lys Lys Ala Asn
1               5                   10                  15

Ile Thr Val Lys Gly Ala Phe Gln Leu Phe Ser
            20                  25

<210> SEQ ID NO 16
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Gln Ala Ala Pro Lys Lys Val Gln Asp Leu Leu Lys Lys Ala Asn
1               5                   10                  15

Ile Thr Val Lys Gly Ala Phe Gln Leu Phe Ser
            20                  25

<210> SEQ ID NO 17
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Glu Ala Ala Pro Lys Lys Val Gln Asp Leu Leu Lys Lys Ala Arg
1               5                   10                  15

Ile Thr Ile Lys Gly Ala Phe Gln Leu Phe Ser
            20                  25

<210> SEQ ID NO 18
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Glu Ala Ala Pro Lys Lys Val Gln Asp Leu Leu Lys Lys Ala Arg
1               5                   10                  15

Ile Thr Phe Lys Gly Ala Phe Gln Leu Phe Ser
            20                  25
```

```
<210> SEQ ID NO 19
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Glu Ala Ala Pro Lys Lys Val Gln Asp Leu Leu Lys Lys Ala Ser
1               5                   10                  15

Ile Thr Ile Lys Gly Ala Phe Gln Leu Phe Ser
            20                  25

<210> SEQ ID NO 20
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Glu Ala Ala Pro Lys Lys Val Gln Asp Leu Leu Lys Lys Ala Ser
1               5                   10                  15

Ile Thr Phe Lys Gly Ala Phe Gln Leu Phe Ser
            20                  25

<210> SEQ ID NO 21
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Cys Leu Glu Ala Ala Pro Lys Lys Val Gln Asp Leu Leu Lys Lys Ala
1               5                   10                  15

Asn Ile Thr Val Lys Gly Ala Phe Gln Leu Phe Ser Cys
            20                  25

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Cys Lys Lys Val Gln Asp Leu Leu Lys Lys Ala Asn Ile Thr Val Lys
1               5                   10                  15

Cys

<210> SEQ ID NO 23
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ornithine

<400> SEQUENCE: 23
```

```
Leu Glu Ala Ala Xaa Lys Lys Val Cys Asp Leu Leu Lys Lys Ala Asn
1               5                   10                  15

Ile Thr Val Lys Gly Ala Phe Gln Leu Phe Ser
            20                  25
```

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine

<400> SEQUENCE: 24

```
Xaa Lys Lys Val Cys Asp Leu Leu Lys Lys Ala Asn Ile Thr Val Lys
1               5                   10                  15
```

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Cys Asn Ile Thr Val Lys Cys
1               5
```

<210> SEQ ID NO 26
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Leu Glu Ala Ala Pro Lys Lys Val Gln Asp Cys Leu Lys Lys Ala Asn
1               5                   10                  15

Ile Thr Val Lys Gly Ala Phe Gln Cys Phe Ser
            20                  25
```

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Pro Lys Lys Val Gln Asp Leu Leu Lys Lys
1               5                   10
```

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Asn Ile Thr Val Lys Gly Ala Phe Gln
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Gly Ile Arg Pro Lys Gly Ala Phe Gln
1               5                   10

<210> SEQ ID NO 30
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Pro Lys Lys Val Gln Asp Leu Leu Lys Lys Ala Asn Ile Thr Val Lys
1               5                   10                  15

Gly Ala Phe Gln
            20

<210> SEQ ID NO 31
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Pro Gln Glu Ile Arg Asp Val Leu Ser Lys Ala Gly Ile Arg Pro Lys
1               5                   10                  15

Gly Ala Phe Gln
            20

<210> SEQ ID NO 32
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Glu Ala Ala Pro Lys Lys Asp Gln Asp Asn Asp Lys Lys Ala Asn
1               5                   10                  15

Ile Thr Val Lys Gly Ala Phe Gln Leu Phe Ser
            20                  25

<210> SEQ ID NO 33
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

-continued

Leu Glu Ala Ala Pro Lys Lys Val Pro Gly Leu Leu Lys Lys Ala Asn
1               5                   10                  15

Ile Thr Val Lys Gly Ala Phe Gln Leu Phe Ser
            20                  25

<210> SEQ ID NO 34
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Leu Glu Ala Ala Pro Asp Asp Val Gln Asp Leu Leu Asp Asp Ala Asn
1               5                   10                  15

Ile Thr Val Lys Gly Ala Phe Gln Leu Phe Ser
            20                  25

<210> SEQ ID NO 35
<211> LENGTH: 27
<212> TYPE: PRT
<213> ORGANISM: Streptococcus gordonii

<400> SEQUENCE: 35

Leu Glu Ala Ala Pro Lys Lys Val Gln Asp Leu Leu Lys Lys Ala Asn
1               5                   10                  15

Ile Thr Val Lys Gly Ala Phe Gln Leu Phe Ser
            20                  25

<210> SEQ ID NO 36
<211> LENGTH: 27
<212> TYPE: PRT
<213> ORGANISM: Streptococcus gordonii

<400> SEQUENCE: 36

Leu Glu Ala Ala Pro Lys Lys Val Gln Asp Leu Leu Lys Lys Ala Asn
1               5                   10                  15

Ile Thr Val Lys Gly Ala Phe Gln Leu Phe Ser
            20                  25

<210> SEQ ID NO 37
<211> LENGTH: 27
<212> TYPE: PRT
<213> ORGANISM: Streptococcus oralis

<400> SEQUENCE: 37

Leu Glu Arg Ala Pro Lys Lys Val Gln Asp Leu Leu Lys Lys Ala Asn
1               5                   10                  15

Ile Thr Val Lys Gly Ala Phe Gln Leu Phe Ser
            20                  25

<210> SEQ ID NO 38
<211> LENGTH: 27
<212> TYPE: PRT
<213> ORGANISM: Streptococcus sanguinis

<400> SEQUENCE: 38

Leu Glu Thr Ala Pro Ala Ala Val Arg Glu Leu Leu Gln Lys Ala Asn
1               5                   10                  15

Ile Thr Val Lys Gly Ser Phe Gln Phe Phe Ala
            20                  25

<210> SEQ ID NO 39
<211> LENGTH: 27
<212> TYPE: PRT
<213> ORGANISM: Streptococcus downei

<400> SEQUENCE: 39

Leu Glu Ala Ala Pro Ala Ala Val Gln Asp Met Leu Lys Lys Ala Asn
1               5                   10                  15

Ile Thr Pro Lys Gly Ala Phe Gln Val Phe Thr
            20                  25

<210> SEQ ID NO 40
<211> LENGTH: 27
<212> TYPE: PRT
<213> ORGANISM: Streptococcus sobrinus

<400> SEQUENCE: 40

Leu Glu Ala Ala Pro Ala Ala Val Gln Asp Met Leu Lys Lys Ala Asn
1               5                   10                  15

Ile Thr Pro Lys Gly Ala Phe Gln Val Phe Thr
            20                  25

<210> SEQ ID NO 41
<211> LENGTH: 27
<212> TYPE: PRT
<213> ORGANISM: Streptococcus criceti

<400> SEQUENCE: 41

Leu Glu Ala Ala Pro Glu Met Val Arg Glu Met Leu Gln Lys Ala Asn
1               5                   10                  15

Ile Thr Pro Lys Gly Ala Phe Gln Leu Phe Thr
            20                  25

<210> SEQ ID NO 42
<211> LENGTH: 27
<212> TYPE: PRT
<213> ORGANISM: Streptococcus intermedius

<400> SEQUENCE: 42

Leu Glu Ala Ala Pro Gln Glu Val Arg Asp Val Leu Ser Lys Ala Gly
1               5                   10                  15

Ile Arg Pro Lys Gly Ala Phe Gln Ile Phe Arg
            20                  25

<210> SEQ ID NO 43
<211> LENGTH: 27
<212> TYPE: PRT
<213> ORGANISM: Streptococcus mutans

<400> SEQUENCE: 43

Leu Glu Ala Ala Pro Gln Glu Ile Arg Asp Val Leu Ser Lys Ala Gly
1               5                   10                  15

Ile Arg Pro Lys Gly Ala Phe Gln Ile Phe Arg
            20                  25

<210> SEQ ID NO 44
<211> LENGTH: 27
<212> TYPE: PRT
<213> ORGANISM: Streptococcus mutans

<400> SEQUENCE: 44

Leu Lys Gln Pro Leu Lys Lys Leu Glu Met Phe Phe Leu Arg Ala Gly
1               5                   10                  15

```
Ile Arg Leu Lys Gly Ala Phe Gln Ile Phe Arg
            20                  25

<210> SEQ ID NO 45
<211> LENGTH: 27
<212> TYPE: PRT
<213> ORGANISM: Streptococcus agalactiae

<400> SEQUENCE: 45

Leu Asn Glu Ala Pro Lys Asp Leu Gln Asp Leu Leu Ala Arg Ala Lys
1               5                   10                  15

Ile Thr Pro Thr Gly Ala Phe Gln Val Phe Glu
            20                  25

<210> SEQ ID NO 46
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Leu Asp Lys Ala Pro Lys Glu Leu Gln Asp Lys Leu Ala Arg Ala Asn
1               5                   10                  15

Ile Ser Pro Lys Gly Ala Phe Gln Val Phe Glu
            20                  25

<210> SEQ ID NO 47
<211> LENGTH: 27
<212> TYPE: PRT
<213> ORGANISM: Streptococcus suis

<400> SEQUENCE: 47

Leu Asn Glu Ala Pro Lys Asp Leu Gln Asp Lys Leu Ala Arg Ala Lys
1               5                   10                  15

Ile Thr Pro Thr Gly Ala Phe Gln Val Phe Leu
            20                  25

<210> SEQ ID NO 48
<211> LENGTH: 27
<212> TYPE: PRT
<213> ORGANISM: Streptococcus lactis

<400> SEQUENCE: 48

Val Lys Asp Ala Pro Ala Glu Val Gln Lys Val Leu Ala Asp Ala Lys
1               5                   10                  15

Ile Ala Pro Lys Gly Gln Phe Val Phe Tyr Ser
            20                  25

<210> SEQ ID NO 49
<211> LENGTH: 27
<212> TYPE: PRT
<213> ORGANISM: Streptococcus pyogenes

<400> SEQUENCE: 49

Gln Asp Thr Leu Asp Asp Lys Leu Lys Ala Leu Ile Lys Ala Ser Gly
1               5                   10                  15

Ile Ser Pro Val Gly Glu Phe Tyr Met Trp Val
            20                  25

<210> SEQ ID NO 50
<211> LENGTH: 27
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 50

Cys Glu Ala Ala Pro Lys Lys Val Gln Asp Leu Leu Lys Lys Ala Asn
1               5                  10                  15

Ile Thr Val Lys Gly Ala Phe Gln Cys Phe Ser
            20                  25

<210> SEQ ID NO 51
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Leu Glu Ala Ala Gln Lys Lys Val Gln Asp Leu Leu Lys Lys Ala Asn
1               5                  10                  15

Ile Thr Val Lys Gly Ala Phe Gln Leu Phe Ser
            20                  25

<210> SEQ ID NO 52
<211> LENGTH: 27
<212> TYPE: PRT
<213> ORGANISM: Streptococcus gordonii

<400> SEQUENCE: 52

Leu Glu Ala Ala Pro Lys Lys Val Gln Asp Leu Leu Lys Lys Ala Asn
1               5                  10                  15

Ile Thr Val Lys Gly Ala Phe Gln Leu Phe Ser
            20                  25

<210> SEQ ID NO 53
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Cys or Absent
<220> FEATURE:
<221> NAME/KEY: MOD_RES
<222> LOCATION: (2)..(4)
<223> OTHER INFORMATION: Any amino acid other than Gly or Pro
<220> FEATURE:
<221> NAME/KEY: MOD_RES
<222> LOCATION: (5)..(5)
<223> OTHER INFORMATION: May or may not be present
<220> FEATURE:
<221> NAME/KEY: MOD_RES
<222> LOCATION: (6)..(6)
<223> OTHER INFORMATION: Cys or Ornithine; may or may not be present
<220> FEATURE:
<221> NAME/KEY: MOD_RES
<222> LOCATION: (8)..(9)
<223> OTHER INFORMATION: May or may not be present
<220> FEATURE:
<221> NAME/KEY: MOD_RES
<222> LOCATION: (11)..(12)
<223> OTHER INFORMATION: Any amino acid except Pro
<220> FEATURE:
<221> NAME/KEY: MOD_RES
<222> LOCATION: (16)..(17)
<223> OTHER INFORMATION: May or may not be present
```

```
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (19)..(27)
<223> OTHER INFORMATION: Any amino acid; may or may not be present
<220> FEATURE:
<221> NAME/KEY: MOD_RES
<222> LOCATION: (28)..(28)
<223> OTHER INFORMATION: Any amino acid except Asp, Glu, Gly or Pro
<220> FEATURE:
<221> NAME/KEY: MOD_RES
<222> LOCATION: (30)..(30)
<223> OTHER INFORMATION: Any amino acid except Ala, Asp, Gly, His, Ile,
      Pro, Trp or Tyr
<220> FEATURE:
<221> NAME/KEY: MOD_RES
<222> LOCATION: (31)..(31)
<223> OTHER INFORMATION: Val, Ile, Phe or Trp
<220> FEATURE:
<221> NAME/KEY: MOD_RES
<222> LOCATION: (33)..(38)
<223> OTHER INFORMATION: May or may not be present
<220> FEATURE:
<223> OTHER INFORMATION: see specification as filed for detailed
      description of substitutions and preferred embodiments

<400> SEQUENCE: 53

Cys Xaa Xaa Xaa Pro Xaa Lys Lys Lys Val Xaa Xaa Leu Leu Lys Lys
1               5                   10                  15

Lys Xaa Xaa Xaa Xaa Xaa Xaa Xaa Xaa Xaa Xaa Xaa Ile Xaa Xaa Lys
            20                  25                  30

Cys Gly Ala Phe Gln Cys
        35

<210> SEQ ID NO 54
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (3)..(4)
<223> OTHER INFORMATION: May or may not be present
<220> FEATURE:
<221> NAME/KEY: MOD_RES
<222> LOCATION: (6)..(7)
<223> OTHER INFORMATION: Any amino acid except Pro
<220> FEATURE:
<221> NAME/KEY: MOD_RES
<222> LOCATION: (11)..(12)
<223> OTHER INFORMATION: May or may not be present
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (14)..(22)
<223> OTHER INFORMATION: Any amino acid; may or may not be present
<220> FEATURE:
<221> NAME/KEY: MOD_RES
<222> LOCATION: (23)..(23)
<223> OTHER INFORMATION: Any amino acid except Asp, Glu, Gly or Pro
<220> FEATURE:
<221> NAME/KEY: MOD_RES
<222> LOCATION: (25)..(25)
<223> OTHER INFORMATION: Any amino acid except Ala, Asp, Gly, His, Ile,
```

-continued

```
            Pro, Trp or Tyr
<220> FEATURE:
<221> NAME/KEY: MOD_RES
<222> LOCATION: (26)..(26)
<223> OTHER INFORMATION: Val, Phe, Ile or Trp
<220> FEATURE:
<221> NAME/KEY: MOD_RES
<222> LOCATION: (28)..(28)
<223> OTHER INFORMATION: May or may not be present
<220> FEATURE:
<223> OTHER INFORMATION: see specification as filed for detailed
      description of substitutions and preferred embodiments

<400> SEQUENCE: 54

Cys Lys Lys Lys Val Xaa Xaa Leu Leu Lys Lys Xaa Xaa Xaa Xaa
1               5                   10                  15

Xaa Xaa Xaa Xaa Xaa Xaa Xaa Ile Xaa Xaa Lys Cys
                20                  25

<210> SEQ ID NO 55
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (2)..(4)
<223> OTHER INFORMATION: Any amino acid except Gly or Pro; may or may
      not be present
<220> FEATURE:
<221> NAME/KEY: MOD_RES
<222> LOCATION: (6)..(6)
<223> OTHER INFORMATION: May or may not be present
<220> FEATURE:
<221> NAME/KEY: MOD_RES
<222> LOCATION: (8)..(9)
<223> OTHER INFORMATION: May or may not be present
<220> FEATURE:
<221> NAME/KEY: MOD_RES
<222> LOCATION: (11)..(12)
<223> OTHER INFORMATION: Any amino acid except Pro
<220> FEATURE:
<221> NAME/KEY: MOD_RES
<222> LOCATION: (16)..(17)
<223> OTHER INFORMATION: May or may not be present
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (19)..(27)
<223> OTHER INFORMATION: Any amino acid; may or may not be present
<220> FEATURE:
<221> NAME/KEY: MOD_RES
<222> LOCATION: (28)..(28)
<223> OTHER INFORMATION: Any amino acid except Asp, Glu, Gly or Pro
<220> FEATURE:
<221> NAME/KEY: MOD_RES
<222> LOCATION: (30)..(30)
<223> OTHER INFORMATION: Any amino acid except Ala, Asp, His, Ile, Pro,
      Trp or Tyr
<220> FEATURE:
<221> NAME/KEY: MOD_RES
<222> LOCATION: (31)..(31)
<223> OTHER INFORMATION: Val, Ile, Phe or Trp
<220> FEATURE:
<221> NAME/KEY: MOD_RES
<222> LOCATION: (33)..(33)
<223> OTHER INFORMATION: May or may not be present
<220> FEATURE:
```

-continued

```
<223> OTHER INFORMATION: see specification as filed for detailed
      description of substitutions and preferred embodiments

<400> SEQUENCE: 55

Cys Xaa Xaa Xaa Pro Cys Lys Lys Val Xaa Xaa Leu Leu Lys Lys
1               5                   10                  15

Lys Xaa Xaa Xaa Xaa Xaa Xaa Xaa Xaa Xaa Xaa Ile Xaa Xaa Lys
            20                  25                  30

Cys

<210> SEQ ID NO 56
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (2)..(4)
<223> OTHER INFORMATION: Any amino acid except Gly or Pro; may or may
      not be present
<220> FEATURE:
<221> NAME/KEY: MOD_RES
<222> LOCATION: (6)..(6)
<223> OTHER INFORMATION: May or may not be present
<220> FEATURE:
<221> NAME/KEY: MOD_RES
<222> LOCATION: (8)..(9)
<223> OTHER INFORMATION: May or may not be present
<220> FEATURE:
<221> NAME/KEY: MOD_RES
<222> LOCATION: (11)..(12)
<223> OTHER INFORMATION: Any amino acid except Pro
<220> FEATURE:
<221> NAME/KEY: MOD_RES
<222> LOCATION: (16)..(17)
<223> OTHER INFORMATION: May or may not be present
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (19)..(27)
<223> OTHER INFORMATION: Any amino acid; may or may not be present
<220> FEATURE:
<221> NAME/KEY: MOD_RES
<222> LOCATION: (28)..(28)
<223> OTHER INFORMATION: Any amino acid except Asp, Glu, Gly or Pro
<220> FEATURE:
<221> NAME/KEY: MOD_RES
<222> LOCATION: (30)..(30)
<223> OTHER INFORMATION: Any amino acid except Ala, Asp, Gly, His, Ile,
      Pro, Trp or Tyr
<220> FEATURE:
<221> NAME/KEY: MOD_RES
<222> LOCATION: (31)..(31)
<223> OTHER INFORMATION: Val, Ile, Phe or Trp
<220> FEATURE:
<221> NAME/KEY: MOD_RES
<222> LOCATION: (33)..(38)
<223> OTHER INFORMATION: May or may not be present
<220> FEATURE:
<223> OTHER INFORMATION: see specification as filed for detailed
      description of substitutions and preferred embodiments

<400> SEQUENCE: 56

Cys Xaa Xaa Xaa Pro Cys Lys Lys Val Xaa Xaa Leu Leu Lys Lys
1               5                   10                  15
```

```
Lys Xaa Xaa Xaa Xaa Xaa Xaa Xaa Xaa Xaa Xaa Xaa Ile Xaa Xaa Lys
        20                  25                  30

Cys Gly Ala Phe Gln Cys
        35
```

<210> SEQ ID NO 57
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ornithine; may or may not be present
<220> FEATURE:
<221> NAME/KEY: MOD_RES
<222> LOCATION: (2)..(2)
<223> OTHER INFORMATION: May or may not be present
<220> FEATURE:
<221> NAME/KEY: MOD_RES
<222> LOCATION: (4)..(5)
<223> OTHER INFORMATION: May or may not be present
<220> FEATURE:
<221> NAME/KEY: MOD_RES
<222> LOCATION: (7)..(8)
<223> OTHER INFORMATION: Any amino acid except Pro
<220> FEATURE:
<221> NAME/KEY: MOD_RES
<222> LOCATION: (12)..(13)
<223> OTHER INFORMATION: May or may not be present
<220> FEATURE:
<221> NAME/KEY: MOD_RES
<222> LOCATION: (14)..(14)
<223> OTHER INFORMATION: Any amino acid or absent
<220> FEATURE:
<221> NAME/KEY: MOD_RES
<222> LOCATION: (15)..(23)
<223> OTHER INFORMATION: Any amino acid; may or may not be present
<220> FEATURE:
<221> NAME/KEY: MOD_RES
<222> LOCATION: (24)..(24)
<223> OTHER INFORMATION: Any amino acid except Asp, Glu, Gly or Pro
<220> FEATURE:
<221> NAME/KEY: MOD_RES
<222> LOCATION: (26)..(26)
<223> OTHER INFORMATION: Any amino acid except Ala, Asp, Gly, His, Ile,
      Pro, Trp or Tyr
<220> FEATURE:
<221> NAME/KEY: MOD_RES
<222> LOCATION: (27)..(27)
<223> OTHER INFORMATION: Val, Ile, Phe or Trp
<220> FEATURE:
<221> NAME/KEY: MOD_RES
<222> LOCATION: (29)..(34)
<223> OTHER INFORMATION: May or may not be present
<220> FEATURE:
<223> OTHER INFORMATION: see specification as filed for detailed
      description of substitutions and preferred embodiments

<400> SEQUENCE: 57

```
Xaa Cys Lys Lys Lys Val Xaa Xaa Leu Leu Lys Lys Xaa Xaa Xaa
1               5                   10                  15

Xaa Xaa Xaa Xaa Xaa Xaa Xaa Xaa Ile Xaa Xaa Lys Cys Gly Ala Phe
        20                  25                  30

Gln Cys
```

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic 5xHis tag

<400> SEQUENCE: 58

His His His His His
1               5

SYNTHETIC BIOFILM-INHIBITING PEPTIDES

RELATED APPLICATIONS

This patent document claims the benefit of priority of U.S. Application Ser. Nos. 61/031,934, filed Feb. 27, 2008, and 61/127,797, filed May 14, 2008 which applications are herein incorporated by reference.

GOVERNMENT FUNDING

The invention described herein was made with government support under Grant Number RO1DE12505 awarded by NIDCR. The United States Government has certain rights in this invention.

BACKGROUND OF THE INVENTION

Adult periodontitis is associated with elevated levels of several Gram negative organisms in the subgingival oral biofilm, including the asaccharolytic, obligate anaerobe *Porphyromonas gingivalis*. In this primary niche, *P. gingivalis* interacts with a variety of other Gram negative obligate and facultative anaerobes, such as *Fusobacterium nucleatum*, *Treponema denticola*, and *Tannerella forsythus* through specific receptor-ligand interactions. However, the initial colonization of the oral cavity by *P. gingivalis* likely occurs through adherence to organisms in the supragingival biofilm and the successful colonization of this niche by *P. gingivalis* is contingent upon a variety of factors such as reduced oxygen tension and sufficient nutritional sources. Consistent with this, *P. gingivalis* has been shown to also adhere to organisms in supragingival plaque that may provide it with physiologic support, such as *Streptococcus gordonii* and *F. nucleatum*.

SUMMARY OF THE INVENTION

The present invention provides therapies to treat or prevent the onset of periodontal disease, one of the most common bacterial infections of humans (~35% of the adult population worldwide exhibits symptoms of periodontal disease). Because the target for the inhibiting peptide is the adherence of *P. gingivalis* to supragingival plaque, it is effective in mouth rinses and toothpaste formulations. Such formulations are easily and non-invasively administered by dental practitioners during routine office visits, or are developed into consumer products for home use. *P. gingivalis* gains systemic exposure through damage to gingival tissues. Therefore, limiting the *P. gingivalis* adherence to supragingival plaque in the oral cavity has a dramatic effect on systemic diseases that are associated with the organism, such as atherosclerosis and heart disease.

Current treatment for periodontitis involves removal of all bacteria from the subgingival pockets. Removal of subgingival plaque by current treatment methods is temporary, since the subgingival packet may be re-colonized after cleaning by organisms from the supragingival reservoir. The present technology is specific for the pathogenic organism and will likely not influence the benign or helpful organisms that inhabit the oral cavity. There are currently no pathogen specific treatments available for oral diseases such as periodontal disease. The present technology provides long term control of *P. gingivalis* populations in the oral cavity because it prevents the initial formation of *P. gingivalis* biofilms, as well as disrupting pre-existing biofilms. It is formulated in a way to allow daily exposure allowing it to target organisms in the reservoir in supragingival plaque.

The present invention provides a peptide of Formula I (SEQ ID NO: 53):

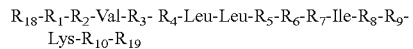

wherein $R_1$ is 0-1 Cys or ornithine residue;
$R_2$ is 1-3 Lys residues;
$R_3$ is any amino acid residue except a Pro residue;
$R_4$ is any amino acid residue except a Pro residue;
$R_5$ is 1-3 Lys residues;
$R_6$ is 1-10 amino acid residues;
$R_7$ is any amino acid except Asp, Glu, Gly or Pro;
$R_8$ is any amino acid residue except Ala, Asp, Gly, His, Ile, Pro, Trp or Tyr;
$R_9$ is a Val, Ile, Phe, or Trp residue;
$R_{10}$ is 0-1 Cys residue;
$R_{18}$ is 0 amino acids or $R_{12}$-$R_{11}$-Pro-,
  wherein $R_{11}$ is 0-3 amino acids, wherein the amino acid residues are not Gly or Pro; and
  $R_{12}$ is 0-1 Cys residues; and
$R_{19}$ is -$R_{13}$-$R_{14}$-$R_{15}$-$R_{16}$-$R_{17}$,
  wherein $R_{13}$ is 0-1 is Gly residue;
  $R_{14}$ is 0-1 Ala residue;
  $R_{15}$ is 0-1 Phe residue;
  $R_{16}$ is 0-1 Gln residue; and
  $R_{17}$ is 0-1 Cys residue.

In certain embodiments, the peptide of any of Formula I has greater structural constraint than native SspB Adherence Region (BAR). In certain embodiments, the peptide contains an unnatural (also called an "artificial") amino acid residue.

The present invention provides a composition including the peptide of Formula I and a physiologically acceptable carrier. In certain embodiments, the carrier is a mouth rinse, toothpaste, dental floss or chewing gum. In certain embodiments, the carrier is a polymer. In certain embodiments, the peptide forms an alpha-helix. In certain embodiments, the composition further contains a protease inhibitor.

The present invention provides a therapeutic method for preventing or treating a pathological condition or symptom in a mammal, such as a human, wherein an antibiotic activity is implicated and antagonism of its action is desired, by administering to a mammal in need of such therapy, an effective amount of a compound of Formula I.

The present invention provides a therapeutic method for preventing or treating a pathological condition or symptom in a mammal, such as a human, wherein anti-biofilm formation activity is implicated and antagonism of its action is desired, comprising administering to a mammal in need of such therapy, an effective amount of a compound of Formula I.

The present invention provides a method to treat a microbial infection comprising administering a therapeutically effective amount of a compound of Formula I to a mammal. In certain embodiments, the bacteria are gram-negative bacteria, such as, for example, *Porphyromonas gingivalis*.

The present invention provides a compound of Formula I for use in medical therapy.

The present invention provides the use of a compound of Formula I for the manufacture of a medicament useful for the treatment of a microbial infection in a mammal.

The present invention provides a method of preventing the adhesion of bacteria on a solid substrate comprising contacting the solid substrate with a peptide of Formula I. In certain embodiments, the peptide is dispersed in a polymer.

The present invention provides a method of preventing the formation of a biofilm of bacteria on a solid substrate comprising contacting the solid substrate with a peptide of Formula I.

The present invention provides a method of preventing the formation of a biofilm of bacteria in vivo comprising contacting a tissue surface with a peptide of Formula I. In certain embodiments, the tissue is oral or lung tissue. In certain embodiments, the tissue is a mucosal surface. In certain embodiments, the bacteria are gram-negative bacteria, such as, for example, Porphyromonas gingivalis.

The present invention provides an isolated or purified nucleic acid that is less than 150 nucleotides in length encoding a peptide of Formula I. In certain embodiments, the isolated or purified nucleic acid is less than 120 nucleotides in length.

The present invention provides an expression cassette containing the nucleic acid encoding a peptide of Formula I. In certain embodiments, the expression cassette further comprises a promoter.

The present invention provides a vector containing the expression cassette containing the nucleic acid encoding a peptide of Formula I.

The present invention provides a cell comprising the expression cassette containing the nucleic acid encoding a peptide of Formula I.

The present invention provides a method of screening a BAR peptide mimetic by selecting organic molecules and comparing its biological activity to that of a peptide of Formula I in standard antimicrobial assays.

BRIEF DESCRIPTION OF THE FIGURES

FIG. 1. CD spectra of BAR peptide. Peptide was suspended in phosphate buffer at a concentration of 1.4 mM.

FIG. 2. Peptide sequences of BAR analogs based on results of the screening of the combinatorial BAR peptide library.

FIG. 3. Peptide sequences of potential constrained BAR analogs. The seven residue periodicity of the predicted α-helix is shown in italics above the amino acid sequences.

FIG. 4. Synthetic peptides. VQDLL, NITVK, and VXXLL disclosed as SEQ ID NOS: 1-3, respectively.

FIG. 5. Comparison of the specific inhibitory activity of BAR v. $R^{1182}I^{1185}$-BAR.

FIG. 6. Secondary structural analysis of BAR peptides.

FIG. 7A Peptides of twenty amino acids that contain the VQDLL (SEQ ID NO:1) and NITVK (SEQ ID NO:2) motifs of BAR (BAR-VII) or the corresponding regions from the antigen I/II protein of S. mutans (BAR-VIII) were incubated with P. gingivalis cells and inoculated onto adherent streptococci. The resulting biofilms were visualized by confocal laser scanning microscopy and analyzed as described in Example 2. A statistically significant difference (*) in microcolony number (P<0.001) was observed when a pair-wise comparison of specific inhibitory activity was compared for BAR-VII, BAR-VIII, and untreated cells. FIG. 7B Decapeptides containing either the VQDLL (SEQ ID NO: 1) or NITVK (SEQ ID NO: 2) motifs of BAR (BAR-IV and BAR-V, respectively), or the control peptide comprising the region corresponding to NITVK (SEQ ID NO: 2) in the antigen I/II protein of S. mutans (BAR-VI) did not inhibit the formation of P. gingivalis biofilms, even P. gingivalis cells was treated with the peptides at a concentration of 16.9 μM.

FIG. 9. Comparison of the BAR region sequences in antigen I/II-related polypeptides of streptococci and lactococci. The VXXLL (SEQ ID NO: 3) and NITVK (SEQ ID NO: 2) motifs are conserved only in S. gordonii, S. oralis and S. sanguinis (blue and yellow boxes, respectively). Sequences corresponding to NITVK (SEQ ID NO: 2) are also present in the antigen I/II of the other organisms but contain amino acid substitutions that are incompatible with P. gingivalis adherence. NR box-like motifs similar to VXXLL (SEQ ID NO: 3) and containing hydrophobic residues at the +1, +4, and +5 positions occur in most of the other antigen I/II sequences. A VXXML (SEQ ID NO: 4) motif is conserved in antigen I/II of S. downei, S. sobrinus and S. criceti and VXXVL (SEQ ID NO: 5) is present in S. intermedius and L. lactis. Furthermore, these NR box-like motifs are flanked by charged amino acid residues. In all antigen I/II sequences with the exception of S. pyogenes, proline and alanine residues occupy positions -3 and +8, respectively, where +1 represents the first hydrophobic residue in the NR box-like motif. A consensus sequence of the BAR region of antigen I/II is shown on the last line. The consensus residues shown were present in at least 8 of the 14 antigen I/II sequences analyzed.

FIG. 12. Peptide sequences and secondary structure predictions using DISTILL software from University College Dublin (on the world-wide-web at distill.ucd.ie/distill/). The underlined sequence (s) within each peptide represents the structural motifs which are important its interaction with the bacteria Porphyromonas gingivalis. The italicized amino acids are susceptible to proteolytic cleavage and therefore could be protected from proteolytic attack through the substitution, though not limited to, of D-amino acids and other synthetic amino acid derivatives. Sequences highlighted in bold are predicted to be α-helical using the DISTILL software from University College Dublin (on the world-wide-web at distill.ucd.ie/distill/).

FIG. 13. Inhibition of *P. gingivalis/S. gordonii* biofilm using BAR-XII. An analog of BAR containing a glutamine substitution for proline at position 5 of the peptide sequence resulted in the attenuation of the inhibitory activity of BAR-XIII. A statistically significant difference (a) in microcolony number was observed following a pair-wise comparison between 0 μM peptide and 3.38 μM BAR (P<0.001). Pre-treatment of *P. gingivalis* with BAR-XIII did not result in the inhibition of *P. gingivalis/S. gordonii* biofilm formation. No statistical difference was observed following a pair-wise comparison between 0 μM BAR 3.38 μM BAR-XIII and 16.9 μM BAR-XIII. However, a pair-wise comparison between 3.38 and 16.9 μM BAR-XIII and 3.38 μM BAR showed a significant difference (b, c; P<0.001) in the total microcolony formation. Percent inhibition was calculated as follows: average microcolonies per frame (control)-average microcolonies per frame (experimental)/average microcolonies per frame (control). At least thirty independent frames from separate biofilms were analyzed for each peptide and peptide concentration.

FIG. 14. Constraining structural flexibility of BAR: comparison of BAR vs. BAR-XII inhibitory activity. Substitution of the leucine residues at position +1 and +24 of the BAR peptide sequence with cystiene (BAR-XII) resulted in an increase in the specific inhibitory activity of the peptide compared with BAR.

FIG. 15. Limiting proteolytic degradation of BAR. A) Incubation of the BAR peptide with either whole *P. gingivalis* cells or culture supernatant containing secreted proteases resulted in a time dependent degradation of the peptide. B) Adherence of the BAR with Mfa1, however, provides the peptide protection from proteolytic degradation.

FIG. 19. Binding of BAR with rMfa1 results in protection of the peptide from protease dependent degradation. To assess the role of Mfa1 between BAR and *P. gingivalis* adherence, rMfa1 was added to BAR and *P. gingivalis* SMF1 and co-incubated for 5 and 30 minutes at 37° C. The relative density (R.D.) of the remaining BAR peptide was determined. In comparison with the loading control (L.C; R.D.=61.07), BAR was immediately degraded by the proteases produced by *P. gingivalis* in the absence of rMfa1 while the addition of the recombinant fimbrial protein resulted in the limitation of BAR degradation as observed at timepoints T=5 (R.D.=47.3 vs. −5.75) and 30 minutes (R.D.=8.2 vs. −20.32). This is suggestive that the adherence of Mfa1 to BAR results in the protection of peptide from proteases activity. A) Little degradation was observed after incubation for 10 minutes with *P. gingivalis* KDP128 which lacks both the Lys-X and Arg-X gingipains. B) Little degradation was observed after exposing BAR to *P. gingivalis* KDP129 which lacks only the Lys-X gingipains. C) Strain E8, which lacks the Arg-X specific gingipains but retains the Lys-X gingipains, rapidly degraded BAR.

DETAILED DESCRIPTION

Figure 7:
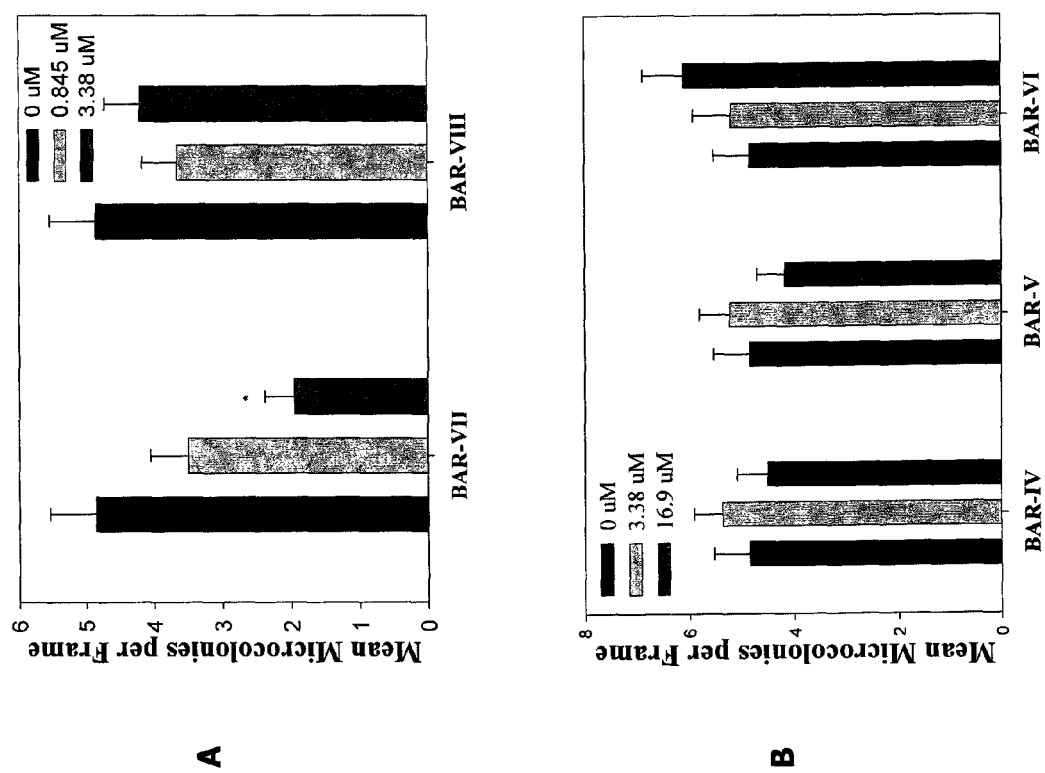
FIG. 7. Inhibition of P. gingivalis/streptococcal biofilm formation by BAR peptide analogs.

*P. gingivalis* is strongly associated with adult periodontitis and is also linked to atherosclerosis, heart disease and preterm births. In the oral cavity, this organism resides in the subgingival pocket and exists in concert with a complex microbial community called a biofilm (dental plaque). However, to reach its primary niche in the subgingival pocket, *P. gingivalis* must first attach to bacterial cells that are present in supragingival dental plaque. *P. gingivalis* colonizes supragingival plaque by adhering to organisms such as *Streptococcus gordonii*. Thus, supragingival plaque may represent a biologic reservoir for *P. gingivalis* in the oral cavity. Because the *P. gingivalis-S. gordonii* interaction represents one of the first reactions that allows *P. gingivalis* to colonize the oral cavity, it is a good target for therapeutic intervention of periodontitis and systemic diseases associated with *P. gingivalis*. Controlling and/or preventing this pathogen from occupying its supragingival niche may limit its access to the preferred subgingival niche that is essential for *P. gingivalis* to exert its pathogenic properties.

Adherence of *P. gingivalis* to *S. gordonii* is mediated by a protein-protein interaction between the fimbrial protein Mfa of *P. gingivalis* and the streptococcal antigen I/II polypeptide. The inventors have dissected this interaction and has identified a specific peptide derived from antigen I/II that binds to Mfa and potently inhibits ($I_{50}$=1.3 µM) the development of *P. gingivalis* biofilms on streptococci. Site specific mutagenesis studies identified a structural motif comprised of the amino acids NITVK (SEQ ID NO: 2) that was essential for biofilm inhibitory activity of the peptide. However, the inventor has now surprisingly shown that this region alone is not sufficient for biofilm inhibition. An unexpected second motif is also required, which includes the amino acids VXXLL (SEQ ID NO: 3), where X is any amino acid. Either motif alone is inactive for inhibition of *P. gingivalis* biofilm formation. A peptide containing both motifs, however, is highly active. In addition, charged amino acids that flank VXXLL (SEQ ID NO: 3) also contribute to biofilm inhibitory activity, suggesting that the association of the VXXLL (SEQ ID NO: 3) motif with Mfa is stabilized by a charge clamp. These observations were unexpected over prior work, which indicated that the active site of the peptide included only of NITVK (SEQ ID NO: 2). Furthermore, the inventors have also shown that a peptide containing both VXXLL (SEQ ID NO: 3) and NITVK (SEQ ID NO: 2) not only prevented the initial formation of *P. gingivalis* biofilms, but also disrupted pre-existing biofilms.

It was quite unexpected that some amino acid substitutions promoted *P. gingivalis* adherence to streptococci. It was also unexpected that a peptide comprising only the active site region of BAR identified in the prior art (i.e., the NITVK (SEQ ID NO: 2) sequence) was found to be inactive. This observation led the inventors to identify the second required region (VXXLL (SEQ ID NO: 3)) and to show that activity requires both VXXLL (SEQ ID NO: 3) and NITVK (SEQ ID NO: 2). Previous work directed one skilled in the art to NITVK (SEQ ID NO: 2). But if that path is followed, the result is an inactive compound. The new and unexpected finding is that two regions are necessary and that a peptide comprising both is fully active. This is distinguishable over the prior work. The present work is also distinguishable over prior work by the data showing that treatment of an existing *P. gingivalis* biofilm with the peptide results in a reduction in biofilm. Prior work only showed that pre-treatment of *P. gingivalis* with the peptide inhibits the formation of a new biofilm and does not address activity against an already formed biofilm. Data and description of this experiment is included in Example 3 below.

The inventors have discovered a third motif that is important for optimal activity, which is a praline residue in BAR. This praline is preceded three residues upstream by a glutamate residue. Without being bound by theory, it is believed that the proline makes a "kink" in the helix. Proline is commonly called a helix breaking amino acid because in general, its structure is not compatible with forming a helical structure. However, one does find proline in helical regions.

A "biofilm" is a complex organization of bacteria that are anchored to a surface via a bacterially extruded exopolysaccharide matrix, and grow into differentiated towers that can be several hundred bacteria in height. The extruded exopolysaccharide matrix, which comprises more than 90% of the biofilm, envelopes the bacteria and provides protection from phagocytosis and oxidative burst mechanisms, both in natural environments and in the host. Bacteria within biofilms are also resistant to the host's humoral defense systems because or a lack of accessibility by immunoglobulin and complement. The attachment of bacteria to a surface triggers the expression of a cassette of genes, which results in the formation of a biofilm. A "biofilm phenotype" confers to a bacterium a reduced metabolic activity and enhanced antibiotic resistance in comparison with the corresponding planktonic phenotype. A "biofilm-producing bacterium" or "biofilm bacterium" is a bacterium capable of producing, forming, and/or accumulating a biofilm in vitro or in vivo, e.g., on artificial and cellular surfaces.

Peptides of the Present Invention

The present invention provides a peptide compound of Formula I (SEQ ID NO: 53):

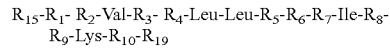

$R_{15}$-$R_1$-$R_2$-Val-$R_3$-$R_4$-Leu-Leu-$R_5$-$R_6$-$R_7$-Ile-$R_8$-$R_9$-Lys-$R_{10}$-$R_{19}$ wherein $R_1$ is 0-1 Cys or ornithine residue;
$R_2$ is 1-3 Lys residues;
$R_3$ is any amino acid residue except a Pro residue;
$R_4$ is any amino acid residue except a Pro residue;
$R_5$ is 1-3 Lys residues;
$R_6$ is 1-10 amino acid residues;
$R_7$ is any amino acid except Asp, Glu, Gly or Pro;
$R_8$ is any amino acid residue except Ala, Asp, Gly, His, Ile, Pro, Trp or Tyr;
$R_9$ is a Val, Ile, Phe, or Trp residue;
$R_{10}$ is 0-1 Cys residue;
$R_{18}$ is 0 amino acids or $R_{12}$-$R_{11}$-Pro-, wherein $R_{11}$ is 0-3 amino acids, wherein the amino acid residues are not Gly or Pro; and
$R_{12}$ is 0-1 Cys residues; and
$R_{19}$ is -$R_{13}$-$R_{14}$-$R_{15}$-$R_{16}$,
wherein $R_{13}$ is 0-1 is Gly residue;
$R_{14}$ is 0-1 Ala residue;
$R_{15}$ is 0-1 Phe residue;
$R_{16}$ is 0-1 Gln residue; and
$R_{17}$ is 0-1 Cys residue.

The present invention provides a peptide compound of Formula II (SEQ ID NO: 54):

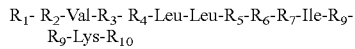
$R_1$- $R_2$-Val-$R_3$- $R_4$-Leu-Leu-$R_5$-$R_6$-$R_7$-Ile-$R_9$-$R_9$-Lys-$R_{10}$ wherein:
$R_1$ is 0-1 Cys residues;
$R_2$ is 1-3 Lys residues;
$R_3$ is any amino acid residue except a Pro residue;
$R_4$ is any amino acid residue except a Pro residue;
$R_5$ is 1-3 Lys residues;
$R_6$ is 1-10 amino acid residues;
$R_7$ is any amino acid except Asp, Glu, Gly or Pro;
$R_8$ is any amino acid residue except Ala, Asp, Gly, His, Ile, Pro, Trp or Tyr;
$R_9$ is a Val, Ile, Phe, or Trp residue; and
$R_{10}$ is 0-1 Cys residues.

The present invention further provides a peptide of Formula III (SEQ ID NO: 55):

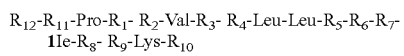
$R_{12}$-$R_{11}$-Pro-$R_1$- $R_2$-Val-$R_3$- $R_4$-Leu-Leu-$R_5$-$R_6$-$R_7$-Ile-$R_8$- $R_9$-Lys-$R_{10}$ wherein:
$R_1$ is 0-1 Cys residues;
$R_2$ is 1-3 Lys residues;
$R_3$ is any amino acid residue except a Pro residue;
$R_4$ is any amino acid residue except a Pro residue;
$R_5$ is 1-3 Lys residues;
$R_6$ is 1-10 amino acid residues;
$R_7$ is any amino acid except Asp, Glu, Gly or Pro;
$R_8$ is any amino acid residue except Ala, Asp, Gly, His, Ile, Pro, Trp or Tyr;
$R_9$ is a Val, Ile, Phe, or Trp residue;
$R_{10}$ is 0-1 Cys residues;
$R_{11}$ is 0-3 amino acids, wherein the amino acid residues are not Gly or Pro; and $R_{12}$ is 0-1 Cys residues.

The present invention further provides a peptide of Formula IV (SEQ ID NO: 56):

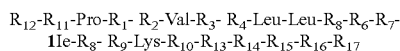
$R_{12}$-$R_{11}$-Pro-$R_1$- $R_2$-Val-$R_3$- $R_4$-Leu-Leu-$R_8$-$R_6$-$R_7$-Ile-$R_8$- $R_9$-Lys-$R_{10}$-$R_{13}$-$R_{14}$-$R_{15}$-$R_{16}$-$R_{17}$ wherein:
$R_1$ is 0-1 Cys residue;
$R_2$ is 1-3 Lys residues;
$R_3$ is any amino acid residue except a Pro residue;
$R_4$ is any amino acid residue except a Pro residue;
$R_5$ is 1-3 Lys residues;
$R_6$ is 1-10 amino acid residues;
$R_7$ is any amino acid except Asp, Glu, Gly or Pro;
$R_8$ is any amino acid residue except Ala, Asp, Gly, His, Ile, Pro, Trp or Tyr;
$R_9$ is a Val, Ile, Phe, or Trp residue;
$R_{10}$ is 0-1 Cys residues;
$R_{11}$ is 0-3 amino acids, wherein the amino acid residues are not Gly or Pro;
$R_{12}$ is 0-1Cys residue;
$R_{13}$ is 0-1 is Gly residue;
$R_{14}$ is 0-1 Ala residue;
$R_{15}$ is 0-1 Phe residue;
$R_{16}$ is 0-1 Gln residue; and
$R_{17}$ is 0-1 Cys residue.

The present invention further provides a peptide of Formula V (SEQ ID NO: 57):

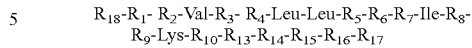
$R_{18}$-$R_1$- $R_2$-Val-$R_3$- $R_4$-Leu-Leu-$R_5$-$R_6$-$R_7$-Ile-$R_8$-$R_9$-Lys-$R_{10}$-$R_{13}$-$R_{14}$-$R_{15}$-$R_{16}$-$R_{17}$ wherein: $R_1$ is 0-1 Cys residue;
$R_2$ is 1-3 Lys residues;
$R_3$ is any amino acid residue except a Pro residue;
$R_4$ is any amino acid residue except a Pro residue;
$R_5$ is 1-3 Lys residues;
$R_6$ is 1-10 amino acid residues;
$R_7$ is any amino acid except Asp, Glu, Gly or Pro;
$R_8$ is any amino acid residue except Ala, Asp, Gly, His, Ile, Pro, Trp or Tyr;
$R_9$ is a Val, Ile, Phe, or Trp residue;
$R_{10}$ is 0-1 Cys residue;
$R_{13}$ is 0-1 is Gly residue;
$R_{14}$ is 0-1 Ala residue;
$R_{15}$ is 0-1 Phe residue;
$R_{16}$ is 0-1 Gln residue;
$R_{17}$ is 0-1 Cys residue; and
$R_{18}$ is 0-1 ornithine residue.

In certain embodiments of the peptide of Formula I-V, both $R_1$ and $R_{10}$ are Cys. In certain embodiments, $R_1$ and $R_{10}$ are covalently linked to form a circular peptide.

In certain embodiments of the peptide of Formula I-V, $R_2$ is a single Lys residue. In certain embodiments of the peptide of Formula I-V, $R_2$ is two Lys residues.

In certain embodiments of the peptide of Formula I-V, $R_3$ is any amino acid residue except a Pro or Gly residue. In certain embodiments of the peptide of Formula I-V, $R_3$ is Gln.

In certain embodiments of the peptide of Formula I-V, $R_4$ is any amino acid residue except a Pro or Gly residue. In certain embodiments of the peptide of Formula I-V, $R_4$ is Asp.

In certain embodiments of the peptide of Formula I-V, $R_5$ is a single Lys residue. In certain embodiments of the peptide of Formula I-V, $R_5$ is two Lys residues.

In certain embodiments of the peptide of Formula I-V, $R_6$ is 1-10 amino acid residues. In certain embodiments of the peptide of Formula I-V, $R_6$ is a single amino acid residue.

In certain embodiments of the peptide of Formula I-V, $R_7$ is any amino acid except Asp, Glu, Gly or Pro. In certain embodiments of the peptide of Formula I-V, $R_7$ is an Asn, Arg, Lys, His, or Ser residue.

In certain embodiments of the peptide of Formula I-V, $R_8$ is any amino acid residue except Ala, Asp, Gly, His, Ile, Pro, Trp or Tyr. In certain embodiments, $R_8$ is Thr.

In certain embodiments of the peptide of Formula I-V, $R_{10}$ is a single Cys residue.

In certain embodiments of the present invention, in the peptide of Formula I, III or IV, $R_{11}$ is a tripeptide consisting of Glu followed by any two amino acid residues. In certain embodiments, $R_{11}$ is a tripeptide consisting of Glu-Ala-Ala.

The term "amino acid" includes the residues of the natural amino acids (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g., phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also includes peptides with reduced peptide bonds, which will prevent proteolytic degradation of the peptide. Also, the term includes the amino acid analog α-aminoisobutyric acid. The term also includes natural and unnatural amino acids bearing a conventional amino protecting group (e.g., acetyl or benzyloxycarbonyl), as well as natural and unnatural amino acids protected at the carboxy terminus (e.g., as a ($C_1$-$C_6$)alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein).

In certain embodiments, the peptides are modified by C-terminal amidation, head to tail cyclic peptides, or containing Cys residues for disulfide cyclization, siderophore modification, or N-terminal acetylation.

The term "peptide" describes a sequence of 7 to 50 amino acids or peptidyl residues. Preferably a peptide comprises 7 to 25, or 7 to 15 or 7 to 13 amino acids. Peptide derivatives can be prepared as disclosed in U.S. Pat. Nos. 4,612,302; 4,853,371; and 4,684,620. Peptide sequences specifically recited herein are written with the amino terminus on the left and the carboxy terminus on the right.

By "variant" peptide is intended a peptide derived from the native peptide by deletion (so-called truncation) or addition of one or more amino acids to the N-terminal and/or C-terminal end of the native peptide; deletion or addition of one or more amino acids at one or more sites in the native peptide; or substitution of one or more amino acids at one or more sites in the native peptide. The peptides of the invention may be altered in various ways including amino acid substitutions, deletions, truncations, and insertions. Methods for such manipulations are generally known in the art. For example, amino acid sequence variants of the peptides can be prepared by mutations in the DNA. Methods for mutagenesis and nucleotide sequence alterations are well known in the art. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall peptide retains its spatial conformation but has altered biological activity. For example, common conserved changes might be Asp to Glu, Asn or Gln; His to Lys, Arg or Phe; Asn to Gln, Asp or Glu and Ser to Cys, Thr or Gly. Alanine is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains.

Compositions and Methods of Use

The present invention provides a therapeutic method for preventing or treating a pathological condition or symptom in a mammal, such as a human, wherein an antibiotic activity is implicated and antagonism of its action is desired, by administering to a mammal in need of such therapy, an effective amount of a compound of Formula I-IV.

The present invention provides a therapeutic method for preventing or treating a pathological condition or symptom in a mammal, such as a human, wherein anti-biofilm formation activity is implicated and antagonism of its action is desired, comprising administering to a mammal in need of such therapy, an effective amount of a compound of Formula I-IV.

The present invention provides a method to treat a microbial infection comprising administering a therapeutically effective amount of a compound of Formula I to a mammal. In certain embodiments, the bacteria are gram-negative bacteria, such as, for example, *Porphyromonas gingivalis*.

The present invention provides a compound of Formula I for use in medical therapy.

The present invention provides the use of a compound of Formula I for the manufacture of a medicament useful for the treatment of a microbial infection in a mammal.

The present invention provides a method of preventing the adhesion of bacteria on a solid substrate comprising contacting the solid substrate with a peptide of Formula I-IV. In certain embodiments, the peptide is dispersed in a polymer.

The present invention provides a method of preventing the formation of a biofilm of bacteria on a solid substrate comprising contacting the solid substrate with a peptide of Formula I-IV.

The present invention provides a method of preventing the formation of a biofilm of bacteria in vivo comprising contacting a tissue surface with a peptide of Formula I-IV. In certain embodiments, the tissue is oral or lung tissue. In certain embodiments, the tissue is a mucosal surface. In certain embodiments, the bacteria are gram-negative bacteria, such as, for example, *Porphyromonas gingivalis*.

The compounds of the present invention can be formulated as consumer product compositions and administered to a mammalian host, such as a human in a variety of forms adapted to the chosen route of administration, e.g., orally. In certain embodiments the compound is included in a toothpaste, a mouth rinse or as a coating on a dental floss.

Further, the compounds of the present invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents, for example, other agents that are useful as antibiotics. Examples of such agents include a protein synthesis inhibitor, a cell wall growth inhibitor, a cell membrane synthesis inhibitor, a nucleic acid synthesis inhibitor, or a competitive enzyme inhibitor. In certain embodiments, the additional agent is an antibiotic such as penicillin, ampicillin, amoxicillin, vancomycin, cycloserine, bacitracin, cephalolsporin, imipenem, colistin, methicillin, streptomycin, kanamycin, tobramycin, gentamicin, tetracycline, chlortetracycline, doxycycline, chloramphenicol, lincomycin, clindamycin, erythromycin, oleandomycin, polymyxin nalidixic acid, rifamycin, rifampicin, gantrisin, trimethoprim, isoniazid, paraminosalicylic acid, or ethambutol.

In certain embodiments, the compound of the invention is contacted with a microbe.

Accordingly, in one embodiment the invention also provides a composition comprising a compound of the present invention, at least one other therapeutic agent, and a pharmaceutically acceptable diluent or carrier. The invention also provides a kit comprising a compound of the present invention, at least one other therapeutic agent, packaging material, and instructions for administering the compound of the present invention or the pharmaceutically acceptable salt thereof and the other therapeutic agent or agents to an animal to prevent bacterial infection.

In certain embodiments the peptide of the present invention is produced as a fusion protein of the peptide sequence and a carrier protein. The carrier protein can subsequently be cleaved to release the active peptide. Phage display of active peptides may also be a useful method to present the peptide to cells.

The present invention also provides a solution that includes a solvent, a polymer dissolved in the solvent and a peptide of Formula I dispersed in the solvent.

Solid Substrates

In one embodiment of the invention, a solution which includes a solvent, a polymer dissolved in the solvent and a peptide of Formula I dispersed in the solvent is applied to a solid substrate and then the solvent is evaporated. The inclusion of a polymer in intimate contact with a peptide on the underlying solid substrate allows the peptide to be retained on the solid substrate in a resilient matrix during expansion of the solid substrate and also slows the administration of drug following implantation. The method can be applied whether the solid substrate has a metallic or polymeric surface. The method is also an extremely simple method since it can be applied by simply immersing the solid substrate into the solution or by spraying the solution onto the solid substrate. The amount of peptide to be included on the solid substrate can be readily controlled by applying multiple thin coats of the solution while allowing it to dry between coats. The overall coating should be thin enough so that it will not significantly increase the profile of the solid substrate. It is therefore preferably less than about 0.002 inch thick and most preferably less than 0.001 inch thick. The adhesion of the coating and the rate at which the peptide is delivered can be controlled by the selection of an appropriate bioabsorbable or biostable polymer and by the ratio of peptide to polymer in the solution. By this method, peptides can be applied to a solid substrate, be retained on a solid substrate during expansion of the solid substrate, and elute the peptide at a controlled rate. The release rate can be further controlled by varying the ratio of peptide to polymer in the multiple layers. The release rate can be further controlled by varying the ratio of peptide to polymer in the multiple layers. For example, a higher peptide-to-polymer ratio in the outer layers than in the inner layers would result in a higher early dose which would decrease over time. Examples of some suitable combinations of polymers and solvent are set forth in Table 1 below.

TABLE 1

| Polymer | Solvent |
| --- | --- |
| poly(L-lactic acid) | chloroform |
| poly(lactic acid-co-glycolic acid) | acetone |
| polyether | N-methyl |
| urethane | pyrrolidone |
| silicone adhesive | xylene |
| poly(hydroxy-butyrate-co-hydroxyvalerate) | dichloro-methane |

The present invention further provides a peptide-coated device that includes (a) a solid substrate; and (b) a solid composite of a compound of Formula I and a therapeutic substance in an adherent layer on the solid substrate. In certain embodiments, the solid substrate has a metal surface, or a polymeric surface. In certain embodiments, the solid composite includes a plurality of layers. In certain embodiments, the ratio of therapeutic substance to polymer is varied in some of the layers. In certain embodiments, the polymer is a bioabsorbable polymer. In certain embodiments, the polymer is poly(L-lactic acid), poly(lactide-co-glycolide) or poly(hydroxybutyrate-co-valerate). In certain embodiments, the polymer is a biostable polymer. In certain embodiments, the polymer is polymer is a silicone, polyurethane, polyester, vinyl homopolymer or copolymer, acrylate homopolymer or copolymer, polyether or cellulosic, or a combination thereof. In certain embodiments, the ratio of compound to polymer in the layer is in the range of about 10:1 to 1:100.

Examples of various polymers used in forming the peptide-eluting component include poly(methyl(meth)acrylate ("PMMA"), ethylenevinylalcohol ("EVAL"), poly(butyl (meth)acrylate) ("PBMA"), biodegradable polymers (i.e., Poly(glycolic acid) ("PGA") and poly(L-lactic acid) ("PLLA"), polyethylene glycol ("PEG"), hyaluronic acid ("HA"), polyester amide ("PEA"), poly(glycerol-sebacate) ("PGS"), nanoscale structures of carbon, acetal copolymer, acetal homopolymer, acrylonitrile butadiene styrene, ABS and polycarbonate, nylon, polyamide, polyacrylate, polyaryl sulfone, polycarbonate, polyetherketone, polyetherimide, polyether sulfone, polyethylene terephthalate, polyimide, polyphenylene oxide, polyphenylene sulfide, polypropylene, polysulfone, polyurethane, polyvinyl chloride, styrene acrylonitrile and other suitable polymers. It is contemplated that the above polymers can be slowly dissolved or chemically degraded or both. As set forth above, the local drug-eluting component alternatively may be fabricated from porous ceramic or various metals or alloys, including stainless steel, platinum, titanium, tantalum, nickel-titanium, cobalt-chromium, and alloys thereof. This family of polymers comprises the following basic components: (1) moieties derived from aliphatic diols, triols, or polyols; (2) moieties derived from polycarboxylic acids (carboxylic acids containing more than one acid functionality); and (3) biobeneficial, non-fouling, or bioactive moieties (U.S. Pat. No. 7,186,789, incorporated by reference herein).

Methods of Manufacture

The present invention provides a method for manufacturing a peptide-coated solid substrate by applying to the solid substrate a layer which is a solid composite of polymer and a peptide of Formula I-IV, wherein the first layer is applied by the steps of: (a) applying to the solid substrate a solution which includes a solvent, a polymer dissolved in the solvent and a peptide dispersed in the solvent; and (b) evaporating the solvent to form a composite of polymer and peptide. In certain embodiments, the solution is applied by spraying. In certain embodiments, the solution is applied in a plurality of application and drying steps. In certain embodiments, the ratio of peptide to dissolved polymer in the solution is varied in some of the plurality of application steps. In certain embodiments, the polymer is a bioabsorbable polymer. In certain embodiments, the polymer is poly(L-lactic acid), poly (lactide-co-glycolide) or poly(hydroxybutyrate-co-valerate). In certain embodiments, the polymer is a biostable polymer. In certain embodiments, the polymer is polymer is a silicone, polyurethane, polyester, vinyl homopolymer or copolymer, acrylate homopolymer or copolymer, polyether or cellulosic, or a combination thereof. A typical ratio of peptide to dissolved polymer in the solution can vary widely (e.g., in the range of about 10:1 to 1:100).

Nucleic Acids of the Present Invention

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues. A "nucleic acid fragment" is a fraction of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA that can be single- or double-stranded, optionally containing synthetic, non-natural or altered nucleotide bases capable of incorporation into DNA or RNA polymers. The terms "nucleic acid," "nucleic acid molecule," "nucleic acid fragment," "nucleic acid sequence or segment," or "polynucleotide" may also be used interchangeably with gene, cDNA, DNA and RNA encoded by a gene.

The invention encompasses isolated or substantially purified nucleic acid or protein compositions. In the context of the present invention, an "isolated" or "purified" DNA molecule or an "isolated" or "purified" polypeptide is a DNA molecule or polypeptide that exists apart from its native environment and is therefore not a product of nature. An isolated DNA molecule or polypeptide may exist in a purified form or may exist in a non-native environment such as, for example, a transgenic host cell or bacteriophage. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed nucleotide sequences and proteins or partial-length proteins encoded thereby are also encompassed by the present invention. By "fragment" or "portion" is meant a full length or less than full length of the nucleotide sequence encoding, or the amino acid sequence of, a polypeptide or protein.

The term "gene" is used broadly to refer to any segment of nucleic acid associated with a biological function. Thus, genes include coding sequences and/or the regulatory sequences required for their expression. For example, gene refers to a nucleic acid fragment that expresses mRNA, functional RNA, or specific protein, including regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

"Naturally occurring" is used to describe an object that can be found in nature as distinct from being artificially produced. For example, a protein or nucleotide sequence present in an organism (including a virus), which can be isolated from a source in nature and which has not been intentionally modified by man in the laboratory, is naturally occurring.

The term "chimeric" refers to any gene or DNA that contains 1) DNA sequences, including regulatory and coding sequences that are not found together in nature or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

A "transgene" refers to a gene that has been introduced into the genome by transformation and is stably maintained. Transgenes may include, for example, DNA that is either heterologous or homologous to the DNA of a particular cell to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

The terms "protein," "peptide" and "polypeptide" are used interchangeably herein.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

"Recombinant DNA molecule" is a combination of DNA sequences that are joined together using recombinant DNA technology and procedures used to join together DNA sequences as described, for example, in Sambrook and Russell, *Molecular Cloning: A Laboratory Manual*, Cold Spring Harbor, N.Y.: Cold Spring Harbor Laboratory Press (3$^{rd}$ edition, 2001).

The terms "heterologous DNA sequence," "exogenous DNA segment" or "heterologous nucleic acid," each refer to a sequence that originates from a source foreign to the particular host cell or, if from the same source, is modified from its original form. Thus, a heterologous gene in a host cell includes a gene that is endogenous to the particular host cell but has been modified. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced.

"Wild-type" refers to the normal gene, or organism found in nature without any known mutation.

"Genome" refers to the complete genetic material of an organism.

A "vector" is defined to include, inter alia, any plasmid, cosmid, phage or binary vector in double or single stranded linear or circular form which may or may not be self transmissible or mobilizable, and which can transform prokaryotic or eukaryotic host either by integration into the cellular genome or exist extrachromosomally (e.g., autonomous replicating plasmid with an origin of replication).

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

Such expression cassettes will comprise the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

A "functional RNA" refers to an antisense RNA, ribozyme, or other RNA that is not translated.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, inducible promoters and viral promoters.

"5+ non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency.

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e. further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation in a cell of an endogenous gene, transgene, as well as the transcription and stable accumulation of sense (mRNA) or functional RNA. In the case of antisense constructs, expression may refer to the transcription of the antisense DNA only. Expression may also refer to the production of protein.

"Transcription stop fragment" refers to nucleotide sequences that contain one or more regulatory signals, such as polyadenylation signal sequences, capable of terminating transcription. Examples of transcription stop fragments are known to the art.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

The terms "cis-acting sequence" and "cis-acting element" refer to DNA or RNA sequences whose functions require them to be on the same molecule.

The terms "trans-acting sequence" and "trans-acting element" refer to DNA or RNA sequences whose function does not require them to be on the same molecule.

"Chromosomally-integrated" refers to the integration of a foreign gene or DNA construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a known mathematical algorithm. Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Software for performing BLAST analyses is publicly available through the National Center for Biotechnology Information (available on the world wide web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the world-wide-web at ncbi.nlm.nih.gov. Alignment may also be performed manually by visual inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, or 79%, at least 80%, 81%, 82%, 83%, 84%, 85%, 86%, 87%, 88%, or 89%, at least 90%, 91%, 92%, 93%, or 94%, and at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to the reference sequence over a specified comparison window. An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point ($T_m$) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl: $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), it is preferred to increase the SSC concentration so that a higher temperature can be used. Generally, highly stringent hybridization and wash conditions are selected to be about SEC lower than the $T_m$ for the specific sequence at a defined ionic strength and pH.

An example of highly stringent wash conditions is 0.15 M NaCl at 72EC for about 15 minutes. An example of stringent wash conditions is a 0.2×SSC wash at 65EC for 15 minutes. Often, a high stringency wash is preceded by a low stringency wash to remove background probe signal. An example medium stringency wash for a duplex of, e.g., more than 100 nucleotides, is 1×SSC at 45EC for 15 minutes. An example low stringency wash for a duplex of, e.g., more than 100 nucleotides, is 4-6×SSC at 40EC for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30EC and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

Thus, the genes and nucleotide sequences of the invention include both the naturally occurring sequences as well as mutant forms. Likewise, the polypeptides of the invention encompass naturally occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism into which a heterologous nucleic acid molecule has been introduced. The nucleic acid molecule can be stably integrated into the genome generally known in the art. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

A "transgenic" organism is an organism having one or more cells that contain an expression vector.

By "portion" or "fragment," as it relates to a nucleic acid molecule, sequence or segment of the invention, when it is linked to other sequences for expression, is meant a sequence having at least 80 nucleotides, more preferably at least 150 nucleotides, and still more preferably at least 400 nucleotides. If not employed for expressing, a "portion" or "fragment" means at least 9, preferably 12, more preferably 15, even more preferably at least 20, consecutive nucleotides, e.g., probes and primers (oligonucleotides), corresponding to the nucleotide sequence of the nucleic acid molecules of the invention.

As used herein, the term "therapeutic agent" refers to any agent or material that has a beneficial effect on the mammalian recipient. Thus, "therapeutic agent" embraces both therapeutic and prophylactic molecules having nucleic acid or protein components.

"Treating" as used herein refers to ameliorating at least one symptom of, curing and/or preventing the development of a given disease or condition.

The invention will now be illustrated by the following non-limiting Examples.

EXAMPLE 1

Synthesis of Variant BAR Peptides

The inventor synthesized a peptide, SspB Adherence Region (BAR) representing the region of SspB that was shown to be involved in the interaction of P. gingivalis with S. gordonii. This peptide was shown to inhibit the development of P. gingivalis biofilms on a substrate of S. gordonii cells attached to a saliva coated coverglass in a dose dependent manner. The $I_{50}$ for BAR was calculated to be about 1.3 µM. The kinetics of inhibition were also similar to the kinetics of association of the BAR peptide with its receptor on P. gingivalis, the minor fimbrial protein Mfa. Within BAR, the NITVK (SEQ ID NO: 2) motif was shown to be important for P. gingivalis adherence. To further characterize the SspB-Mfa interacting interface, the inventor screened a biased combinatorial library using the BAR peptide as the lead compound in which the active amino acids in the NITVK (SEQ ID NO: 2) motif were randomized. The inventor showed that substitution of basic amino acids or serine for $N^{1182}$, and substitution of hydrophobic residues Ile, Trp or Phe for $V^{1185}$ promoted P. gingivalis adherence. These results suggested that both electrostatic and hydrophobic interactions contribute to P. gingivalis adherence. Furthermore, substitution of α-helix breaking residues Pro or Gly were detrimental for P. gingivalis adherence, consistent with previous site specific mutagenesis results. This suggests that secondary structure is important for P. gingivalis adherence.

The results suggested that the α-helical character of BAR may be important for its activity. Interestingly, examination of BAR showed it resembled a known protein-protein interacting motif, the nuclear receptor box of eukaryotic cells. The NR box mediates interactions of nuclear receptors (NR) with their co-activating proteins which is driven by the association of a hydrophobic α-helix of consensus sequence LXXLL (SEQ ID NO:6), with a hydrophobic pocket in the NR protein. This initial interaction is stabilized by electrostatic interactions that form with charged amino acids that flank LXXLL (SEQ ID NO: 6). The specificity of co-activator interaction with a given NR is determined by residues that reside either upstream or downstream from LXXLL (SEQ ID NO: 6). The BAR peptide contains a hydrophobic predicted α-helix of sequence VXXLL (SEQ ID NO: 3) that is flanked on each side by positively charged lysine residues. This region resides immediately upstream from the NITVK (SEQ ID NO: 2) motif that the inventor has shown dictates the specificity of P. gingivalis adherence for SspB over S. mutans antigen I/II. Together, these results suggested that VXXLL (SEQ ID NO: 3) may contribute to the Mfa/SspB interaction.

An unexpected finding from the inventor's screen of the BAR combinatorial library was that substitution of some amino acids in the NITVK (SEQ ID NO: 2) motif promoted increased P. gingivalis adherence to the peptide. Based on this finding, an analog of BAR (C1-BAR) that contained adherence promoting residues replacing $N^{1182}$ and $V^{1185}$ was synthesized. The preliminary functional analysis of this peptide suggested that it was a more potent inhibitor of P. gingivalis biofilm development than BAR. At the three peptide concentrations tested, fewer P. gingivalis microcolonies formed on adherent streptococci when P. gingivalis was incubated with the new peptide than with BAR.

To determine if BAR is susceptible to proteolytic cleavage by P. gingivalis, samples of the peptide were incubated with culture extracts from P. gingivalis and analyzed on 10-20% Tris-Tricine gradient gels. BAR was slowly degraded during the 1 hour incubation, suggesting that BAR is a substrate for at least some P. gingivalis proteases. In contrast, a retro-inverso peptide, $R_1$—BAR, was resistant to cleavage, suggesting that peptide modifications to limit proteolytic cleavage of BAR will increase its longevity in the presence of P. gingivalis. However, the retro-inverso peptide was a poor inhibitor of P. gingivalis biofilm formation. This suggested that weak interactions of Mfa with the peptide backbone of BAR were important for its activity and underscored the need to be selective when altering the stereochemistry of the peptide backbone.

The results suggested that the structure of BAR, and in particular, the α-helical characteristics of the peptide were important for P. gingivalis adherence. To more accurately assess the secondary structures of BAR, samples of the peptide were subjected to circular dichroism spectroscopy and spectra were analyzed using k2d analysis software (Andrade et al., 1993, *Prot. Eng.* 6, 383-390). The spectra obtained is shown in FIG. 1. Analysis of these data were consistent with a structurally flexible small peptide in solution, and indicate that BAR peptide was comprised of approximately 48% random coil, 7% α-helix, and 45% α-sheet.

*P. gingivalis* is one of the primary pathogens associated with adult periodontitis and is an acid intolerant, asaccharolytic, obligate anaerobe whose primary niche is in the subgingival pocket. However, it is likely that *P. gingivalis* first colonizes supragingival plaque prior to becoming established in its primary niche. To survive in this hostile environment (which can be aerobic and contains saccharolytic, acid producing bacteria), *P. gingivalis* may rely on interactions with other organisms in supragingival plaque for physiologic support. For example, *P. gingivalis* co-aggregates with *Fusobacterium nucleatum*, an organism that may provide a stable local redox environment. *F. nucleatum* in turn, can co-aggregate with *S. gordonii* and our studies have shown that *P. gingivalis* adheres to *S. gordonii* but not to *S. mutans*, which may serve to isolate *P. gingivalis* from highly acidic areas of supragingival plaque. Since the interactions of *P. gingivalis* with these organisms may represent some of the first steps that allow *P. gingivalis* to infect the oral biofilm, they are ideal targets for therapeutic intervention.

*P. gingivalis* adheres to the antigen I/II polypeptide of *S. gordonii* (i.e., the SspB protein) and that a specific region of SspB (SspB Adherence Region, designated BAR) mediates adherence. This interaction was also essential for the subsequent formation of *P. gingivalis* biofilms on streptococci. Interestingly, adherence of *P. gingivalis* to oral streptococci was selective; *P. gingivalis* adhered only to *S. gordonii* but not to *S. mutans* even though both organisms possess an antigen I/II protein and the BAR region of SspB is well conserved in the *S. mutans* polypeptide. The inventor has previously shown that the *P. gingivalis* receptor for SspB is the minor fimbrial antigen Mfa, and that a synthetic peptide comprising BAR bound to Mfa whereas a peptide representing the corresponding region of *S. mutans* antigen I/II did not. Using a combinatorial approach with the BAR peptide as the lead compound, the inventor identified characteristics of the SspB-Mfa interacting interface that may explain the selectivity of the interaction for SspB. Furthermore, the inventor demonstrated that a synthetic BAR peptide inhibited *P. gingivalis* adherence to *S. gordonii*. Thus, the overall hypothesis was that the Mfa-SspB interaction is the driving force behind the selective adherence and formation of *P. gingivalis* biofilms on oral streptococci and represents a viable target for therapeutic intervention of *P. gingivalis* colonization of the human oral cavity.

The following experiments were designed to further define the Mfa-SspB interacting interface and to develop high specific activity peptide-based inhibitors of *P. gingivalis* adherence: A) determining if the VXXLL (SEQ ID NO: 3) hydrophobic α-helix of BAR contributes to the Mfa-SspB interaction, B) introducing amino acid substitutions in the NITVK (SEQ ID NO: 2) active region of BAR to optimize the specific inhibitory activity of BAR, C) determining and limiting the susceptibility of BAR peptide analogs to proteolytic degradation by *P. gingivalis*, and D) determining solution structural characteristics of BAR peptide inhibitors for the rational development of structurally constrained peptide inhibitors containing the VXXLL (SEQ ID NO: 3) and/or NITVK (SEQ ID NO: 2) motifs. These experiments provide with a more detailed picture of the molecular interactions and structural motifs that contribute to *P. gingivalis*-streptococcal adherence. The results of these experiments also provide a foundation to rationally design and construct highly active peptide-based inhibitors of *P. gingivalis* adherence.

A. Contribution of VXXLL (SEQ ID NO: 3) hydrophobic α-helix. As described above, the BAR sequence resembles a NR box, a motif that mediates protein-protein interactions of nuclear receptors (NR) and co-activators in eukaryotic cells. The interaction of co-activator with NR is driven by the association of a hydrophobic α-helix of consensus sequence LXXLL (SEQ ID NO: 6), with a hydrophobic pocket in the NR protein. This initial interaction is in turn stabilized by electrostatic interactions that form with charged amino acids that flank LXXLL (SEQ ID NO: 6). However, the specificity of co-activator interaction with a given NR is determined by residues that reside either upstream or downstream from LXXLL (SEQ ID NO: 6). The BAR peptide contains a hydrophobic predicted α-helix of sequence VXXLL (SEQ ID NO: 3) that is flanked on each side by positively charged lysine residues. This region resides immediately upstream from the NITVK (SEQ ID NO: 2) sequence which we have shown dictates the selectivity of *P. gingivalis* adherence for SspB over *S. mutans* antigen I/II. In addition, substitution of cystiene for Leu$^{1177}$ (underlined) reduced the specific inhibitory activity of BAR, suggesting that VXXLL (SEQ ID NO: 3) may contribute to the Mfa/SspB interaction. Thus, BAR resembles the NR box and its interaction with *P. gingivalis* requires the VXXLL (SEQ ID NO: 3) α-helix.

To determine if the VXXLL (SEQ ID NO: 3) region contributes to *P. gingivalis* adherence to SspB, the following peptides containing substitutions in the VXXLL (SEQ ID NO: 3) motif were synthesized: a) substitution of the hydrophobic residues $V^{1174}$, $L^{1177}$, and $L^{1178}$ with neutral or charged residues that maintain the α-helical structure of the region (e.g., Asp, Asn, Gln). These peptides maintain the overall secondary structural properties of the VXXLL (SEQ ID NO: 3) region but allow assessment of the contribution of the hydrophobic character in the interaction with *P. gingivalis*; b) substitution of $Q^{1175}$ and $D^{1176}$ with Pro and Gly which introduced a β-turn, thus disrupting the α-helical structure of the region without significantly affecting the hydrophobic character of VXXLL (SEQ ID NO: 3); and c) substitution of the charged lysine residues with neutral or negatively charged amino acids that do not disrupt the α-helical structure of VXXLL (SEQ ID NO: 3) (e.g., Asp, Asn, Gln). These peptides allow assessment of the contribution of electrostatic interactions that may occur between the lysine residues of BAR and Mfa. The maintenance or loss of α-helical structure in the above groups of peptides were assessed by circular dichroism spectroscopy.

B. Altering NITVK (SEQ ID NO: 2) to increase specific inhibitory activity of BAR. A surprising result from the screening of the biased combinatorial BAR peptide library was that some amino acid substitutions for $N^{1182}$ and for $V^{1185}$ resulted in increased adherence of *P. gingivalis*. For example, at position 1182, the most active amino acids were Arg and Ser, although other basic amino acids (Ly,s and His) also promoted greater adherence than the endogenous Asn$^{1182}$ residue in the BAR sequence. At position 1185, the hydrophobic amino acids Ile, Phe and Trp promoted greater adherence relative to the Val$^{1185}$ residue of BAR.

Therefore, the physical and chemical characteristics of the amino acids occupying positions 1182 and 1185 are important for BAR interactions and more active analogs of BAR can be synthesized by amino acid substitutions at these positions. The screening of the combinatorial library did not allow rigorous assessment of the kinetics of adherence. Therefore, the inventor synthesized and evaluated the activity of purified peptides containing the substitutions at positions 1182 and 1185 that promoted the highest adherence of P. gingivalis in the combinatorial screen. One peptide containing $N\mu R^{1182}$ and $V\mu I^{1185}$ substitutions (peptide "a" in FIG. 2) suggested that it is a more potent inhibitor of P. gingivalis adherence and biofilm development than BAR. Three additional peptide analogs of BAR were synthesized that contain the following substitutions: $N\mu R_{1182}$ /$V\mu I^{1185}$, $N\mu I^{1182}$/$V\mu I^{1185}$ and $N\mu S^{1182}$/$V\mu F^{1185}$. Each of these three peptides (along with the $N\mu R^{1182}$/$V\mu I^{1185}$ peptide that is already available) were assessed for P. gingivalis binding activity and inhibition of P. gingivalis adherence and biofilm formation as described above.

C. Limiting proteolytic degradation of BAR peptides by P. gingivalis gingipains. P. gingivalis possesses a number of potential proteases that could degrade BAR peptide, thus potentially decreasing its effectiveness as an inhibitor of adherence and biofilm development. Indeed, BAR is slowly degraded upon exposure to P. gingivalis culture extracts, and by limiting proteolysis of BAR, its specific inhibitory activity is increased. However, the P. gingivalis genome sequence encodes a number of putative proteases. The inventor is determining if BAR is degraded by the gingipains. The rationale for focusing on the gingipains is that they represent the major proteolytic activities expressed by P. gingivalis, they are well characterized and can be readily purified. Furthermore, BAR contains several lysine residues and therefore is a potential substrate for Kgp. In addition, several of the BAR analogs described in section "B" contain arginine substitutions (FIG. 2) and may also be susceptible to Rgp.

The inventor first compares the kinetics of peptide degradation after exposure of BAR or its $N\mu R^{1182}/V\mu I^{1185}$ analog to culture extracts from wild type (i.e., strain 33277) and Rgp/Kgp deficient strains of P. gingivalis. Prior to use, gingipain activity in the extracts are measured using the colorimetric substrates BAPNA (for Rgp) and ALNA (for Kgp) as described by Sheets et al. (2005, Infect. Immun. 73:1543-1552). Time course degradation of BAR is followed by densitometry of the peptide band after electrophoresis of the reaction mixture in 10-20% Tris-Tricine gels. To confirm the role of Kgp and Rgp, other reactions are carried out in the presence of the specific gingipain inhibitors Z-Phe-Lys-2,4, 6-trimethylbenzoyloxymethylketone and H-D-Phe-Phe-Arg-chloromethylketone, respectively. If necessary, digestions also are conducted using purified gingipain preparations. For these experiments, Arg and Lys-gingipains is co-purified from culture supernatant by acetone precipitation followed by gel filtration and arginine-Sepharose chromotography (Pike et al., 1994, J. Biol. Chem. 269:406-411; Sheets et al., 2005, Infect. Immun. 73:1543-1552).

Pseudopeptides that contain modified amino acid residues at the appropriate sites determined from above are obtained from a commercial sources. Two types of modifications are made: pseudopeptides in which the peptide bond of the selected residue(s) is reduced (—CHR—$CH_2$—NH— versus —CHR—CO—NH—) or partial retro-inverso peptides in which the selected residue(s) is substituted with the D-amino acid in the reverse orientation relative to BAR. Either render the pseudopeptide recalcitrant to proteolytic cleavage at the modified residue. Subsequently, the pseudopeptides are analyzed for binding to P. gingivalis and for inhibition of P. gingivalis biofilm formation using the flow chamber biofilm system previously described (Amorin Daep et al., 2006, Infect. Immun. 74:5756-5762).

D. Development of structurally constrained BAR peptide analogs. BAR peptide is a potent inhibitor of P. gingivalis adherence and biofilm development on a streptococcal substrate. Structure predictions also suggested that the active site of BAR may involve both α-helical and β-sheet secondary structures and the inventors' circular dichroism (CD) data showed that BAR peptide can assume these structures in solution. However, short peptides are structurally flexible and only a fraction of the BAR peptide exists in the "active" conformation in solution at any given time. Therefore, by constraining the flexibility of BAR, it is possible to lock the peptide in a structure(s) that more closely resembles the native conformation of SspB and thus exhibit greater bioactivity. This is accomplished by synthesizing and examining the bioactivity of cyclic analogs of BAR that are structurally constrained. Constrained peptide(s) are identified that exhibit higher specific inhibitory activity than BAR and bioactivity is correlated with the structural properties of the peptide using CD spectroscopy.

The effect of constraining the entire BAR peptide, both on its structural properties and bioactivity (i.e., adherence to Mfa and inhibition of P. gingivalis biofilm formation) is examined. Thus, a cyclic disulfide constrained peptide is synthesize that contains cystiene residues on the N- and C-termini of BAR ("a" in FIG. 3). This serves to limit peptide bond rotation across the entire BAR peptide sequence. The solution structure of the constrained peptide is assessed by circular dichroism and compared to native BAR to monitor the effects of cyclization on its secondary structure. Bioactivity of the constrained peptide is examined as previously described in section A.

Additional constrained peptides are synthesized (exemplified by peptides "b, c, d, and e" in FIG. 3). For example, since BAR resembles a NR box and the VXXLL (SEQ ID NO: 3) α-Helix and flanking lysine residues are shown to be important, cystiene (C) substitutions are made at pro$^{1171}$ and gly$^{1187}$. This constrained analog (peptide "b", FIG. 3) represents the smallest peptide capable of possessing both VXXLL (SEQ ID NO: 3) and NITVK (SEQ ID NO: 2). In addition, the α-helical character of VXXLL (SEQ ID NO: 3) is stabilized with a thioether tether by replacing pro$^{1171}$ and gln $^{1175}$ with ornithine (O) and cysteine, respectively (peptide "c"). Prior to deprotection and release of the synthetic peptide from the solid support, ornithine is bromoacylated with bomoacetic acid. Subsequently, the remaining side chain protective groups are removed with HF and the thioether tether is formed spontaneously in 6M guanidine.HCL in phosphate buffer. These residues lie on the same face of the predicted amphipathic α-helix and locks the peptide in an α-helix without affecting the hydrophobic residues of VXXLL (SEQ ID NO: 3) or the potentially important lysines that flank the sequence. Ornithine and Cys substitutions are also be introduced into the truncated peptide "b" to yield the constrained peptide "d." .

Functional analysis of the constrained peptides is conducted as already described. Structural analyses is carried out by CD spectroscopy. CD spectra are analyzed to determine percent α-helix, β-sheet and random coil structure using the program k2d (Andrade et al., 1993. Prot. Eng. 6, 383-390).

The structure of the peptide is important for its recognition by Mfa. Limiting the structural freedom of BAR peptide in solution results in more ordered secondary structure and the peptides may more closely resemble the "active" conformation that exists in the intact SspB protein. Therefore, the CD spectra of constrained peptides shows a higher degree of α-helix and/or β-sheet, and lower random coil than BAR itself. Correlating the structural properties of constrained peptides with their bioactivity allows identification of highly active inhibitors of P. gingivalis adherence.

EXAMPLE 2

Optimization of BAR Peptides

*Porphyromonas gingivalis* initially colonizes the oral cavity by interacting with organisms in supragingival plaque, such as the oralis group of oral streptococci. This interaction involves association of the streptococcal antigen I/II with the minor fimbrial antigen (Mfa1) of *P. gingivalis*. Our previous studies showed that a peptide (BAR) derived from antigen I/II inhibits *P. gingivalis* adherence and subsequent biofilm formation on streptococcal substrates. In addition, screening a combinatorial peptide library identified select amino acid substitutions in the NITVK (SEQ ID NO: 2) active region of BAR that increased adherence of *P. gingivalis* to streptococci. Here we report that incorporating these residues in a synthetic peptide results in more potent inhibition of *P. gingivalis* adherence and biofilm formation ($I_{50}$=0.52 µM versus $I_{50}$=1.25 µM for BAR). In addition, a second structural motif in BAR, comprised of the amino acids KKVQDLLKK (SEQ ID NO:13) was shown to contribute to *P. gingivalis* adherence to streptococci. Consistent with this, the KKVQDLLKK (SEQ ID NO: 13) and NITVK (SEQ ID NO: 2) motifs are conserved only in antigen I/II proteins expressed by the oralis group of streptococci, which interact with *P. gingivalis*. Interestingly, the primary and secondary structures, and the functional characteristics of the amphipathic VQDLL (SEQ ID NO: 1) core α-helix resemble the consensus nuclear receptor (NR) box protein-protein interacting domain sequence (LXXLL (SEQ ID NO: 6)) of eukaryotes. BAR peptides containing amino acid substitutions with the potential to disrupt the secondary structure of VQDLL (SEQ ID NO: 1) were less effective inhibitors of *P. gingivalis* adherence and biofilm formation, suggesting that the α-helical character of VQDLL (SEQ ID NO: 1) is important. Furthermore, replacing the lysines that flank VQDLL (SEQ ID NO: 1) with acidic amino acids also reduced inhibitory activity, suggesting that the association of VQDLL (SEQ ID NO: 1) with Mfa1 may be stabilized by a charge clamp. These results indicate that the Mfa1-interacting interface of streptococcal antigen I/II encompasses both the KKVQDLLKK (SEQ ID NO: 13) and NITVK (SEQ ID NO: 2) motifs and suggest that the adherence of *P. gingivalis* to streptococci is driven by a protein-protein interaction domain that resembles the eukaryotic NR box. Thus, both motifs must be taken into account for designing potential peptidomimetics that target *P. gingivalis* adherence and biofilm formation.

Adult periodontitis is associated with elevated levels of several Gram negative organisms in the subgingival oral biofilm, including the asaccharolytic, obligate anaerobe *Porphyromonas gingivalis*. In this primary niche, *P. gingivalis* interacts with a variety of other Gram negative obligate and facultative anaerobes, such as *Fusobacterium nucleatum*, *Treponema denticola*, and *Tannerella forsythus* through specific receptor-ligand interactions. However, the initial colonization of the oral cavity by *P. gingivalis* likely occurs through adherence to organisms in the supragingival biofilm and the successful colonization of this niche by *P. gingivalis* is contingent upon a variety of factors such as reduced oxygen tension and sufficient nutritional sources. Consistent with this, *P. gingivalis* has been shown to also adhere to organisms in supragingival plaque that may provide it with physiologic support, such as *Streptococcus gordonii* and *F. nucleatum*.

The adherence of *P. gingivalis* to *S. gordonii* is multimodal. The long and short fimbriae of *P. gingivalis* have both been shown to be involved in this interaction. The structural subunit of the long fimbriae, FimA, interacts with cell surface glyceraldehyde-3-phosphate dehydrogenase of *S. gordonii*, whereas the minor fimbrial protein, Mfa1, interacts with streptococcal cell surface protein SspB, a member of the antigen I/II family of streptococcal proteins. Interestingly, virtually all of the oral streptococci express antigen I/II but *P. gingivalis* selectively adheres to *S. gordonii* and the related oralis group of streptococci. Neither intact *P. gingivalis* cells nor purified Mfa1 interact with the antigen I/II protein of *Streptococcus mutans*, even though this protein is highly similar to SspB. Furthermore, others have shown that the Mfa1-SspB interaction is essential for adherence of intact *P. gingivalis* to streptococcal cells and the subsequent development of *P. gingivalis* biofilms on streptococcal substrates. Consistent with this, *P. gingivalis* biofilm growth exhibits the same selectivity for streptococcal species. Structure-function analyses on the mechanism of Mfa1-SspB interaction identified a discrete region of SspB, designated BAR (SspB Adherence Region) that was essential for the association of purified Mfa1 or intact *P. gingivalis* cells with *S. gordonii*. Furthermore, specific amino acid residues in the NITVK (SEQ ID NO: 2) sequence contained within BAR are not conserved in the related antigen I/II protein of *S. mutans* and site specific mutagenesis of these amino acids in SspB showed that they were essential for *P. gingivalis* adherence. This provides a mechanism for the selectivity of *P. gingivalis* adhesion.

The adherence of *P. gingivalis* to oral streptococci represents a potentially important target for the development of therapeutic agents, since interfering with the initial colonization of the supragingival biofilm by *P. gingivalis* may prevent it from colonizing and multiplying in its primary niche in subgingival plaque. Indeed, a synthetic peptide encompassing BAR functions as a potent competitive inhibitor ($I_{50}$ of approximately 1.3 µM) of *P. gingivalis* adherence to *S. gordonii* cells and blocks the formation of *P. gingivalis* biofilms. In addition, screening a combinatorial peptide library in which amino acids in the NITVK (SEQ ID NO: 2) sequence of BAR were substituted with all other common L-amino acids defined physicochemical characteristics of the interacting interface of SspB and Mfa1 and suggested that peptides or peptidomimetics with higher specific inhibitory activity than BAR could be developed. Based on these previous findings, we report here that a synthetic BAR peptide containing amino acid substitutions in the NITVK (SEQ ID NO: 2) sequence functions as a more potent competitive inhibitor of *P. gingivalis* adherence and biofilm formation and has higher α-helical content than BAR. We also show that a second structural motif in BAR (KKVQDLLKK (SEQ ID NO: 13)) contributes to *P. gingivalis* adherence. The structural and functional characteristics of this motif, together with the NITVK (SEQ ID NO: 2) region suggest that streptococcal-*P. gingivalis* adherence is driven by a domain in SspB that resembles the eukaryotic nuclear receptor (NR) box protein-protein interacting domain. These motifs are conserved in oral streptococci that interact with *P. gingivalis* but have diverged in the antigen I/II of *S. mutans*.

Materials and Methods.

Growth of bacterial strains. *P. gingivalis* ATCC 33277 was grown in reduced trypticase soy broth (Difco) supplemented with 0.5 percent yeast extract, 1 µg/ml (final concentration) menadione, and 5 µg/ml (final concentration) hemin. Twenty five milliliters of media were reduced for 24 hours under anaerobic conditions by equilibrating in an atmosphere consisting of 10% $CO_2$, 10% $H_2$, and 80% $N_2$. Following equilibration, *P. gingivalis* was inoculated in the media and grown for 48 hours at 37° C. under anaerobic conditions. *S. gordonii*

L-1 was cultured aerobically without shaking in brain heart infusion (BHI) broth supplemented with 1 percent yeast extract for 16 hours at 37° C.

P. gingivalis adherence and biofilm formation. The adherence of intact P. gingivalis to S. gordonii cells and the subsequent formation of biofilms was carried out using an open flow system essentially as previously described by Amorin Daep et al. Infect Immun 74:5756-62 (2006) and Lamont et al. Microbiology 148:1627-36 (2002). The flow reactor comprised a Manostat Carter 4/8 cassette peristaltic pump (Fisher Scientific, Suwanee, Ga.) using 0.89 millimeter platinum-cured silicone tubing (Fisher Scientific, Suwanee, Ga.) and a BST FC 71 flow cell (Biosurface Technologies, Corp, Bozeman, Mont.). A single surface of a 15×40 mm cover glass (Fisher Scientific, Suwanee, Ga.) was coated with 0.22 µm filter sterilized saliva and incubated at 37° C. for 30 minutes. The saliva coated coverglass was then washed with sterile 1×PBS at a flow rate of 6 ml per hour for 30 minutes to remove unbound salivary constituents.

S. gordonii DL-1 cells were harvested by centrifugation at 4000 rpm at 4° C. for 15 minutes and suspended in 25 ml of sterile 1×PBS. S. gordonii cells were labeled with 20 µl of hexidium iodide (1.6 mg/ml, Molecular Probes, Eugene, Oreg.) at 25° C. for 30 minutes in the dark and washed with PBS. Adherence of streptococci to the saliva coated cover glass was carried out by delivering S. gordonii cells to the flow chamber at a flow rate of 6 ml per hour for approximately 2 hours. Following inoculation with S. gordonii, the flow cell was washed with sterile 1×PBS for 30 minutes at 6 ml per hour to remove non-adherent bacteria from the cover glass.

P. gingivalis ATCC 33277 cells were harvested by centrifugation at 4000 rpm at 4° C. for 45 minutes, suspended in 25 ml of sterile 1×PBS, and introduced into the flow cell at a flow rate of 6 ml per hour for 2 hours at 25° C. to allow P. gingivalis to adhere and accumulate on the streptococcal substrate. Flow cells were subsequently washed with sterile 1×PBS to remove non-adherent P. gingivalis cells. To visualize adherent P. gingivalis, rabbit anti-P. gingivalis 33277 polyclonal antibody diluted 3:5000 in 5 ml of sterile 1×PBS was flowed into the cell at a rate of 6 ml per hour. The flow cell was then washed with sterile 1×PBS for 1 hour, reacted with anti-rabbit IgG fluorescein isothiocyanate (FITC) conjugate (Sigma, St. Louis, Mo.) in sterile 1×PBS (1:5000) for 1 hour at 6 ml per hour, and received a final wash with sterile 1×PBS as above. Under these conditions, the streptococci bound to the saliva coated coverglass as a non-confluent layer comprising single cells and small aggregates. P. gingivalis subsequently adhered to and formed distinct microcolonies on the immobilized streptococci. The microcolonies were visualized and quantified by confocal microscopy as described below.

Confocal microscopy and analysis of P. gingivalis biofilms. P. gingivalis-S. gordonii biofilms were visualized using an Olympus FluoView 500 confocal laser scanning microscope (Olympus, Pittsburgh, Pa.) under 600× magnification using an Argon laser for visualization of FITC labeling and the HeNe-G laser to visualize hexidium iodide labeled streptococci. The number and depth of FITC-labeled P. gingivalis microcolonies was determined from 30 to 60 randomly chosen frames using the FluoView software package provided by Olympus. Microcolony depth was determined by performing Z-plane scans from 0 µm to 30 µm above the coverglass surface. P. gingivalis microcolonies that formed on S. gordonii in the absence of peptide inhibitor ranged from 7 to 16 µm in depth under the experimental conditions used.

Inhibition of P. gingivalis adherence and biofilm formation. For adherence/biofilm inhibition experiments, BAR peptide analogs were pre-incubated with P. gingivalis cells at concentrations of 0 to 3.4 µM at 25° C. for 30 minutes. The P. gingivalis-peptide suspension was then introduced into the flow cell for 2 hours at a flow rate of 6 ml per hour as described above and P. gingivalis microcolonies were analyzed by confocal microscopy. Data was analyzed using GraphPad InStat3 (GraphPad Software Co.). A paired T-test was utilized to determine pair-wise statistical differences in colony number and depth between experimental samples and the control reaction that did not contain inhibitor.

Circular dichroism (CD) spectroscopy. CD experiments were carried out at 25° C. using Jasco J-810 spectropolarimeter (Jasco, Easton, Md.). A 40 µl sample of peptide at a concentration of 1.4 mM in filter sterilized 0.1 M phosphate buffer (pH=7.2) was analyzed in a 0.01 cm quartz cuvette (Starna Cells, Inc., Atascadero, Calif.) using the following parameters: sensitivity=100 mdeg, start wavelength=340 nm, end wavelength=180 nm, continuous scanning mode at 200 nm/minute, response=1 second, and bandwidth=1 nm. Nitrogen was flushed into the system at a rate of 31.8 to 42.4 cubic feet/min during each experiment. A total of 10 scans were accumulated and averaged and the appropriate blanks were subtracted from the spectra. The resulting spectra were expressed in molar ellipticity. Normalized CD data were analyzed using $K_2D$ software (on the world-wide web at embl-heidelberg.de/~andrade/k2d.html)) to estimate α-helical, β-sheet, and random coil content.

Peptide synthesis. The synthetic peptides used in this study are listed in FIG. 4. All of the peptides were derived from the sequence of the BAR peptide which comprises residues 1167 to 1193 of the SspB (antigen I/II) protein sequence of S. gordonii. Peptides were synthesized by BioSynthesis, Inc. (Lewisville, Tex.) and were obtained at greater than 85% purity. Prior to use, peptides were suspended at the appropriate concentration in nuclease and protease free water (Fisher Scientific Co., Fairlawn, N.J.).

Secondary structure prediction and sequence comparison. The secondary structure of the synthetic peptides was predicted using the Protein Structure Prediction Server (Psipred, on the world-wide-web at bioinf.cs.ucl.ac.uk/psipred/). Comparison of the BAR region of SspB with sequences in the protein database was carried out using the BlastP program available through NCBI (on the world-wide-web at ncbi.nlm.hif.gov/blast/Blast.cgi). For these searches, the entire SspB polypeptide sequence was used as the query to identify related sequences in the database. An "e" score of 1e-10 for the complete sequence was used as the threshold for significance. Subsequently, the regions corresponding to the BAR sequence in each of the related sequences that were identified were recorded and compiled.

Results

Active site amino acid substitutions in BAR increase its specific anti-biofilm activity. A synthetic peptide (BAR) derived from the SspB protein sequence was previously shown to be sufficient for P. gingivalis adherence to S. gordonii, and in solution this peptide functioned as a potent inhibitor of the P. gingivalis adherence and biofilm formation on streptococcal substrates. Subsequently using a combinatorial approach in which mixtures of peptides were screened for their ability to promote P. gingivalis adherence, Amorin Daep et al. Infect Immun 74:5756-62 (2006) showed that substitution of Arg for $Asn_{1182}$ and Ile for $Val_{1185}$ in the NITVK (SEQ ID NO: 2) region of BAR resulted in increased in vitro adherence of P. gingivalis. To determine if these results could be exploited to produce a more potent inhibitor of P. gingivalis biofilm formation, a derivative of the BAR peptide containing the Arg/$Asn_{1182}$ and Ile/$Val_{1185}$ substitutions (BAR-II) was synthesized and analyzed. As shown in FIG. 5, BAR-II inhibited the adherence and subsequent formation of P. gingivalis microcolonies on the streptococcal substrate by 25% and 82% at peptide concentrations of 0.34 μM and 0.85 μM, respectively. In contrast, the parent BAR peptide inhibited microcolony formation by only 3% and 7%, respectively, at these peptide concentrations. From the dose responses shown, the $I_{50}$ for BAR-II was calculated to be 0.52 μM and was approximately 2.5-fold greater than the $I^{50}$ calculated for the BAR peptide (1.25 μM, which was consistent with the $I_{50}$) of 1.3 μM previously reported for BAR (Infect Immun 74:5756-62). Thus, the BAR peptide that was altered in the NITVK (SEQ ID NO: 2) region interacts with P. gingivalis at higher affinity and functions as a more potent competitive inhibitor of P. gingivalis adherence and biofilm formation.

Data from the combinatorial screen and our previous site specific mutagenesis experiments also indicated that the introduction into NITVK (SEQ ID NO: 2) of amino acids with the potential to disrupt secondary structure (e.g., Pro and Gly) reduced P. gingivalis adherence, suggesting that the secondary structure of BAR may be important for binding. As shown in FIG. 6, the predicted secondary structure of BAR-II does not differ from BAR but the analysis of circular dichroism (CD) spectrographs of BAR and BAR-II indicated that the latter contained significantly greater α-helical content (28% versus 10%) and less β-sheet and random coil in solution, suggesting that the presence of Arg and Ile stabilized the secondary structure of BAR. To determine if BAR-mediated inhibition of P. gingivalis adherence correlates with α-helical content of the peptide, CD spectra were also obtained for a cyclic conformationally constrained BAR peptide (CR-BAR) that was previously shown to be a poor inhibitor of biofilm formation. This peptide (designated as BAR-III for this study) exhibited a specific activity of ~13-fold less than BAR. Unexpectedly, BAR-III also contained 28% α-helix, similar to that of BAR-II (FIG. 6). This suggests that inhibitory activity is independent of secondary structure, or alternatively, that the introduction of Cys to generate BAR-III disrupts a second structural motif that is important for the interaction of BAR with P. gingivalis. To address this, the sequence of BAR was re-examined focusing on the regions that were altered to create BAR-Ill.

The putative α-helical region upstream of NITVK (SEQ ID NO: 2) is also essential for BAR interaction with P. gingivalis. The disulfide bridged peptide BAR-III was synthesized by substituting Cys residues for Leu$^{1177}$ and Leu$^{1191}$. Leu$^{1191}$ is within a region of BAR that is well conserved in the antigen I/II protein of S. mutans which does not interact with P. gingivalis. In contrast, the sequence around Leu$^{1177}$ has diverged from the S. mutans protein. Leu$^{1177}$ is part of a predicted amphipathic α-helix (VXXLL (SEQ ID NO: 3), actual sequence VQDLL (SEQ ID NO: 1)) that resembles the consensus sequence of a known protein-protein interaction domain, the nuclear receptor box (NR-box, consensus LXXLL (SEQ ID NO: 6)) which mediate the interaction of co-activator/repressor proteins with the nuclear receptor family of transcriptional regulators in eukaryotes. Furthermore, other structural characteristics of the VQDLL (SEQ ID NO: 1) region in BAR are consistent with the known properties of the NR box. For example, VQDLL (SEQ ID NO: 1) is flanked by charged amino acids in BAR (Lys$^{1172, 1173, 1179, 1180}$) and charged residue in the corresponding positions in the NR box have been suggested to stabilize the co-activator-NR interaction. The specificity of NR/co-activator interactions is not dictated by the consensus region LXXLL (SEQ ID NO: 6) but by sequences that reside either upstream or downstream of the LXXLL (SEQ ID NO: 6) motif. In BAR, the NITVK (SEQ ID NO: 2) motif resides immediately downstream of VXXLL (SEQ ID NO: 3) and we previously showed that NITVK (SEQ ID NO: 2) is responsible for the selectivity of P. gingivalis adherence to oral streptococci.

Therefore, to determine if the VXXLL (SEQ ID NO: 3) region contributes to the interaction of BAR with P. gingivalis, two decapeptides comprising either the VQDLL (SEQ ID NO: 1) (BAR-IV) or NITVK (SEQ ID NO: 2) (BAR-V) regions, and a 20-mer containing both VQDLL (SEQ ID NO: 1) and NITVK (SEQ ID NO: 2) (BAR-VII) were synthesized and tested as inhibitors of P. gingivalis-S. gordonii adherence and biofilm formation. A decamer (BAR-VI) and a 20-mer (BAR-VIII) derived from the regions of S. mutans antigen I/II that correspond to NITVK (SEQ ID NO: 2) and VQDLL (SEQ ID NO: 1)/NITVK (SEQ ID NO: 2) respectively (see FIG. 4), were also synthesized and used as control peptides since antigen I/II of S. mutans neither interacts with P. gingivalis nor promotes biofilm formation. As shown in FIG. 7A, BAR-VII inhibited P. gingivalis biofilm formation in a dose dependent manner whereas the negative control peptide BAR-VIII was inactive. In contrast, BAR-IV and BAR-V encoding the individual VXXLL (SEQ ID NO: 3) or NITVK (SEQ ID NO: 2) motifs respectively, exhibited no inhibitory activity (FIG. 7B) suggesting that the interaction of BAR with P. gingivalis requires both the VXXLL (SEQ ID NO: 3) and NITVK (SEQ ID NO: 2) motifs. The control S. mutans peptide (BAR-VI) was also inactive.

Figure 8:
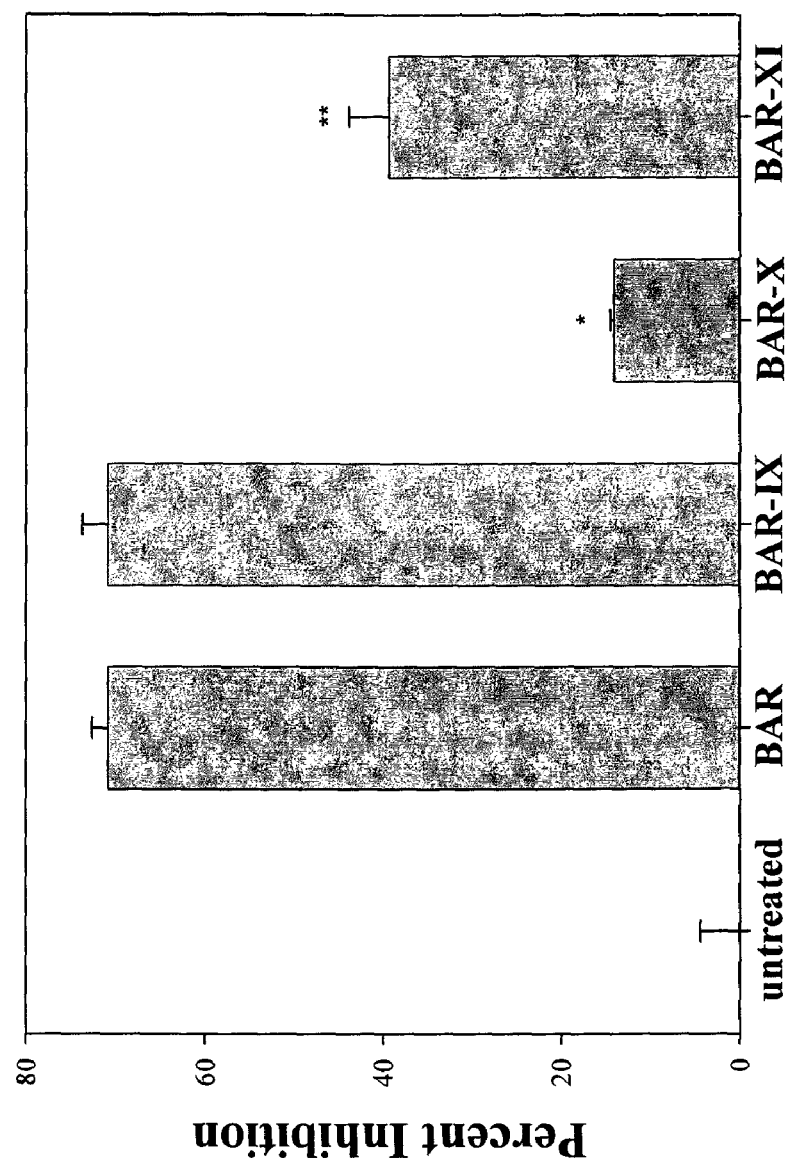
FIG. 8. Amino acid substitutions in the VXXLL (SEQ ID NO:3) motif influence biofilm inhibitory activity of the BAR peptide. Analogs of BAR peptide that were altered at the variable positions in the core VXXLL (SEQ ID NO: 3) sequence (BAR-X), the lysine residues flanking VXXLL (SEQ ID NO: 3) (BAR-XI), or at the hydrophobic Val and Leu residues of VXXLL (SEQ ID NO: 3) (BAR-IX) were synthesized and analyzed for biofilm inhibition as described in Example 2. A functional VXXLL (SEQ ID NO: 3) motif requires the maintenance of α-helicity and positive charge through the region. A single asterisk designates a significant difference where <0.001); a double asterisk indicates p <0.01. Percent inhibition was calculated as follows: ave. microcolonies per frame (control)-ave. microcolonies per frame (experimental)/ave. microcolonies per frame (control). At least thirty independent frames from three separate biofilm cultures were analyzed for each peptide sample.

Functional properties of VXXLL (SEQ ID NO: 3) resemble the NR box. A short hydrophobic, α-helical motif in eukaryotic co-activator proteins (consensus LXXLL (SEQ ID NO: 6) is essential for their interaction with the cognate nuclear receptor. This interaction is stabilized by hydrogen bonding and/or charge-charge interactions of amino acids flanking LXXLL (SEQ ID NO: 6) with the ligand binding domain (LBD) of the nuclear receptor. To determine if VXXLL (SEQ ID NO: 3) in BAR functions similarly to the NR box, we examined the contribution of each of these characteristics, i.e., the α-helical content, the hydrophobic character of VXXLL (SEQ ID NO: 3), and the contribution of charged amino acids flanking VXXLL (SEQ ID NO: 3) in the interaction of BAR with P. gingivalis. As shown in FIG. 8, the BAR-X peptide in which the internal variable residues in VXXLL (SEQ ID NO: 3) were altered to Pro and Gly (i.e., VPGLL (SEQ ID NO:7)) was a poor inhibitor of biofilm formation (~15% inhibition at 3.38 μM) relative to the control BAR peptide (~75% inhibition at 3.38 μM). This suggests that amino acids with the potential to disrupt α-helix strongly reduce the potency of the peptide inhibitor. A reduction in inhibitory activity was also obtained when the positively charged Lys residues flanking VXXLL (SEQ ID NO: 3) were altered to Asp in BAR-XI (40% inhibition versus 75% for BAR). Secondary structural predictions of the modified peptide suggested that the Asp/Lys substitutions did not alter the overall secondary structure of BAR. Therefore, the basic residues that reside upstream and/or downstream of VXXLL (SEQ ID NO: 3) also appear to contribute to the interaction of BAR with P. gingivalis. However, reducing the hydrophobicity of VXXLL (SEQ ID NO: 3) by substituting neutral or charged residues for the hydrophobic amino acids (e.g., VXXLL (SEQ ID NO: 3) to DXXND (SEQ ID NO:8)) without changing the predicted α-helical character of VXXLL (SEQ ID NO: 3) had no effect on inhibitory activity as observed for BAR-IX. Thus, the α-helical content and the presence of basic residues play a greater role in the association of BAR with P. gingivalis than does the hydrophobic character of the putative VXXLL (SEQ ID NO: 3) α-helix.

Distribution of VXXLL (SEQ ID NO: 3) and NITVK (SEQ ID NO: 2) among streptococcal sequences. To determine if the NR box-like VXXLL (SEQ ID NO: 3) motif and the NITVK (SEQ ID NO: 2) region of BAR are conserved in other antigen I/II-related polypeptides, a BlastP search was conducted using the SspB sequence as query. Fifteen different deduced polypeptide sequences were identified from ten different streptococcal species and one species of *Lactococcus*. The regions of these sequences that correspond to the BAR peptide are compared in FIG. 9. The NITVK (SEQ ID NO: 2) sequence is conserved only in *S. gordonii, S, oralis* and *S. sanguinis*. All of the other antigen I/II sequences contained substitutions of Gly for $Asn^{1182}$ or Pro for $Val^{1185}$, or both in the region corresponding to NITVK (SEQ ID NO: 2). These substitutions in NITVK (SEQ ID NO: 2) were previously shown in our combinatorial screen, and by site specific mutagenesis of the sspB sequence to completely inhibit adherence of *P. gingivalis*. Consistent with this, each of the species containing NITVK (SEQ ID NO: 2) in antigen I/II adhere to *P. gingivalis* and support biofilm formation similarly to *S. gordonii* (not shown). Thus, the presence and distribution of the NITVK (SEQ ID NO: 2) motif is consistent with the ability of *P. gingivalis* to selectively adhere to streptococci and form biofilms.

The VXXLL (SEQ ID NO: 3) motif is also conserved only in *S. gordonii, S, oralis* and *S. sanguinis*. However, NR box-like motifs (underlined in FIG. 9 and characterized by Hy-X-X-Hy-Hy (SEQ ID NO:9), where Hy is a hydrophobic amino acid) are present in all of the other antigen I/II-related sequences as well. A VXXML (SEQ ID NO: 4) motif is present in antigen I/II proteins of *S. downei, S. sobrinus* and *S. criceti*, and VXXVL (SEQ ID NO: 5) is found in *S. intermedius* and *L. lactis*. In each case, the NR box-like sequence is flanked by one or more charged residues and resides 2 residues downstream from a conserved proline. This motif is also separated from the NITVK (SEQ ID NO: 2) (or related motif) by a single conserved alanine. Thus, the overall structure and spacing of the BAR peptide region of antigen I/II is well conserved but variable residues that may influence the function of the proteins exist in both the VXXLL (SEQ ID NO: 3) and NITVK (SEQ ID NO: 2) regions.

Discussion.

To colonize the oral cavity, *P. gingivalis* can adhere to select species of oral streptococci and/or *Fusobacterium nucleatum* in supragingival plaque before becoming established in its primary niche in the subgingival pocket. The adherence and the subsequent formation of *P. gingivalis* biofilms on streptococci is mediated by a protein-protein interaction between the minor fimbrial antigen Mfa1 and a discrete region the streptococcal SspB (antigen I/II) polypeptide. Daep et al. (2006, Infect Immun. 74(10), 5756-5762) previously showed that a peptide (BAR) comprising the interacting region of SspB was a potent inhibitor of *P. gingivalis/S. gordonii* adherence and subsequent formation of biofilms and that some combinatorial mixtures of peptides containing substitutions in the NITVK (SEQ ID NO: 2) active site region of BAR resulted in increased *P. gingivalis* adherence. We have now shown that a pure synthetic et al functions as a ~2.5-fold more potent competitive inhibitor of *P. gingivalis* adherence and biofilm formation. This suggests that altering the NITVK (SEQ ID NO: 2) sequence in BAR to RITIK (SEQ ID NO:10) (by substituting Arg for $Asn^{1182}$ and Ile for $Val^{1185}$) increases the affinity of its interaction with Mfa1. Other potential adherence-promoting amino acid substitutions that were predicted by the combinatorial screening of Daep et al are currently being tested, e.g., Lys or Ser for $Asn^{1182}$ and Phe for $Val^{1185}$. Interestingly, the Lys/$Asn^{1185}$ substitution occurs naturally in several other antigen I/II-like proteins expressed by other non-oral streptococci and lactococci (FIG. 9). However, this substitution occurs in conjunction with a Pro/$Val^{1185}$ alteration which we have previously shown to completely inhibit the SspB-Mfa1 and *P. gingivalis*-BAR peptide interaction. Indeed, comparison of antigen I/II amino acid sequences deduced from the available streptococcal qenome sequences indicates that Pro is the consensus residue at position 1185 (FIG. 9). Valine is present only in the antigen I/ll proteins expressed by organisms in the oralis group of streptococci, which interact with *P. gingivalis*.

In the absence of a three dimensional structure of the SspB binding pocket of Mfa1, it is difficult to determine mechanistically how the Arg/$Ase^{1182}$ and Ile/$Val^{1185}$ substitutions affect the interaction of the proteins. In silico predictions suggest that the substitutions do not alter the secondary structure of the BAR peptide but CD analysis indicated that BAR-II contained significantly more α-helical content than BAR. One possible explanation is that the amino acid substitutions reduce flexibility and stabilize the structure of the peptide in an "active" conformation in solution. Consistent with this, a conformationally constrained disulfide linked BAR-Ill in which $Leu^{1177}$ and $Leu^{1191}$ were substituted with Cys exhibited an α-helical content similar to BAR-II. However, BAR-Ill was a poor inhibitor of *P. gingivalis* biofilm formation and our results now suggest that the poor inhibitory activity of BAR-Ill arises from the substitution of Cys for $Leu^{1177}$ which disrupts a second important region of BAR that is required for *P. gingivalis* adhesion. Indeed, $Leu^{1177}$ is part of a motif, VXXLL (SEQ ID NO: 3), that resembles a known protein-protein interacting domain, the nuclear receptor (NR) box found in co-activators of nuclear receptors of eukaryotes. Thus, our results indicate that both the VXXLL (SEQ ID NO: 3) and NITVK (SEQ ID NO: 2) motifs of BAR participate in binding to Mfa1.

Figure 10:
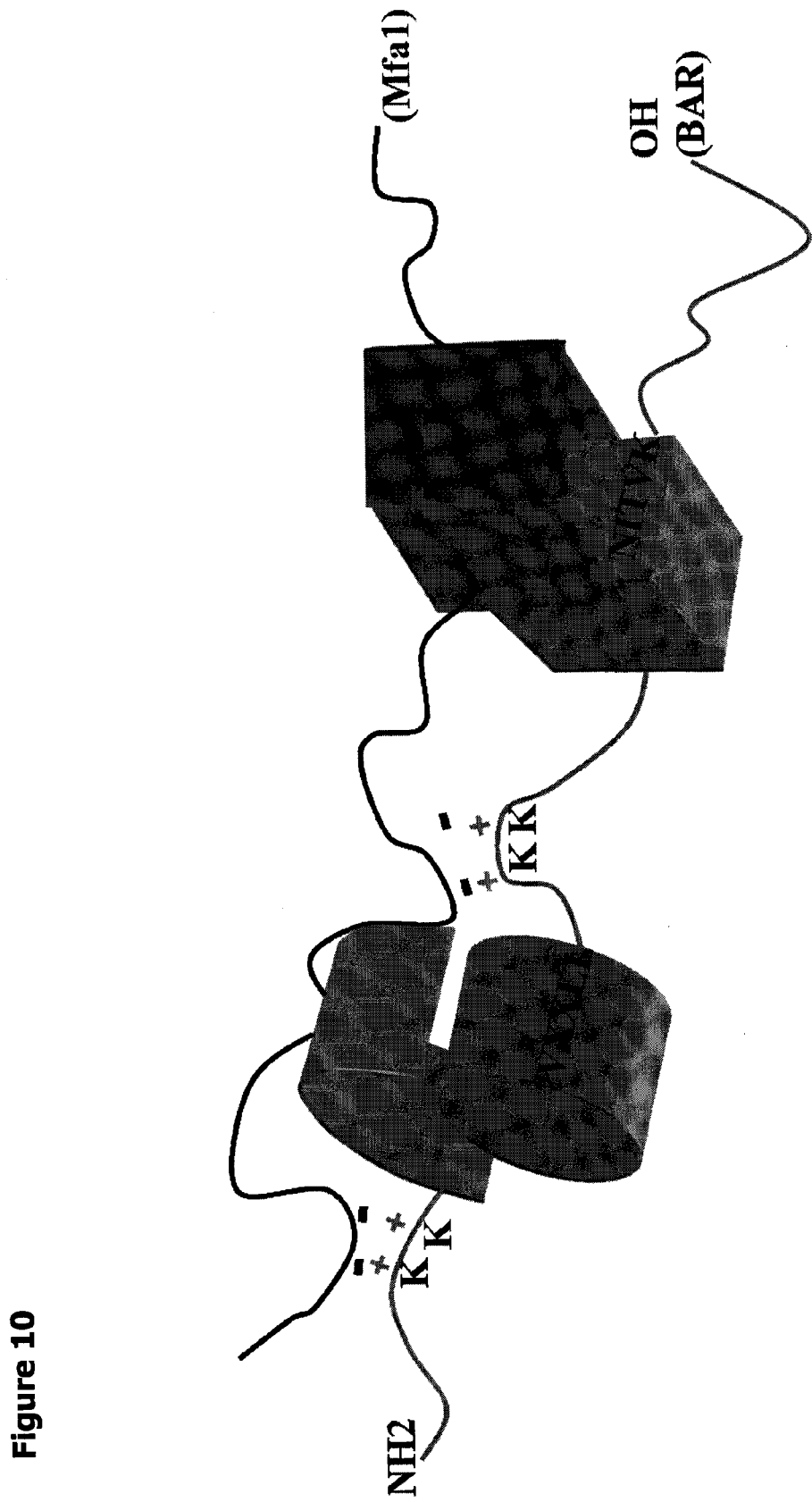
FIG. 10. Schematic of the interaction of SspB and Mfa1. The adherence of P. gingivalis to streptococci requires the VXXLL (SEQ ID NO: 3) and NITVK (SEQ ID NO: 2) motifs of SspB. The initial interaction between SspB (bottom) and Mfa1 (top) may occur via the amphipathic, α-helical VXXLL (SEQ ID NO: 3) motif. This interaction may be stabilized by a charge clamp that involves hydrogen bonding or electrostatic interactions between the lysine residues that flank VXXLL (SEQ ID NO: 3) and adjacent amino acids in Mfa1. The results suggest that specificity of the Mfa interaction with antigen I/II proteins from oralis streptococci is dictated by the downstream NITVK (SEQ ID NO: 2) motif and that alteration of $Asn^{1182}$ and $Val^{1885}$ can either facilitate or inhibit the association of SspB and Mfa1.

The NR box is a protein-protein interacting domain that is present in co-activator (CoA) proteins that interact with nuclear receptors in eukaryotic organisms. It is comprised of a hydrophobic or amphipathic α-helical motif with a consensus sequence of LXXLL (SEQ ID NO: 6) or FXXFF (SEQ ID NO:11), although Val is tolerated in place of $Leu^{+1}$ and Met can functionally replace $Leu^{+4}$ (where, the core motif is numbered +1 to +5 from left to right). The VXXLL (SEQ ID NO: 3) motif in BAR is a predicted amphipathic α-helix and its sequence and structural properties are consistent with the consensus NR box. Furthermore, the introduction of amino acids with the potential to disrupt the secondary structure of VXXLL (SEQ ID NO: 3) reduced the specific inhibitory activity of BAR, suggesting that the putative α-helical character of VXXLL (SEQ ID NO: 3) is important for the interaction of BAR with Mfa1. In addition, the association of the CoA with the NR box of the nuclear receptor ligand binding domain (LBD) is stabilized by a charge clamp that arises from electrostatic or hydrogen bonding interactions that occur between charged residues flanking either or both sides of the NR box and amino acids in the LBD. The VXXLL (SEQ ID NO: 3) motif is also flanked by Lys residues at the −1, −2, +6 and +7 positions and the substitution of acidic amino acids at these positions resulted in reduced inhibitory activity, suggesting that the BAR-Mfa1 interaction may also be stabilized by a charge clamp involving the flanking Lys residues. Finally, the specificity of the CoA-NR interaction is driven by amino acids that reside either upstream or downstream from the core LXXLL (SEQ ID NO: 6) motif. The VXXLL (SEQ ID NO: 3) motif in BAR resides immediately upstream from NITVK (SEQ ID NO: 2), which we previously showed was responsible for the specificity of *P. gingivalis* adherence to the oralis group of streptococci. Together, these results suggest that *P. gingivalis* adherence to streptococci is mediated by a protein-protein interacting domain of SspB (antigen I/II) that resembles the eukaryotic NR box domain. To our knowledge, this is the first identification of a functional NR box-like protein-protein interaction motif in a prokaryotic system. Based on these results, a model depicting the interacting interface between SspB and Mfa1 is shown in FIG. 10.

As discussed above, the NITVK (SEQ ID NO: 2) motif is conserved only in the oralis group of streptococci. The remaining antigen I/II-like proteins each possess Gly/Asn$^{1182}$ and/or Pro/Val$^{1185}$ substitutions that are incompatible with *P. gingivalis* adherence. Interestingly, the VXXLL (SEQ ID NO: 3) motif is also present only in the oralis streptococci, supporting our finding that both motifs are required for *P. gingivalis* adherence. However, most of the other antigen I/II-like proteins possess a motif related to VXXLL (SEQ ID NO: 3) that also resembles the consensus NR box, and the amino acids that occupy the +1, +4 and +5 positions fall within those that are functionally tolerated in the NR box. The two exceptions are antigen I/II-like proteins of *S. suis* and *S. agalactiae*, which contain Lys at the +4 position (see FIG. 9). Given the presence and conservation of this motif in antigen I/II proteins, it is tempting to speculate that they may also mediate protein-protein or interspecies interactions in these organisms and that the specificity of these interactions may be dictated by sequence variability that is present in the downstream motif corresponding to NITVK (SEQ ID NO: 2).

In general, there exist few if any therapeutic compounds that are targeted towards specific pathogenic organisms in the oral cavity. However, the potent inhibitory activity exhibited by BAR raises the possibility that peptide or peptidomimetic analogs of BAR could be developed to reduce *P. gingivalis* colonization of supragingival plaque. Interestingly, the NR box has been targeted for drug intervention since biochemical studies suggested that the CoA-NR interaction could be blocked by small peptides containing the LXXLL (SEQ ID NO: 6) motif. In addition, others have shown that disulfide and thioether-bridged side chain cyclization induced α-helicity in peptides comprising the LXXLL (SEQ ID NO: 6) motif and that these peptides modulated estrogen receptor activity. Thus, modification of the VXXLL (SEQ ID NO: 3). and NITVK (SEQ ID NO: 2) motifs, either to constrain flexibility of the peptide or to maintain its α-helical character might further improve the specific inhibitory activity of BAR peptide analogs. Another consideration in developing BAR peptide as a potential therapeutic agent against *P. gingivalis* is its susceptibility to proteolytic degradation. *P. gingivalis* is a highly proteolytic organism and cell free extracts from *P. gingivalis* cultures degrade BAR. However, it is interesting that the addition of minor fimbrial antigen (Mfa1, the receptor for BAR) to these extracts protects the peptide from degradation (D. Demuth, unpublished), suggesting that the affinity of BAR for Mfa1 is greater than for the proteases secreted by *P. gingivalis*. This provides an explanation as to why BAR competitively inhibits *P. gingivalis* adherence to streptococci in the presence of proteolytic activities.

In summary, our studies have expanded the interacting interface between the SspB and Mfa1 proteins to include the predicted VXXLL (SEQ ID NO: 3) α-helix. Together with the NITVK (SEQ ID NO: 2) motif, this domain resembles the eukaryotic NR box protein-protein interaction domain and this similarity may provide a foundation upon which to generate additional analogs of the BAR peptide that may be more potent anti-biofilm compounds by targeting the initial adherence of *P. gingivalis* to oral streptococci.

EXAMPLE 3

Disruption of a Pre-Existing Biofilm by Treatment with BAR

Figure 11:
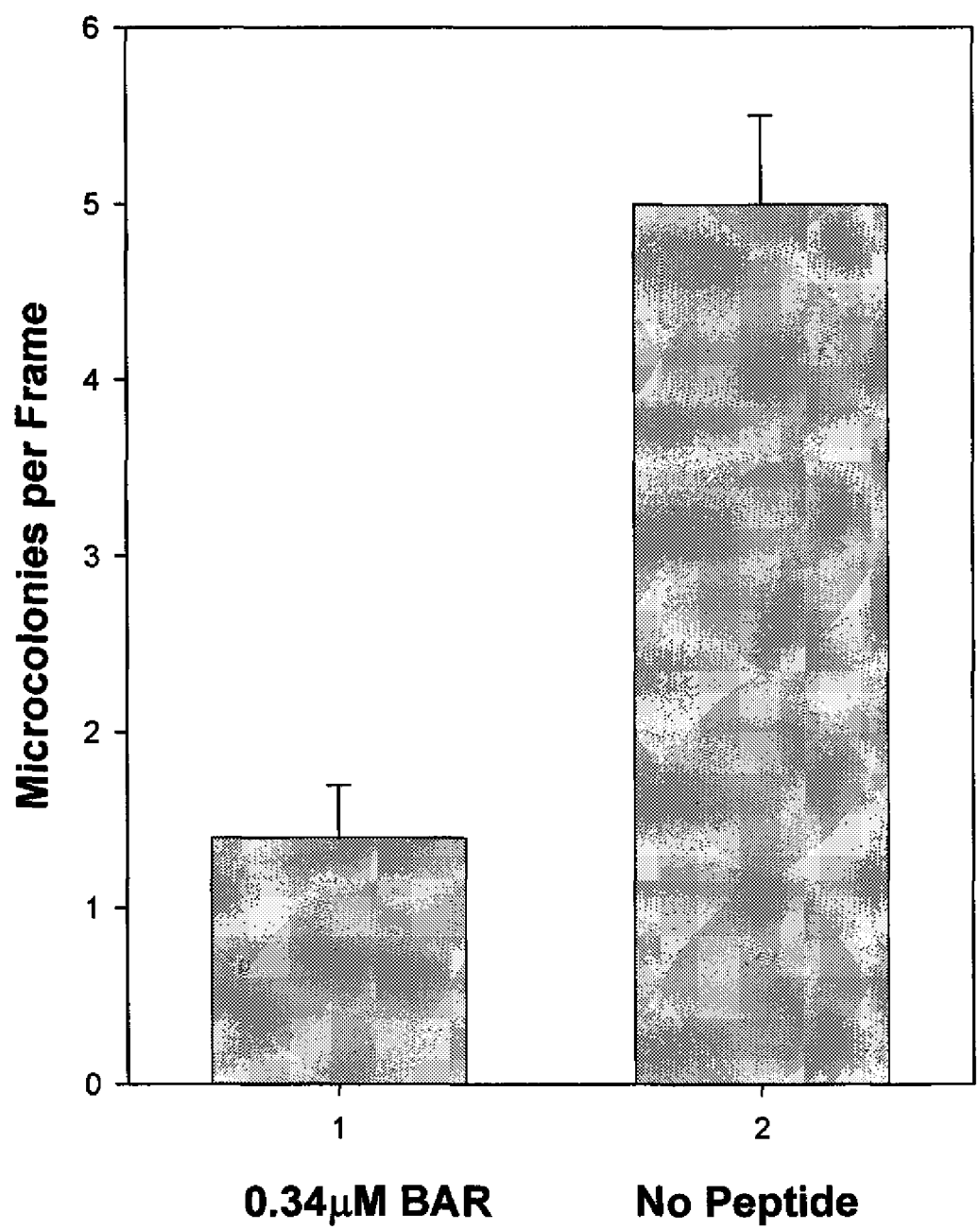
FIG. 11. Treatment of an existing P. gingivalis biofilm with BAR resulted in a significant reduction of microcolonies over the control culture that was exposed to medium without BAR.

In the examples above and in previous studies by the inventor (Infect Immun. 2006. 74:5756-5762), it was shown that pre-treatment of *P. gingivalis* cells with BAR prevented its adherence to oral streptococci and inhibited the formation of a biofilm. However, to develop this peptide for therapeutic use against periodontal disease it would also be beneficial to disrupt existing *P. gingivalis* biofilms in the oral cavity. To determine if BAR disrupts an existing *P. gingivalis* biofilm, biofilms were generated as in Example 2 but without pre-treatment with BAR. After formation of the *P. gingivalis* biofilm, it was exposed for up to 2 hours with BAR peptide at a concentration of 10 µg/ml. Analysis of the results by confocal microscopy were as described in Example 2. As shown in FIG. 11, treatment of an existing *P. gingivalis* biofilm with BAR resulted in a significant reduction of microcolonies over the control culture that was exposed to medium without BAR. Thus, BAR peptide can effectively disrupt a pre-formed biofilm, and is effective for controlling pre-existing *P. gingivalis* populations in the oral cavity.

EXAMPLE 4

Peptide Mimetics

Various experimental techniques yield peptides that are biologically active but have unfavorable pharmacological properties, such as difficulty to produce in large quantities, and sensitive to protease digestion. Because peptides are often poor drug candidates, the need arises for bioequivalent compounds with better pharmacological properties. These peptide mimics are inexpensive nonpeptidic oligomers and polymers that adopt amphiphilic secondary structures and exhibit potent and selective targeted activity. Starting from a known spatial structure of a natural peptide template, the aim is to find compounds that mimic the function of a peptide but have improved cellular transport properties, low toxicity, few side effects and more rigid structures as well as protease resistance. These functionally and structurally similar organic compounds are called peptide mimetics. Peptide mimetics may have several potential advantages over native peptides, such as increased stability, increased lipophilicity, increased rigidity, decreased size, and affordability of production.

Various methods exist for developing peptide mimetics. These include computational as well as experimental screening methods. One method is to identify small peptides that are essential for the interactions of the protein. Subsequently, mimetics for these peptides are designed that can be used as drugs. On the basis of a known protein structure, scaffolding templates for binders can also be constructed and then optimized using different methods. Peptide mimetics for BAR peptides encompass organic molecules, carbohydrates, or modified peptides. The important issue is that the compound must maintain the functional shape and chemistry of BAR. The compound must mimic the helical content of BAR and have the physical and chemical properties of the KKVXX-LLKK (SEQ ID NO:12) and NITVK (SEQ ID NO: 2) regions described in the Examples above. Candidate molecules are screened using the antimicrobial assays described for the BAR peptides.

EXAMPLE 5

Further Modifications to the BAR Peptide

As discussed above, the synthetic peptide BAR was derived from an internal region of the antigen I/II (SspB) expressed on the outer membrane of the oral bacteria *Streptococcus gordonii*. The peptide has been shown to be a potent competitive inhibitor for the adherence of the periodontal pathogen *Porphyromonas gingivalis* to an existing *S. gordonii* biofilm. The small, 27 amino acid peptide binds to the minor fimbrial antigen (Mfa1) expressed by *P. gingivalis* and competitively inhibits its interaction with the streptococcal SspB protein. This provides a rationale for further development and design of the peptide as a possible anti-biofilm agent and potential therapeutic agent against periodontal disease.

A proline residue in BAR is important for inhibition of *P. gingivalis* adherence to streptococci. Binding of the BAR peptide to Mfa1 and to *P. gingivalis* is driven by two independent motifs of sequences KKVQDLLKK (SEQ ID NO: 13) and NITVK (SEQ ID NO: 2). The former sequence is predicted to be α-helical and this structure is important for BAR activity. We have also shown that specific amino acid substitutions in these sequences increases the inhibitory activity of BAR. Comparison of the BAR sequence with other streptococcal antigen I/II proteins identified a conserved proline residue within the predicted α-helical region of the peptide, situated immediately upstream of KKVQDLLKK (SEQ ID NO: 13). Substituting glutamine for this proline residue (this peptide was designated BAR-XIII) resulted in the loss of inhibitory activity even when a concentration was used that was 5-fold higher than that required for complete inhibition of adherence by the parent BAR peptide (see FIGS. 12 and 13). This result suggests that the praline within the α-helical region of BAR plays a critical structural role in the binding activity of the peptide to *P. gingivalis*.

Constraining structural flexibility of BAR increases inhibitory activity. Because small peptides may be structurally flexible in solution, it is possible that by constraining structural flexibility one can lock the peptide into its active conformation and increase its biologic activity. Therefore, we limited the structural flexibility of BAR by synthesizing a cyclic disulfide analog of the peptide in which leucine residues at the +1 and +24 positions in BAR were changes to cystiene residues. Analysis of this peptide showed that it possessed greater adherence inhibitory activity than BAR (see FIG. 14). This suggests that further modifications designed to limit structural flexibility in the peptide may further increase the inhibitory activity of the peptide.

Figure 16:
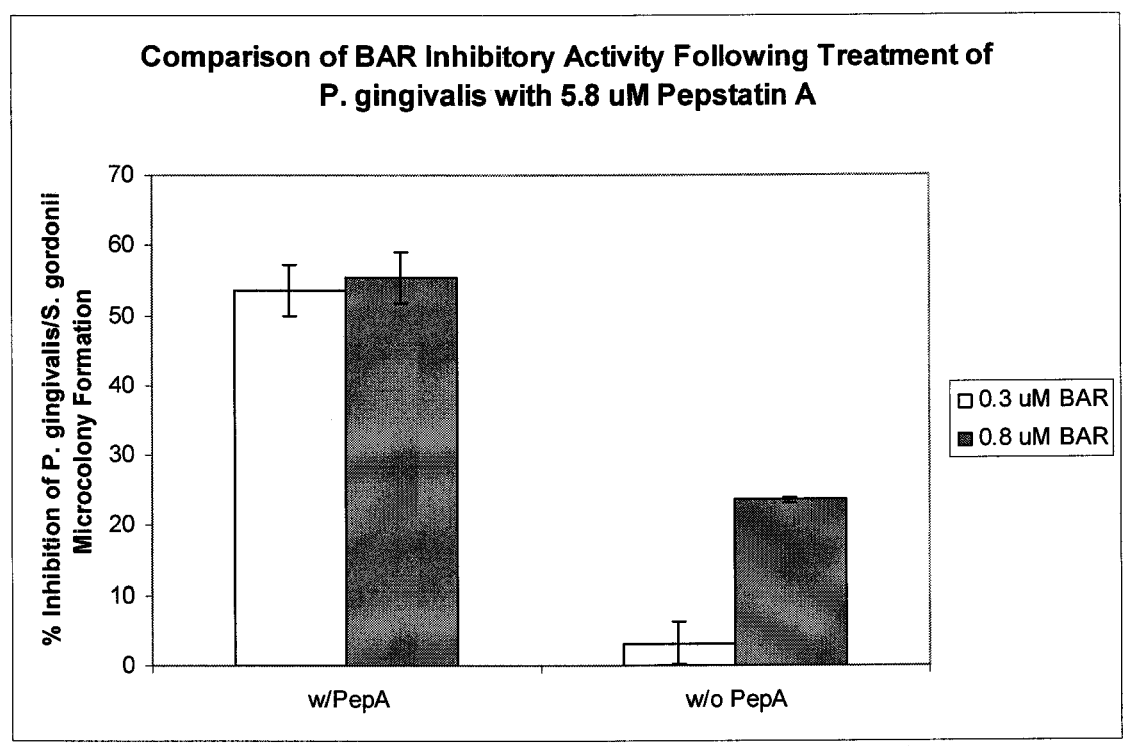
FIG. 16. Inhibition of *P. gingivalis/S. gordonii* biofilm by BAR following the pre-treatment of *P. gingivalis* with Pepstatin A. Pre-treatment of *P. gingivalis* with 5.8 μM of the protease inhibitor Pepstatin A prior to pre-treatment with BAR resulted in an increase in the inhibitory activity of the BAR peptide. A significant difference (a; P<0.05) in microcolony numbers was observed between 0.8 μM BAR w/o Pepstatin A and 0.3 μM BAR w/Pepstatin A. Similarly, pre-treatment of *P. gingivalis* with Pepstatin A prior the treatment with 0.8 μM BAR resulted in a significant decrease (b, c; P<0.01) in the total microcolony formation compared with 0.8 μM BAR without Pepstatin A. A current total of at least 20 independent frames from 2 separate biofilms have been analyzed. At least 3 separate biofilm experiments are targeted for each peptide concentration. The BAR peptide concentrations will be titered until the total microcolony number for the BAR treated with Pepstatin A equal the microcolony count for 0 μM BAR peptide.

Limiting proteolytic degradation of BAR. *P. gingivalis* expresses several proteases including Arg- and Lys-gingipains. We have shown that BAR is susceptible to degradation by proteases produced by *P. gingivalis* in vitro (FIG. 15A) but that the presence of Mfa1 protects BAR from proteolytic cleavage (see FIG. 15B). This suggests that the binding affinity of BAR for Mfa1 is greater than its affinity for proteases. It is also possible that the specific activity of BAR can be increased by preventing or limiting proteolytic degradation of the peptide. To test this possibility, we examined several protease inhibitors to determine if they reduced protease activity of *P. gingivalis* and protected BAR from proteolytic degradation. The most active protease inhibitor was found to be pepstatin A. To determine if the presence of pepstatin A influences the adherence inhibitory activity of BAR *P. gingivalis* was incubated with streptococci in a 5.8 µM solution of pepstatin A and its inhibition of *P. gingivalis* biofilm formation was compared to BAR peptide without pepstatin A. As shown in FIG. 16, the specific inhibitory activity of BAR was almost 10-fold higher in the presence of pepstatin A. An approximate 50% inhibitory activity was observed for 0.3 µM BAR+pepstatin A compared with 5% inhibition when *P. gingivalis* was pre-treated with 0.3 µM BAR alone. Thus, reducing proteolytic degradation of BAR increases its anti-biofilm activity. Current experiments will titer the BAR concentrations until no remaining inhibitory activity is observed for the peptide.

Determining the three dimensional structure of BAR. Determining the three dimensional structure of BAR will facilitate the synthesis of non-peptide mimetic compounds that may possess the potent anti-biofilm activity of BAR. The production of such compounds will allow for more extensive structural modifications to improve the activity and will decrease production costs, facilitating increased marketability for the products. Current studies to identify the three dimensional structure of the BAR peptide in solution are underway using two approaches, high resolution nuclear magnetic resonance imaging and x-ray crystallography. In conjunction with the Naval Research Laboratories, we will use nmr to determine the 3D solution structure of the BAR peptide. In addition, we have initiated studies to crystallize BAR bound to Mfa1. Crystals have been successfully obtained and initial studies to determine how clearly they diffract are underway.

Inhibition of *P. gingivalis* biofilms by BAR in vivo. Current experiments are also underway to use the BAR peptide as a biofilm inhibitor in a mouse model of periodontitis. Mice will first be orally infected with *S. gordonii* to provide a suitable microbial substrate for the development of *P. gingivalis* biofilms. Subsequently, *P. gingivalis* will be introduced into the oral cavity of mice, either in the presence or absence of BAR peptide or BAR peptide analogs. The extent of colonization by *P. gingivalis* will be followed over time by culturing oral microbial samples obtained from the infected mice. In addition, alveolar bone loss in the maxilla and mandibles of mice induced by *P. gingivalis* infection will be measured. The successful implementation of the in vivo studies will provide a rationale for proceeding to further develop and use the BAR peptide as a biofilm inhibitor in a clinical setting and potential therapeutic agent against diseases associated with *P. gingivalis* colonization.

EXAMPLE 6

Role of *Porphyromonas Gingivalis* Proteinases in the Proteolysis of BAR

A potential obstacle in developing BAR peptide as a targeted anti-*P. gingivalis* compound is its susceptibility to proteolytic degradation. Indeed, *P. gingivalis* is asaccharolytic, utilizes peptides as a carbon source and produces several proteases, including lysine and arginine specific gingipains.

In this Example, the inventors show that BAR peptide is degraded when incubated with intact *P. gingivalis* cells or culture supernatant and that the Lys gingipain (Kgp) is the protease that is primarily responsible. However, BAR peptide is significantly protected from degradation upon addition of purified Mfa1, its *P. gingivalis* receptor suggesting that BAR interacts with Mfa1 at higher affinity than the Lys gingipain. Degradation of BAR peptide by *P. gingivalis* was also eliminated by the addition of 6 µM pepstatin A. Finally, the specific anti-adherence activity of BAR in dual species *P. gingivalis-S. gordonii* biofilm cultures was increased by approximately 3-fold in the presence of pepstatin A. These results suggest that analogs of BAR that resist Lys-gingipain mediated proteolysis are significantly more potent inhibitors of *P. gingivalis* adherence and biofilm formation.

Materials and Methods.

Growth of bacterial strains. *P. gingivalis* bacteria strains were grown in reduced trypticase soy broth (Difco) containing 5 grams per liter yeast extract and supplemented with 1 µg/ml menadione, and 5 µg/ml (final concentration) hemin. *P. gingivalis* was inoculated in pre-reduced medium and grown for 48 hours at 37° C. in an atmosphere consisting of 10% $CO_2$, 10% $H_2$, and 80% $N_2$. For the gingipain mutant strains, antibiotics were added to the medium where necessary (see Table 2). *S. gordonii* DL-1 was cultured aerobically without shaking in brain heart infusion (BHI) medium supplemented with 1 percent yeast extract for 16 hours at 37° C.

TABLE 2

Porphyromonas gingivalis strains

| Strain | Background Strain | Genotype | Antibiotic Resistance |
|---|---|---|---|
| 33277 | ATCC strain | WT | none |
| E8 | W50 | rgpA$^-$/rgpB$^-$ | Clindamycin/Tetracycline |
| KDP129 | 33277 | kgp$^-$ | Tetracycline/Erythromycin |
| KDP128 | 33277 | rgpA$^-$/rgpB$^-$/kgp$^-$ | Tetracycline/Erythromycin |
| SMF1 | 33277 | mfa1$^-$ | Tetracycline |

Aduse-Opoku et al. Generation of Lys-gingipain protease activity in *Porphyromonas gingivalis* W50 is independent of Arg-gingipain protease activities. Microbiology. 146: 1933-1940 (2000).

Expression and purification of Mfa1. Recombinant Mfa1 protein was produced by PCR amplification of the mfa1 coding sequences on the *P. gingivalis* 33277 chromosomal DNA using primers designed from the TIGR genome sequence. The amplification product was cloned into the pET-30 expression system (Novagen) with the resulting plasmid encoding the full-length Mfa1 protein containing a C-terminal pentahistidine tag (SEQ ID NO: 58). After induction in *E. coli*, rMfa was purified by chromatography over an Ni+2 metal chelation resin and by elution with imidazole. Purity was assessed by sodium dodecyl sulfate-polyacrylamide gel electrophoresis (SDS-PAGE).

Figure 17:
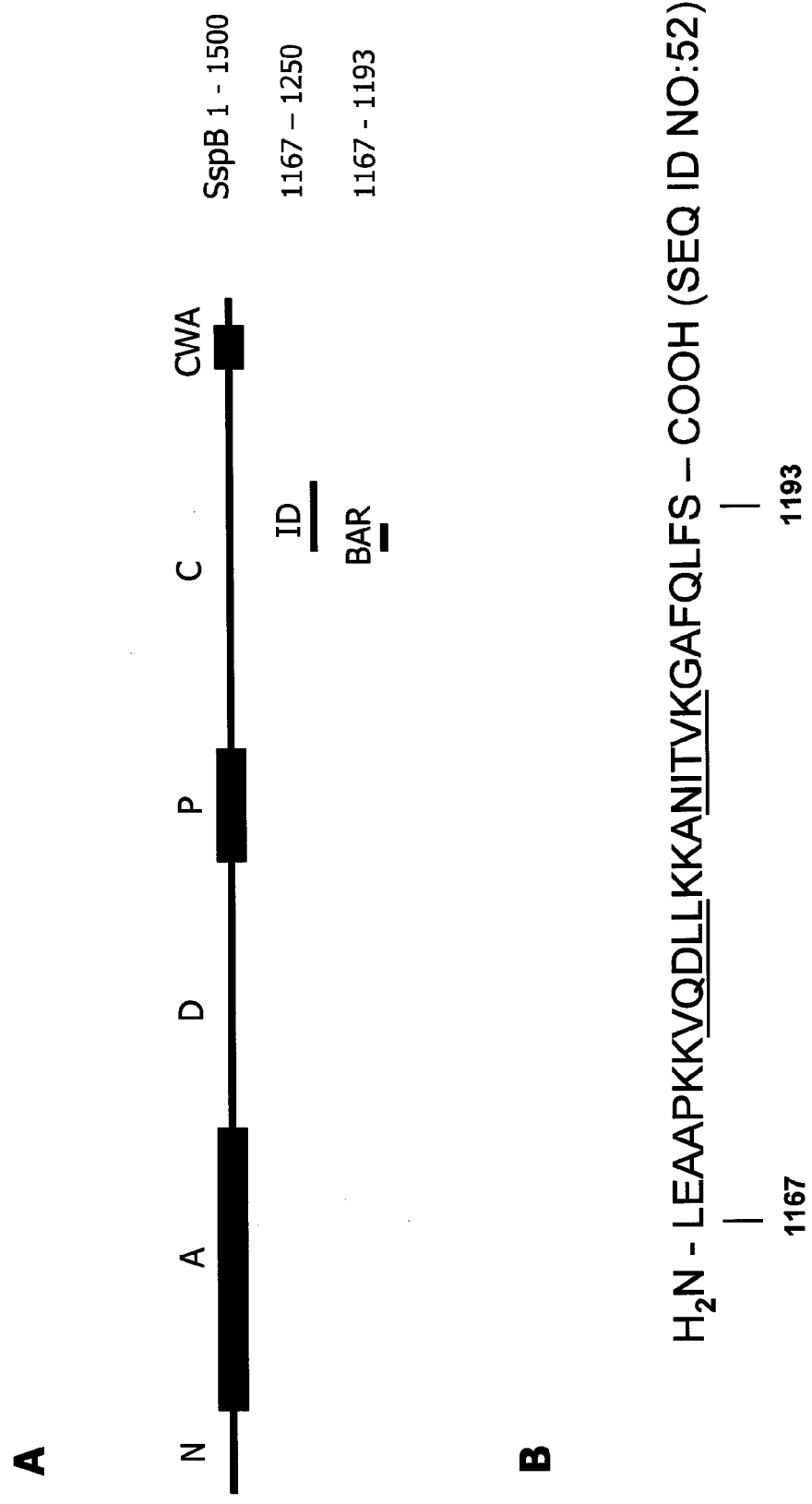
FIG. 17. Streptococcal antigen I/II and the location of BAR peptide. A) SspB, the antigen I/II peptide of *S. gordonii* is 1500 amino acids in length and possesses the conserved structural elements common to most antigen I/II polypeptides: N, N-terminal region; A, alanine-rich repeat domain; D, divergent domain; P, proline rich repeat domain; C, conserved C-terminal region; CWA, cell wall anchoring domain. Residues 1167-1250 in the conserved C-terminal region of SspB represent the interacting domain (ID) and were previously shown to mediate adherence of *P. gingivalis* to *S. gordonii*. BAR peptide comprises residues 1167-1193 of ID and inhibits *P. gingivalis* adherence and formation of biofilms on streptococcal substrates. B) The primary sequence of BAR peptide. The two functional amino acid motifs in BAR, VQDLL (SEQ ID NO: 1) and NITVK (SEQ ID NO: 2) are underlined.

Proteolytic degradation of BAR by *P. gingivalis*. The sequence of the synthetic peptide comprising the BAR region of SspB (antigen I/II) is shown in FIG. 17. One milliliter of mid-exponential phase cultures of *P. gingivalis* SMF, *P. gingivalis* KDP128, *P. gingivalis* KDP129, or *P. gingivalis* E8 was centrifuged at 8000 rpm for 5 minutes at 4° C. The bacterial pellet was washed 3 times with 1 ml of sterile 1×PBS (100 mM sodium phosphate, pH 7.4, 150 mM NaCl). Approximately 5 µg of BAR peptide was incubated at 37° C. with 5 µL of the suspended cells or with 51 µl of culture supernatant for 0 to 60 minutes and BAR peptide was visualized using Novex® 10-20% tricine gel (Invitrogen, Carlsbad, Calif.) and Coomassie staining. For some experiments, digital images of the stained gels were obtained using Epson Stylus CX3810 flatbed scanner (Espson America, Inc., Long Beach, Calif.) and analyzed by densitometry using ImageJ software (found on the world-wide-web at rsbweb.nih.gov/ij/).

Inhibition of protease activity. The proteolytic activity of *P. gingivalis* was inhibited using a bacterial protease inhibitor cocktail (Sigma, St. Louis, Mo.) containing the following inhibitors: 4-(2-Aminoethyl)benzenesulfonyl fluoride hydrochloride (AEBSF), N-(trans-epoxysuccinyl)-L-leucine 4 guanidinobutylamide (E-64), sodium ethylenediaminetetraacetate (EDTA), bestatin and pepstatin A. The inhibitor cocktail was suspended in dimethylsulfoxide (DMSO) (Sigma, St. Louis, Mo.) at the concentration recommended by the manufacturer. Intact *P. gingivalis* cells were incubated in serially diluted protease inhibitor cocktail for 30 minutes at ambient temperature prior to the addition of 5 µg of BAR peptide and were subsequently incubated at 37° C. for 2 hours. The presence of intact BAR peptide was determined via SDS-PAGE and Coomassie staining as described above. To determine which inhibitor in the cocktail was required for inhibition of *P. gingivalis* proteolytic activity, bacteria were pre-treated with serial two-fold dilutions of the individual inhibitors that were mixed to generate the cocktail and subsequently incubated with BAR peptide.

*P. gingivalis* biofilm formation with *S. gordonii*. The formation of dual species *P. gingivalis/S. gordonii* biofilms was carried out essentially as previously described by Lamont et al (2002. Microbiology 148:1627-36.) and Daep et al. (Immun 74:5756-62 (2006); Infect Immun 76:3273-80 (2008)). The bacterial biofilms were cultured using a Manostat Carter 4/8 cassette peristaltic pump (Fisher Scientific, Suwanee, Ga.) with 0.89 millimeter platinum-cured silicone tubing (Fisher Scientific, Suwanee, Ga.) and BST FC 71 flow cells (Biosurface Technologies, Corp, Bozeman, Mont.). A single surface of a 24×60 mm cover glass (VWR International, West Chester, Pa.) was coated with 0.22 µm filter sterilized saliva and incubated at 37° C. for 30 minutes. The saliva coated coverglass was then washed with sterile 1×PBS at a flow rate of 6 ml per hour for 30 minutes.

*S. gordonii* DL-1 cells were harvested by centrifugation at 4000 rpm at 4° C. and suspended in 10 ml of sterile 1×PBS. *S. gordonii* cells were labeled with 20 µL of hexidium iodide (1.6 mg/ml, Molecular Probes, Eugene, Oreg.) at 25° C. for 30 minutes in the dark and washed with PBS. To allow the streptococci to attach to the saliva coated cover glass, *S. gordonii* was inoculated into the flow cell at the rate of 6 ml per hour for approximately 2 hours. Following inoculation with *S. gordonii*, the flow cell was washed with sterile PBS for 30 minutes at 6 ml per hour to remove non-adherent bacteria from the cover glass and form a non-confluent layer on the saliva coated coverglass.

*P. gingivalis* cells were harvested by centrifugation at 4000 rpm at 4° C. for 45 minutes, suspended in 20 ml of sterile 1×PBS, and introduced into the flow cell at a flow rate of 6 ml per hour for 2 hours to allow the bacteria to adhere and accumulate on the streptococcal substrate. Flow cells were subsequently washed with sterile 1×PBS to remove the non-adherent *P. gingivalis* cells. To visualize adherent bacteria, rabbit anti-*P. gingivalis* 33277 polyclonal antibody at 1:5000 dilution in 5 ml of sterile 1×PBS was flowed into the cell at a rate of 6 ml/hour for approximately 1 hour. The flow cell was then washed with sterile 1×PBS for 30 minutes, reacted with anti-rabbit IgG fluorescein isothiocyanate (FITC) conjugate antibody (Sigma, St. Louis, Mo.) in sterile 1×PBS (1:5000) for 1 hour at 6 ml/hour, and received a final wash with sterile 1×PBS as above. *P. gingivalis* microcolonies bound to immobilized streptococci were quantified by confocal microscopy as described below.

Inhibition of proteolytic activity in *P. gingivalis/S. gordonii* biofilms. For biofilm inhibition experiments which involved inhibiting bacterial associated proteases, *P. gingivalis* cells were pre-incubated with the 5.8 µM pepstatin A (Sigma, St. Louis, Mo.) prior to treatment with the BAR peptide (Biosynthesis Incorporated, Lewisville, Tex.). The bacteria were incubated with 0 and 0.845 µM peptide at ambient temperature for 30 minutes and introduced into the flow cell containing an existing streptococcal substrate for 2 hours at a flow rate of 6 ml per hour. Biofilm formation was analyzed by confocal microscopy as described below. Data was analyzed using GraphPad InStat3 software (GraphPad Software Co.) using a non-parametric analysis of variance (ANOVA). Dunn's multiple comparisons test was utilized to analyze the data acquired and determine the pair-wise statistical differences in colony number between experimental samples and the control reaction which did not contain a peptide inhibitor.

Confocal analysis of P. gingivalis-S. gordonii biofilms. P. gingivalis-S. gordonii biofilms were visualized using an Olympus Fluoview 500 confocal laser scanning microscope (Olympus, Pittsburgh, Pa.) under 600× magnification using an Argon laser for visualization of FITC labeling and the HeNe-Green laser to visualize the hexidium iodide labeled streptococci. The number and height of FITC-labeled P. gingivalis microcolonies was determined from 30 to 60 randomly chosen frames using the FluoView software package provided by Olympus. Microcolony depth was determined by performing Z-plane scans from 0 to 30 μm above the coverglass surface. Under the culture conditions used, P. gingivalis microcolonies that formed in the absence of BAR peptide ranged from 7 to 16 μM in depth.

Results

Figure 18:
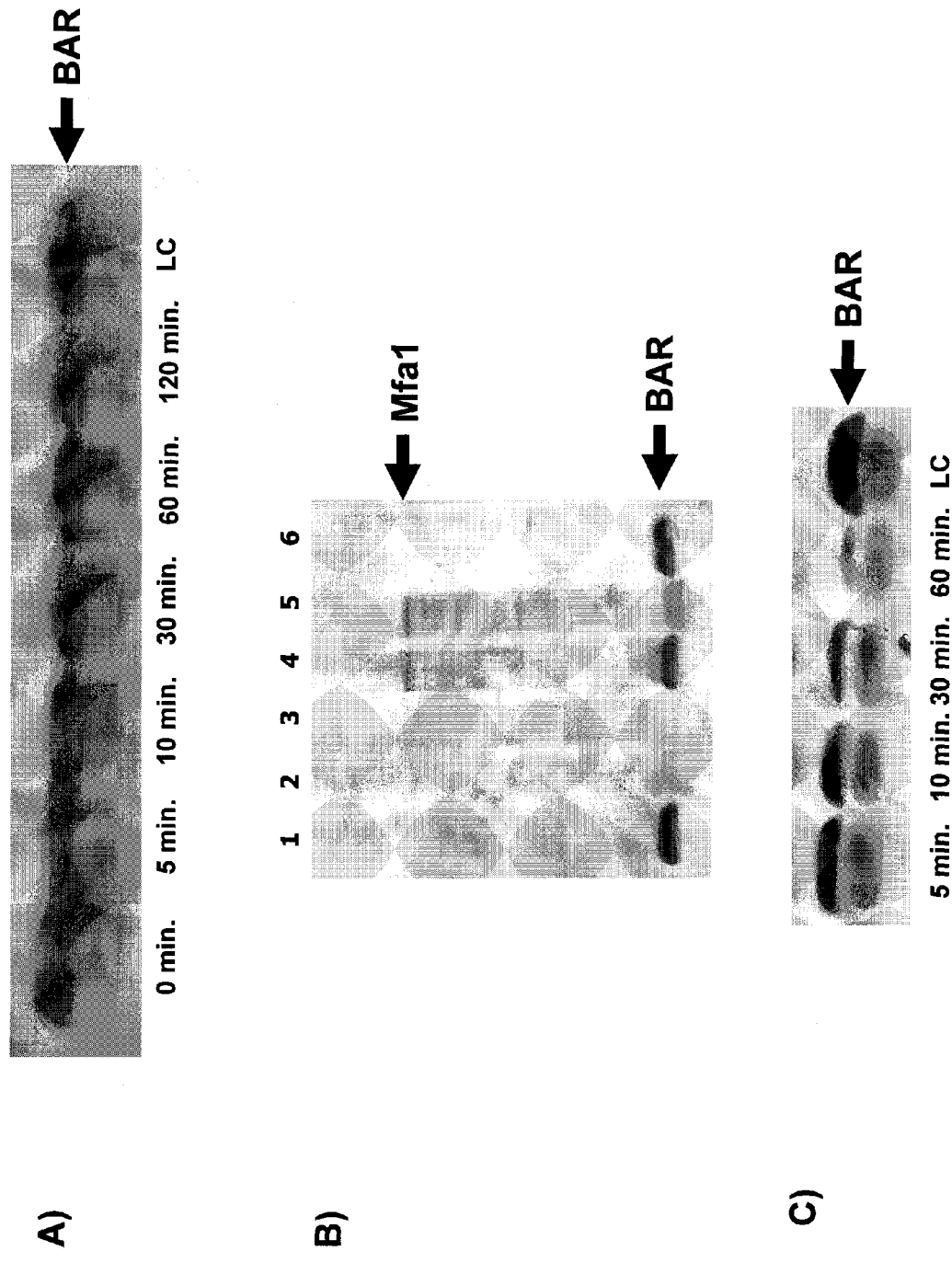
FIG. 18. Degradation of BAR by *P. gingivalis*. A) To determine the stability of BAR peptide in PBS buffer, 5 μg of the peptide was incubated at 37° C. for 0, 5, 10, 30, 60, and 120minutes in buffer and analysis via SDS-PAGE and Coomassie staining. No degradation was observed after 120 minutes. B) The stability of BAR in the presence of intact *P. gingivalis* cells or culture supernatant was determined by incubating 5 μg of the peptide with each for up to 60 minutes at 37° C. C) Incubation of BAR with the supernatant for 0, 5, 10, 30, and 60 minutes showed a time dependent degradation of the peptide, however, incubation of BAR with whole cells resulted in an immediate degradation within 5 minutes. Together, this shows that the peptide is susceptible to cleavage by proteases produced by *P. gingivalis*, with the latter showing that the greatest proteolytic activity against BAR occurs at the cell surface of *P. gingivalis*.

Mfa1 protects BAR peptide from proteolytic degradation by P. gingivalis. We previously identified a functional domain of the SspB (antigen I/II) protein of S. gordonii that interacted with the minor fimbrial antigen (Mfa1) of P. gingivalis and showed that a peptide derived from this region functioned as a potent competitive inhibitor of P. gingivalis/S. gordonii adherence and biofilm formation (Daep et al., Infect Immun 74:5756-62 2006). This suggested that this peptide (designated BAR) was relatively stable in the presence of proteases that are expressed by P. gingivalis. To further assess this, the stability of BAR in the presence and absence of P. gingivalis was determined. As shown in FIG. 18A, BAR peptide was stable when incubated in buffer at 37° C. for 2 hours. However, incubation of the peptide with intact P. gingivalis SMF cells which lack the Mfa1 receptor for BAR resulted in the rapid degradation (see Lanes 2 and 3 in FIG. 18B). Indeed, complete degradation of BAR occurred in less than 5 minutes. As shown in FIG. 18C, the peptide was more slowly degraded by culture supernatant, indicating that the majority of proteolytic activity against BAR is cell associated.

Interestingly, pre-incubation of BAR with purified Mfa1 protein significantly protected the peptide from degradation by intact P. gingivalis cells. Whereas BAR was completely degraded by intact cells within 5 minutes in the absence of Mfa1, little degradation occurred after 5 minutes when Mfa1 was present (compare Lanes 2 and 4 in FIG. 18B). Even after incubation for 30 minutes, intact BAR peptide remained along with a slightly truncated peptide (FIG. 18B, Lane 5). This suggests that the affinity of the BAR-Mfa1 interaction is sufficiently high to reduce but not eliminate degradation mediated by cell associated proteases. Thus, by limiting the susceptibility of BAR to P. gingivalis proteases, a peptide inhibitor with increased potency may be obtained. To address this, experiments to identify the proteases that are responsible for cleavage of BAR were carried out.

Gingipain-mediated cleavage of BAR peptide. The lysine-X (Kgp) and arginine-X (RgpA and RgpB) specific gingipains expressed by P. gingivalis account for the majority of the proteolytic activity of the organism (Curtis et al., 1999. J Periodontal Res 34:464-72; Kuramitsu, H. K. 1998. Oral Microbiol Immunol 13:263-70; Lamont, R. J., and H. F. Jenkinson. 1998. Microbiol Mol Biol Rev 62:1244-63). To determine if degradation of BAR is mediated by the gingipains, the peptide was incubated with intact cells of P. gingivalis strains that lacked either or both of the proteases (see Table 2). As shown in FIG. 19A, little degradation was observed after incubation for 10 minutes with P. gingivalis KDP128 which lacks both the Lys-X and Arg-X gingipains. This suggests that the rapid degradation of BAR is mediated by one or both of the gingipains. A similar result was obtained when BAR was exposed to P. gingivalis KDP129 which lacks only the Lys-X gingipains (see FIG. 19B), suggesting that the rapid degradation of BAR is primarily carried out by the Lys-X specific gingipain. Consistent with this, strain E8 which lacks the Arg-X specific gingipains but retains the Lys-X gingipains rapidly degraded BAR (FIG. 19C). However, although the absence of the Lys-X gingipain significantly reduced the rapid loss of BAR, the peptide was still degraded upon longer exposures to the lys-X gingipain deficient strains KGP128 and KDP129, indicating that additional proteases are present and active against BAR. Thus, any strategy to limit the susceptibility of BAR to proteolytic cleavage by P. gingivalis must target multiple proteases.

Figure 20:
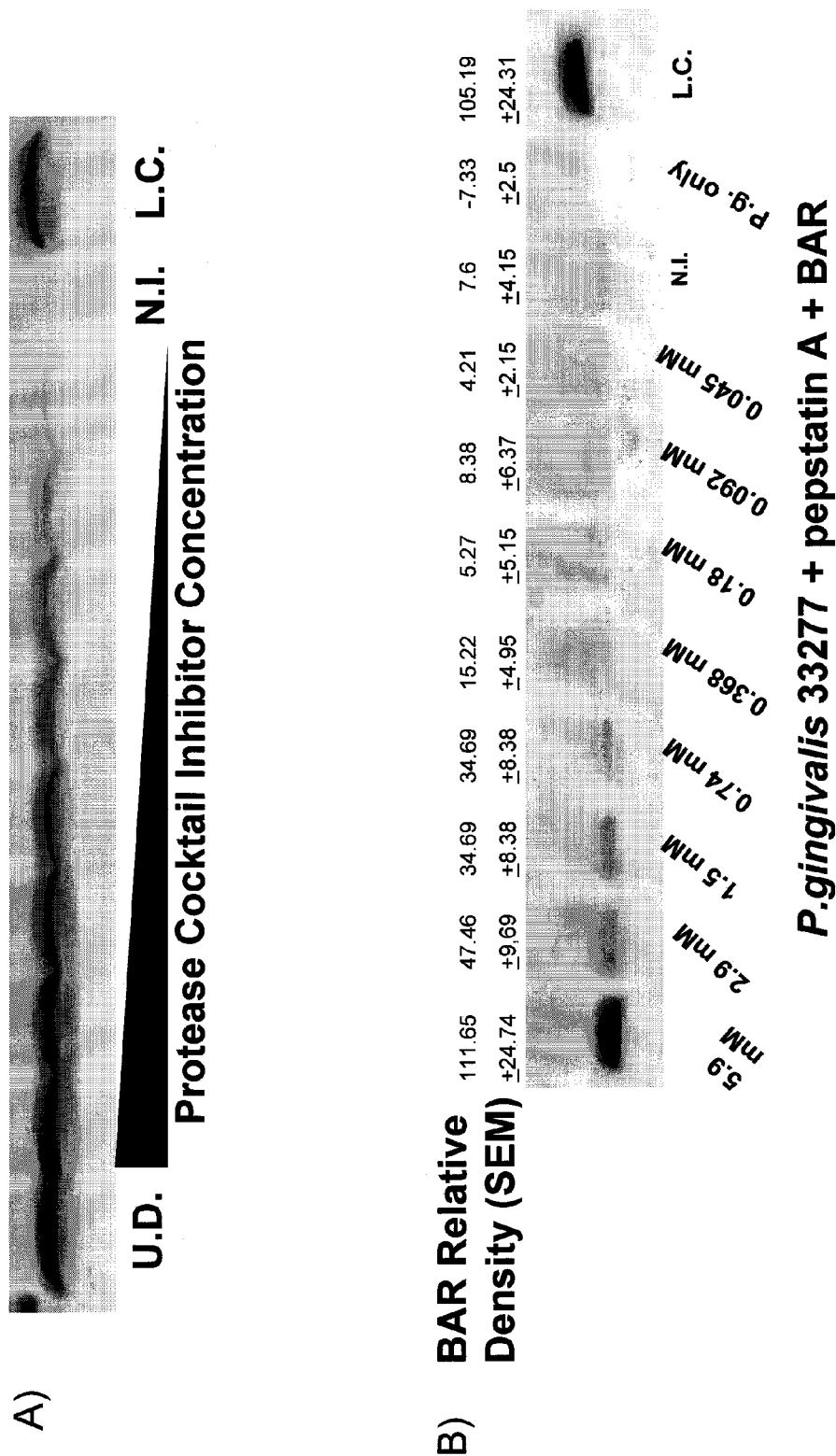
FIG. 20. The gingipains produced by *P. gingivalis* play a prominent role in the BAR proteolysis. Co-incubation of the 5 μg of BAR with *P. gingivalis* 33277 resulted in the immediate degradation of the peptide; however, the addition of BAR to the gingipain deficient strain, *P. gingivalis* KDP128 resulted in an attenuated proteolytic activity against the peptide. This is evident when the relative densities of the remaining BAR peptide were compared for each reaction. While no degradation of the BAR was observed for the gingipain deficient bacteria at T=5 (R.D.=96.23) and 10 minutes (R.D.=115.85) as compared with the loading control (R.D.=115.85), a predominant amount of the peptide was observed to be eventually degraded at the later time points (T=30, 60, and 120 minutes) though not to the same rate as wild type *P. gingivalis*. To determine if BAR could be protected from proteolytic cleavage by *P. gingivalis*, bacteria were treated with serial two-fold dilutions of a protease inhibitor cocktail containing AEBSF, EDTA, E-64, bestatin and pepstatin prior to the addition of BAR. A) the protease inhibitor cocktail limited the degradation of BAR in a dose-dependent manner with complete protection being observed at a 1:8 dilution. B) Of the inhibitors in the mixture, pepstatin A completely prevented the degradation of BAR at a concentration of 6.0 μM and was the most potent inhibitor of *P. gingivalis* proteolytic activity. AEBSF, E-64, EDTA and bestatin were less potent inhibitors and prevented cleavage of BAR at concentrations in the mM range.

Inhibition of proteolytic cleavage of BAR. To determine if BAR could be protected from proteolytic cleavage by P. gingivalis, bacteria were treated with serial two-fold dilutions of a commercially available protease inhibitor cocktail containing AEBSF, EDTA, E-64, bestatin and pepstatin (see Materials and Methods) prior to the addition of BAR. As shown in FIG. 20A, the protease inhibitor cocktail limited the degradation of BAR in a dose-dependent manner with complete protection being observed at a 1:8 dilution. To determine which of the inhibitors in the mixture were most effective, P. gingivalis was next pre-incubated with each of the individual compounds. As shown in FIG. 20B, pepstatin A completely prevented the degradation of BAR at a concentration of 6.0 μM and was the most potent inhibitor of P. gingivalis proteolytic activity. AEBSF, E-64, EDTA and bestatin were less potent inhibitors and prevented cleavage of BAR at concentrations in the mM range.

BAR-mediated inhibition of P. gingivalis biofilm formation. To determine if limiting the degradation of BAR increases its effectiveness in blocking the formation of dual species P. gingivalis/S. gordonii biofilms, biofilm cultures were grown in the presence of BAR peptide using P. gingivalis cells that were pre-treated with PBS containing 6 μM pepstatin A or with PBS alone. Data from similar biofilm cultures grown with varying concentrations of BAR are summarized in Table 3. Without pre-treatment with pepstatin A, BAR inhibited P. gingivalis microcolony formation by 5%, 16%, and 42% at concentrations 0.17, 0.34, and 0.85 μM, respectively. In contrast, the same concentrations of BAR resulted in 20%, 60% and 70% inhibition when P. gingivalis was treated with pepstatin A. These Results suggest that inhibiting prteolytic degradation BAR increase its specific inhibitory activity by approximately 2-fold.

TABLE 3

BAR inhibitory activity in the presence of pepstatin A

| | w/o 5.8 mM pepstatin A | | | | w/5.8 mM pepstatin A | | | |
|---|---|---|---|---|---|---|---|---|
| Peptide (μM) | Colonies | Frames | Colonies/Frame[a] (Mean +/− SEM) | % Inhibition Relative to 0 mM[b] | Colonies | Frames | Colonies/Frame[a] (Mean +/− SEM) | % Inhibition[b] Relative to 0 μM[b] |
| 0 | 278 | 48 | 6.04 ± 0.77 | 0 | 278 | 48 | 6.04 ± 0.77 | 0 |
| 0.169 | 178 | 31 | 5.74 ± 0.51 | 4.99 | 150 | 31 | 4.85 ± 0.66 | 19.93 |
| 0.338 | 246 | 50 | 4.92 ± 0.65 | 18.56 | 134 | 40 | 3.35 ± 0.71 | 44.57 |
| 0.845 | 139 | 40 | 3.48 ± 0.54 | 42.5 | 78 | 40 | 1.95 ± 0.46 | 67.73 |
| 1.65 | 11 | 30 | 0.37 ± 0.17 | 93.39 | 4 | 30 | 0.13 ± 0.06 | 97.79 |

[a]The number of colonies was determined from a total of 30 to 50 total frames per peptide concentration.
[b]The number of colonies per frame was initially normalized against 0 μM peptide which did not contain any pepstatin A. The percent inhibition was determined using the following equation: % inhibition = (normalized avg. colony per frame/0 μM colony per frame) * 100.

Lysine gingipains play a prominent role in BAR peptide degradation. To identify which of the two major proteases, Kgp and Rgp, produced by *P. gingivalis* is important in the degradation of the BAR peptide, 5 μg of BAR was incubated with either a Kgp-deficient (KDP129) or RgpA/B-deficient (E8) strain of *P. gingivalis* for 0, 5, 10, 30, 60, and 120 minutes at 37° C. The relative densities of the remaining BAR peptide were then compared. Similar to the wild type strain 33277 (FIG. 19), addition of BAR with the E8 whole cells showed an immediate degradation of the peptide within 5 minutes (R.D.=32.5 vs. 21.6). However, the incubation of BAR with the KDP129 whole cell resulted in an attenuated degradation of the peptide with results mirroring those previously observed for Kgp⁻/RgpA⁻/RgpB⁻ KDP128 with the eventual degradation of the peptide at later time points. These results suggest that while the Kgp produced by *P. gingivalis* play a major role in the proteolysis of the BAR peptide while other proteases may also play a role in the BAR degradation.

Inhibition of proteases limits BAR degradation by *P. gingivalis*. To determine whether the proteolysis of BAR by *P. gingivalis* proteases could be limited, the bacteria were pretreated with 2-fold diluted protease inhibitor cocktail. The amount of BAR left intact was then determined by coomassie staining of the Tricine gel. The relative density of the remaining peptide was compared with the loading control (L.C.) containing only 5 μg of the peptide. No degradation of the BAR peptide was observed for the bacteria treated with undiluted (U.D.) inhibitor cocktail while the sample containing no inhibitors (N.I.) reflected previous results which showed BAR degradation. Furthermore, a dose dependant inhibition of BAR proteolysis was observed for the intermediate concentrations of the protease inhibitor cocktail. The individual inhibitor components of the cocktail were tested for their limiting activity on the proteases starting at the $2^{-3}$ dilution. Screening of specific protease inhibitors showed that pepstatin A was the most potent inhibitor of protease activity with complete inhibition occurring at the concentration of approximately 5.9 μM. The remaining BAR peptide at the highest concentration had a relative density equaling to the loading control (R.D.=111.65 vs. 105.19).

DISCUSSION

The inventors previously showed that BAR peptide potently inhibits ($I_{50}$=1.3 μM) *P. gingivalis/S. gordonii* interspecies adherence and biofilm formation (Daep et al., 2006, Infect Immun 74:5756-62), which suggests that BAR may be relatively resistant to the proteolytic activities that are expressed by *P. gingivalis*. This study examined the activity of *P. gingivalis* proteases against BAR peptide and surprisingly, the peptide was found to be rapidly degraded by intact bacterial cells, but only slowly degraded by culture supernatant. This is consistent with Yoshimura et al. who showed that the majority of *P. gingivlais* proteolytic activity is surface associated rather than secreted (1984, Arch Oral Biol 29:559-64). However, these results question how a peptide that is rapidly degraded by intact *P. gingivalis* can function as a potent competitive inhibitor of bacterial adherence and biofilm development. Interestingly, the addition of purified Mfa1 protein (the receptor for BAR) to the peptide/*P. gingivalis* mixture afforded significant protection from rapid proteolytic cleavage. This suggests that the affinity of BAR for its receptor may be significantly higher than for *P. gingivalis* proteases. Indeed, we previously calculated the dissociation constant of the BAR-Mfa1 interaction to be approximately 0.9 μM. Thus, BAR peptide may selectively partition to its receptor resulting in inhibition of *P. gingivalis* adherence to *S. gordonii*, which is the initial step in dual species biofilm formation.

The predominant proteases expressed by *P. gingivalis* are the gingipains and our results show that that it is the Lys-X specific gingipain that is primarily responsible for the rapid degradation of BAR by intact bacteria. This is consistent with the primary sequence of BAR which contains five lysine residues. However, tandem Lys residues are not good substrates for the Lys-X gingipains and four of the five Lys residues in BAR exist as Lys-Lys-X. This suggests that the Lys-X gingipain may cleave BAR most efficiently at Lys1186 (see FIG. 17) and the size of resulting cleavage product comprising residues 1167-1186, is consistent with the truncated peptide observed when BAR was incubated with *P. gingivalis* in the presence of Mfa1 (FIG. 18C, Lane 5). The eventual further degradation of BAR in the Lys-X gingipain deficient mutant indicates that other proteases of *P. gingivalis* cleave BAR as well. Indeed, further analysis of the BAR sequence suggests that it may be a substrate for the *P. gingivalis* caseinolytic proteases Pase-A, Pase-B, and Pase-C (17), which cleave C-terminally at Lys, Gln and Ala residues. Thus, attempts to improve the biofilm inhibitory activity of BAR by limiting its degradation by *P. gingivalis* must target multiple proteases.

Our initial experiment to reduce degradation of the peptide utilized a protease inhibitor cocktail, which was shown to completely protect BAR when diluted up to 1:8. Among the components in the inhibitor cocktail, the aspartyl protease inhibitor pepstatin A was shown to be the most potent inhibitor of the BAR susceptibility to protease activity. However, it is possible that the other Arg-/Lys-specific proteases produced by *P. gingivalis* may be inhibited by the protease inhibitor. If this is true, then these other proteases would play a more major role in the degradation of the BAR peptide and would therefore be worthwhile in assessing their role in BAR proteolysis.

Nonetheless, BAR is eventually degraded even in the presence of Mfa1 suggesting that by limiting proteolytic degradation, the potency of inhibition can be increased. Our current results have suggested that the ability of the BAR peptide to inhibit the interaction between *P. gingivalis* and *S. gordonii* could be elevated by limiting its susceptibility to protease activity. In this study we have shown that pre-treatment of *P. gingivalis* with a protease inhibitor, pepstatin A, prior to the addition of the BAR peptide resulted in an increase of specific inhibitor activity of the peptide. These results are consistent with our previous reports which showed that the BAR peptide is a potent competitive inhibitor of *P. gingivalis/S. gordonii* biofilm formation (Daep et al., 2006 Infect Immun 74:5756-62). Consistent with our hypothesis and the data in this report, the inhibitory activity of BAR was increased when *P. gingivalis* was pre-treated with the protease inhibitor, pepstatin A, prior to the treatment with peptide. It is possible to speculate that the specific inhibitory activity of BAR could be increased by protecting the amino acid residues (i.e. structure modification) which are susceptible to proteolysis. Our current attempt at limiting proteolytic activity against BAR involved the replacement of the entire peptide backbone with R-enantiomers of each of the amino acids (Retro-Inverse BAR: RI-BAR). Despite the loss of proteolytic activity against the peptide (data not shown), RI-BAR was a poor inhibitor of *P. gingivalis/S. gordonii* co-aggregation (Daep et al., 2006 Infect Immun 74:5756-62). While the complete replacement of the L-amino acids may limit the potential hydrogen bonding occurring between the BAR peptide side-chain and the Mfa1 backbone, it may still be possible to limit proteolysis and thus increase BAR inhibitory activity through selective replacement of susceptible residues with either their D-amino acids or other synthetic residues.

Our current study is consistent with previous reports which showed that the BAR peptide is a potent inhibitor of *P. gingivalis/S. gordonii* biofilm formation (Daep et al., 2006 Infect Immun 74.5756-62; Daep et al., 2008, Infect Immun 76:3273-80). Data from this report shows that peptide inhibitor is susceptible to susceptible to proteolytic activity, in particular to the gingipains produced by the oral pathogen *P. gingivalis*. Limitation of protease activity against BAR has been shown to increase the inhibitory activity of the peptide. These results may provide additional rationale for the development of additional BAR analogues which would have higher specific inhibitory activity against *P. gingivalis/S. gordonii* biofilm formation.

EXAMPLE 7

Glu$^{1168}$ is Important in Mfa1-BAR Interaction

In silico analysis of the SspB polypeptide has predicted that the N-terminal region of the BAR peptide forms an α-helix despite the presence of a Pro residue at position 1171 of the protein. While Pro is considered to be a classical helix-breaking amino acid, it is known that Pro may be tolerated within α-helices. These Pro residues introduce a structurally important kink within the α-helical backbone as found among many ion channels and transporters. Studies characterizing these proteins have identified the carbonyl residues located at the −3 and −4 positions from the Pro is exposed to the local environment and serve as a binding site for cations (i.e. $Ca^{2+}$, $Mg^{2+}$) (Sansom., 1992, Protein Engineering. 5:53-60). Interestingly, analysis of the SspB/BAR sequence shows that the residue located at the −3 position from Pro$^{1171}$ is a negative charged Glu. Previous studies (Duan et al. 1994, Infect. Immun. 73:1545-1552) showed that SspB is a calcium binding protein and that sequences important for calcium binding mapped to the region of the protein that was later shown by us to mediate *P. gingivalis* adherence. This suggests that the activity of BAR may be related to the calcium binding function of SspB and that the Glu-X-X-Pro (SEQ ID NO: 14) motif may be important for inhibitory activity of BAR.

Analysis for the Role of Glu$^{1168}$ in BAR Binding Activity to Mfa1.

Figure 21:
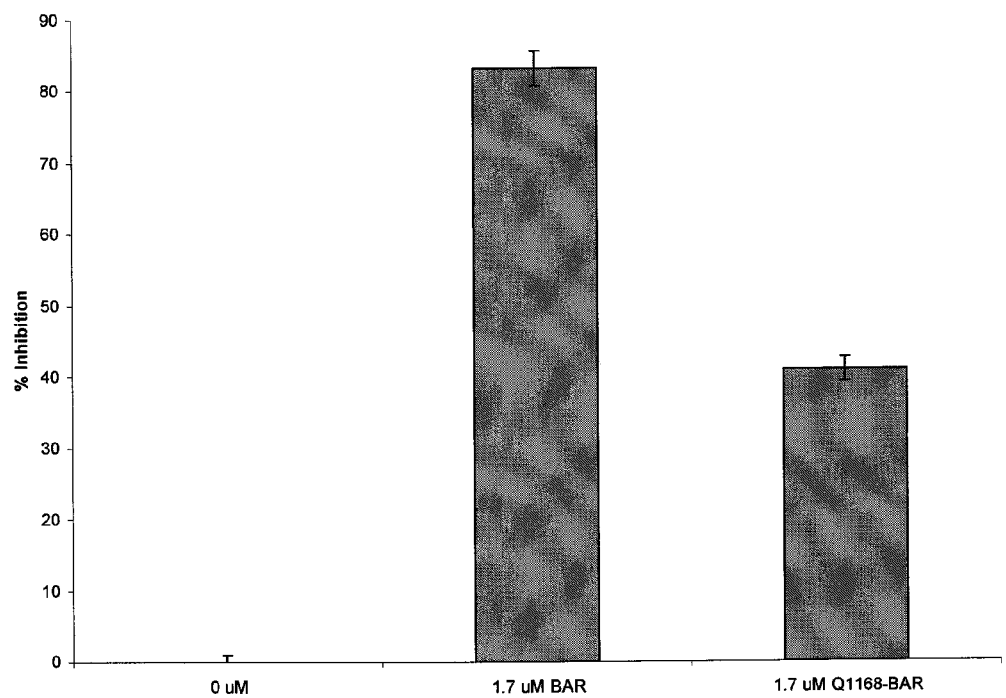
FIG. 21. Comparison of BAR inhibitory activity to BAR-XIV. Pre-treatment of *P. gingivalis* with 1.7 μM BAR-XIV showed a significant decrease in inhibitory activity compared to the original BAR peptide. Increasing the concentration 10-fold (17 µM) did not show partial or full restoration of the BAR ortholog's inhibitory activity.
Figure 22:
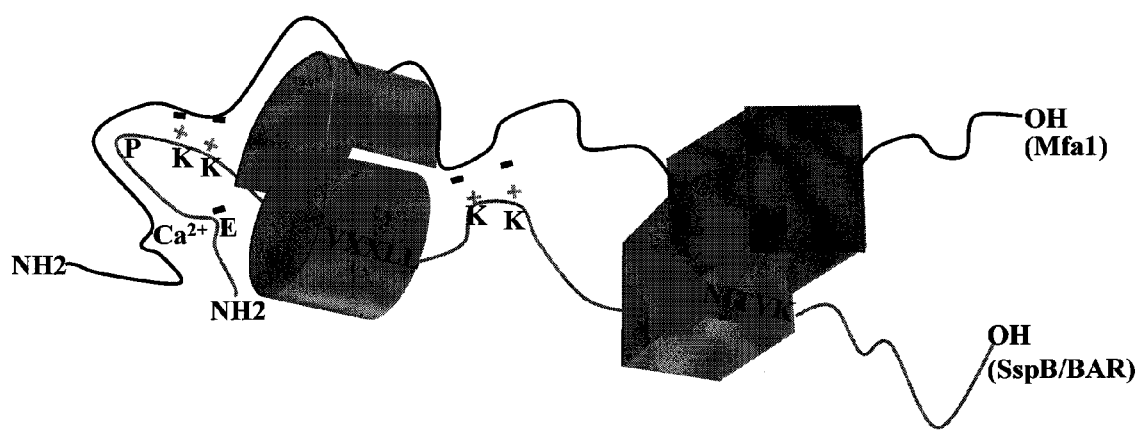
FIG. 22. Updated model for BAR/Mfa1 interaction. Current studies characterizes potential mechanistic activity of the BAR peptide. While initial interaction between Mfa1 and BAR may occur between the nuclear receptor co-activator box-like motif, VXXLL (SEQ ID NO: 3), species specific interaction between *P. gingivalis* and *S. gordonii* is dictated by the downstream motif, NITVK (SEQ ID NO: 2). In addition the Pro$^{1171}$ may provide a structurally important kink within the predicted α-helical region of the BAR peptide. This kink may potentially allow for the proper presentation of the VXXLL (SEQ ID NO: 3) and NITVK (SEQ ID NO: 2) motifs to their binding sites in Mfa1. Finally, while the exact role of Ca$^{2+}$ in this protein-protein interaction has to be fully elucidated, current studies suggest that the negative charged Glu$^{1168}$ also contributes in the adherence of Mfa1 to BAR (SspB).

To identify the role of Glu$^{1168}$ in BAR-Mfa1 interaction, the negative charged residue was substituted with a neutral charged Gln in the BAR-XIV peptide (FIGS. 21-22). The binding activity of BAR-XIV to *P. gingivalis* was tested via the biofilm inhibition assay. *P. gingivalis* was initially pre-treated with 1.7 µM of BAR-XIV. The results showed that BAR-XIV did not inhibit the formation of *P. gingivalis/S. gordonii* biofilm formation as effectively as BAR (45% vs. 80% inhibition rates respectively) as indicated in Table 4 below.

TABLE 4

BAR vs BAR-XIV Sequence

| Peptide | Description | Sequence |
|---------|-------------|----------|
| BAR | | LEAAPKKVQDLLKKANITVKGAFQLFS (SEQ ID NO: 15) |
| BAR-XIV | BAR ortholog containing the substitution Gln/Glu$^{1168}$ | LQAAPKKVQDLLKKANITVKGAFQLFS (SEQ ID NO: 16) |

$^1$The residues underlined have been identified to be functional motifs which are important in the interaction between Mfa1 of *P. gingivalis* and BAR (SspB).

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A peptide consisting of a compound of Formula I (SEQ ID NO: 53):

$R_{18}$-$R_1$-$R_2$-Val-$R_3$-$R_4$-Leu-Leu-$R_5$-$R_6$-$R_7$-Ile-$R_8$-$R_9$-Lys-$R_{10}$-$R_{19}$ wherein $R_2$ is 1-3 Lys residues;
$R_3$ is any amino acid residue except a Pro residue;
$R_4$ is any amino acid residue except a Pro residue;
$R_5$ is 1-3 Lys residues;
$R_6$ is 1-10 amino acid residues;
$R_7$ is any amino acid residue except Asp, Glu, Gly or Pro;
$R_8$ is any amino acid residue except Ala, Asp, Gly, His, Ile, Pro, Trp or Tyr;
$R_9$ is a Val, Ile, Phe, or Trp residue;
$R_{10}$ is 0-1 Cys residue;
$R_{18}$ is 0 amino acids or $R_{12}$-$R_{11}$-Pro-,
  wherein $R_{11}$ is 0-3 amino acids, wherein the amino acid residues are not Gly or Pro; and
  $R_{12}$ is 0-1 Cys residues; and
$R_{19}$ is -$R_{13}$-$R_{14}$-$R_{15}$-$R_{16}$-$R_{17}$,
  wherein $R_{13}$ is 0-1 is Gly residue;
  $R_{14}$ is 0-1 Ala residue;
  $R_{15}$ is 0-1 Phe residue;
  $R_{16}$ is 0-1 Gln residue;
  $R_{17}$ is 0-1 Cys residue; and
wherein $R_1$ is an ornithine residue; or wherein both $R_1$ and $R_{10}$ are both Cys and $R_1$ and $R_{10}$ are covalently linked to form a circular peptide; or wherein $R_1$ is 0-1 Cys or an ornithine residue and $R_{12}$ and $R_{17}$ are both Cys and $R_{12}$ and $R_{17}$ are covalently linked to form a circular peptide.

2. The peptide according to claim 1, wherein $R_3$ is Gln.

3. The peptide according to claim 1, wherein $R_4$ is Asp.

4. The peptide according to claim 1, wherein $R_6$ is a single amino acid residue.

5. The peptide according to claim 1, wherein $R_7$ is an Asn residue.

6. The peptide according claim 1, wherein, $R_8$ is Thr.

7. A peptide consisting of a compound of Formula I (SEQ ID NO: 53):

$R_{18}$-$R_1$-$R_2$-Val-$R_3$-$R_4$-Leu-Leu-$R_5$-$R_6$-$R_7$-Ile-$R_8$-$R_9$-Lys-$R_{10}$-$R_{19}$ wherein $R_1$ is 0-1 Cys or ornithine residue;
$R_2$ is 1-3 Lys residues;
$R_3$ is any amino acid residue except a Pro residue;
$R_4$ is any amino acid residue except a Pro residue;
$R_5$ is 1-3 Lys residues;
$R_6$ is 1-10 amino acid residues;
$R_7$ is any amino acid residue except Asp, Glu, Gly or Pro;
$R_8$ is any amino acid residue except Ala, Asp, Gly, His, Ile, Pro, Trp or Tyr;
$R_9$ is a Val, Ile, Phe, or Trp residue;
$R_{10}$ is 0-1 Cys residue;
$R_{18}$ is 0 amino acids or $R_{12}$-$R_{11}$-Pro-,
$R_{11}$ is a tripeptide consisting of Glu-Ala-Ala; and
$R_{12}$ is 0-1 Cys residues; and
$R_{19}$ is -$R_{13}$-$R_{14}$-$R_{15}$-$R_{16}$-$R_{17}$,
  wherein $R_{13}$ is 0-1 is Gly residue;
  $R_{14}$ is 0-1 Ala residue;
  $R_{15}$ is 0-1 Phe residue;
  $R_{16}$ is 0-1 Gln residue; and
  $R_{17}$ is 0-1 Cys residue.

8. The peptide according to claim 1, wherein the peptide has greater structural constraint than native SspB Adherence Region (BAR).

9. The peptide according to claim 1, wherein the peptide contains an unnatural amino acid residue.

10. The peptide according to claim 1, wherein the peptide forms an alpha-helix.

11. A composition comprising the peptide according to claim 1 or claim 7 and a physiologically acceptable carrier.

12. The composition of claim 11, further comprising a protease inhibitor.

13. A peptide-coated device comprising:
  (a) a solid substrate; and
  (b) a solid composite of
    (i) a peptide according to claim 1 or
    (ii) a peptide consisting of the compound of Formula I (SEQ ID NO: 53):

$R_{18}$-$R_1$-$R_2$-Val-$R_3$-$R_4$-Leu-Leu-$R_5$-$R_6$-$R_7$-Ile-$R_8$-$R_9$-Lys-$R_{10}$-$R_{19}$ wherein $R_1$ is 0-1 Cys or ornithine residue;
$R_2$ is 1-3 Lys residues;
$R_3$ is any amino acid residue except a Pro residue;
$R_4$ is any amino acid residue except a Pro residue;
$R_5$ is 1-3 Lys residues;
$R_6$ is 1-10 amino acid residues;
$R_7$ is any amino acid residue except Asp, Glu, Gly or Pro;
$R_8$ is any amino acid residue except Ala, Asp, Gly, His, Ile, Pro, Trp or Tyr;
$R_9$ is a Val, Ile, Phe, or Trp residue;
$R_{10}$ is 0-1 Cys residue;
$R_{18}$ is 0 amino acids or $R_{12}$-$R_{11}$-Pro-,
  $R_{11}$ is a tripeptide consisting of Glu-Ala-Ala; and
  $R_{12}$ is 0-1 Cys residues; and
$R_{19}$ is -$R_{13}$-$R_{14}$-$R_{15}$-$R_{16}$-$R_{17}$,
  wherein $R_{13}$ is 0-1 is Gly residue;
  $R_{14}$ is 0-1 Ala residue;
  $R_{15}$ is 0-1 Phe residue;
  $R_{16}$ is 0-1 Gln residue; and
  $R_{17}$ is 0-1 Cys residue
and a therapeutic substance in an adherent layer on the solid substrate.

14. The device according to claim 13, wherein the solid substrate has a metal surface.

15. A device according to claim 13, wherein the solid substrate has a polymeric surface.

16. A device according to claim 13, wherein the solid composite includes a plurality of layers.

17. A device according to claim 15, wherein the solid composite includes a plurality of layers, and wherein the ratio of therapeutic substance to polymer is varied in some of the layers.

18. A device according to claim 15, wherein the polymer is a bioabsorbable or biostable polymer.

* * * * *